(12) United States Patent
Fung et al.

(10) Patent No.: US 10,959,734 B2
(45) Date of Patent: Mar. 30, 2021

(54) TISSUE LIGATION DEVICES AND METHODS THEREFOR

(71) Applicant: SentreHEART, Inc., Redwood City, CA (US)

(72) Inventors: Gregory W. Fung, Redwood Shores, CA (US); Alan L. Bradley, San Francisco, CA (US); Russell Pong, Newark, CA (US); Robert L. Clark, III, Hayward, CA (US); Arnold M. Escano, San Jose, CA (US)

(73) Assignee: SentreHEART LLC, Redwood City, CA (US)

( * ) Notice: Subject to any disclaimer, the term of this patent is extended or adjusted under 35 U.S.C. 154(b) by 103 days.

(21) Appl. No.: 16/149,911

(22) Filed: Oct. 2, 2018

(65) Prior Publication Data

US 2019/0125350 A1    May 2, 2019

Related U.S. Application Data

(63) Continuation of application No. 15/080,398, filed on Mar. 24, 2016, now Pat. No. 10,130,369.
(Continued)

(51) Int. Cl.
  *A61B 17/12* (2006.01)
  *A61B 17/04* (2006.01)
  *A61B 17/00* (2006.01)

(52) U.S. Cl.
  CPC .... *A61B 17/12013* (2013.01); *A61B 17/0487* (2013.01); *A61B 2017/00243* (2013.01);
  (Continued)

(58) Field of Classification Search
  CPC .......... A61B 17/0487; A61B 17/12013; A61B 2017/00867
  See application file for complete search history.

(56) References Cited

U.S. PATENT DOCUMENTS

| 3,435,905 A | 4/1969 | Lazarus |
| 3,496,932 A | 2/1970 | Prisk et al. |

(Continued)

FOREIGN PATENT DOCUMENTS

| CN | 101262823 B | 12/2011 |
| DE | 3714492 A1 | 11/1987 |

(Continued)

OTHER PUBLICATIONS afibfacts.com (Date Unknown). "Cox-Maze III: The Gold Standard Treatment for Atrial Fibrillation: Developing a Surgical Option for Atrial Fibrillation," located at <http://www.afibfacts.com/Treatment_Options_for_Atrial_Fibrillation/Cox-Maze_III%_3a_The_Gold_Standard_Treatment_for_Atrial_Fibrillation >, last visited on Apr. 20, 2007, 4 pages.
(Continued)

*Primary Examiner* — Richard G Louis
(74) *Attorney, Agent, or Firm* — Cooley LLP

(57) ABSTRACT

Described herein are tissue closure devices and methods for ligating a target tissue, such as the left atrial appendage. The tissue closure devices may have an elongate body, a snare at least partially housed within the elongate body, a suture at least partially housed within the elongate body, and a tightening element coupled to the suture. The suture may have a suture loop, and the tightening element may be configured to decrease the size of the suture loop when the area of a tissue within the suture loop decreases.

20 Claims, 33 Drawing Sheets

Related U.S. Application Data

(60) Provisional application No. 62/137,740, filed on Mar. 24, 2015.

(52) U.S. Cl.
CPC .............. *A61B 2017/00867* (2013.01); *A61B 2017/0488* (2013.01)

(56) References Cited

U.S. PATENT DOCUMENTS

| | | |
|---|---|---|
| 3,677,597 A | 7/1972 | Stipek |
| 3,802,074 A | 4/1974 | Hoppe |
| 3,841,685 A | 10/1974 | Kolodziej |
| 3,999,555 A | 12/1976 | Person |
| 4,018,229 A | 4/1977 | Komiya |
| 4,030,509 A | 6/1977 | Heilman et al. |
| 4,078,305 A | 3/1978 | Akiyama |
| 4,181,123 A | 1/1980 | Crosby |
| 4,249,536 A | 2/1981 | Vega |
| 4,257,278 A | 3/1981 | Papadofrangakis et al. |
| 4,319,562 A | 3/1982 | Crosby |
| 4,428,375 A | 1/1984 | Ellman |
| 4,596,530 A | 6/1986 | McGlinn |
| 4,662,377 A | 5/1987 | Heilman et al. |
| 4,765,341 A | 8/1988 | Mower et al. |
| 4,776,844 A | 10/1988 | Ueda |
| 4,817,608 A | 4/1989 | Shapland et al. |
| 4,901,405 A | 2/1990 | Grover et al. |
| 4,944,753 A | 7/1990 | Burgess et al. |
| 4,991,578 A | 2/1991 | Cohen |
| 4,991,603 A | 2/1991 | Cohen et al. |
| 4,998,975 A | 3/1991 | Cohen et al. |
| 5,033,477 A | 7/1991 | Chin et al. |
| 5,108,406 A | 4/1992 | Lee |
| 5,163,942 A | 11/1992 | Rydell |
| 5,163,946 A | 11/1992 | Li |
| 5,176,691 A | 1/1993 | Pierce |
| 5,181,123 A | 1/1993 | Swank |
| 5,226,535 A | 7/1993 | Roshdy et al. |
| 5,226,908 A | 7/1993 | Yoon |
| 5,242,459 A | 9/1993 | Buelna |
| 5,243,977 A | 9/1993 | Trabucco et al. |
| 5,269,326 A | 12/1993 | Verrier |
| 5,279,539 A | 1/1994 | Bohan et al. |
| 5,281,238 A | 1/1994 | Chin et al. |
| 5,300,078 A | 4/1994 | Buelna |
| 5,306,234 A | 4/1994 | Johnson |
| 5,312,423 A | 5/1994 | Rosenbluth et al. |
| 5,318,578 A | 6/1994 | Hasson |
| 5,330,488 A | 7/1994 | Goldrath |
| 5,336,229 A | 8/1994 | Noda |
| 5,336,231 A | 8/1994 | Adair |
| 5,336,252 A | 8/1994 | Cohen |
| 5,385,156 A | 1/1995 | Oliva |
| 5,387,219 A | 2/1995 | Rappe |
| 5,398,944 A | 3/1995 | Holster |
| 5,403,331 A | 4/1995 | Chesterfield et al. |
| 5,405,351 A | 4/1995 | Kinet et al. |
| 5,417,684 A | 5/1995 | Jackson et al. |
| 5,423,821 A | 6/1995 | Pasque |
| 5,423,830 A | 6/1995 | Schneebaum et al. |
| 5,433,457 A | 7/1995 | Wright |
| 5,433,730 A | 7/1995 | Alt |
| 5,443,481 A | 8/1995 | Lee |
| 5,449,361 A | 9/1995 | Preissman |
| 5,449,637 A | 9/1995 | Kadry |
| 5,465,731 A | 11/1995 | Bell et al. |
| 5,494,240 A | 2/1996 | Waugh |
| 5,498,228 A | 3/1996 | Royalty et al. |
| 5,522,819 A | 6/1996 | Graves et al. |
| 5,540,711 A | 7/1996 | Kieturakis et al. |
| 5,545,178 A | 8/1996 | Kensey et al. |
| 5,571,161 A | 11/1996 | Starksen |
| 5,591,177 A | 1/1997 | Lehrer |
| 5,609,597 A | 3/1997 | Lehrer |
| 5,624,430 A | 4/1997 | Eton et al. |
| 5,624,453 A | 4/1997 | Ahmed |
| 5,634,895 A | 6/1997 | Igo et al. |
| 5,636,780 A | 6/1997 | Green et al. |
| 5,676,162 A | 10/1997 | Larson, Jr. et al. |
| 5,676,651 A | 10/1997 | Larson, Jr. et al. |
| 5,678,547 A | 10/1997 | Faupel et al. |
| 5,681,278 A | 10/1997 | Igo et al. |
| 5,682,906 A | 11/1997 | Sterman et al. |
| 5,683,348 A | 11/1997 | Diener |
| 5,683,364 A | 11/1997 | Zadini et al. |
| 5,683,445 A | 11/1997 | Swoyer |
| 5,693,059 A | 12/1997 | Yoon |
| 5,693,091 A | 12/1997 | Larson, Jr. et al. |
| 5,699,748 A | 12/1997 | Linskey, Jr. et al. |
| 5,702,430 A | 12/1997 | Larson, Jr. et al. |
| 5,707,336 A | 1/1998 | Rubin |
| 5,716,367 A | 2/1998 | Koike et al. |
| 5,716,392 A | 2/1998 | Bourgeois et al. |
| 5,727,569 A | 3/1998 | Benetti et al. |
| 5,728,151 A | 3/1998 | Garrison et al. |
| 5,735,877 A | 4/1998 | Pagedas |
| 5,741,281 A | 4/1998 | Martin |
| 5,752,526 A | 5/1998 | Cosgrove |
| 5,766,151 A | 6/1998 | Valley et al. |
| 5,766,216 A | 6/1998 | Gangal et al. |
| 5,766,217 A | 6/1998 | Christy |
| 5,769,863 A | 6/1998 | Garrison |
| 5,779,727 A | 7/1998 | Orejola |
| 5,788,715 A | 8/1998 | Watson, Jr. et al. |
| 5,792,151 A | 8/1998 | Heck et al. |
| 5,797,870 A | 8/1998 | March et al. |
| 5,797,929 A | 8/1998 | Andreas et al. |
| 5,797,946 A | 8/1998 | Chin |
| 5,799,661 A | 9/1998 | Boyd et al. |
| 5,810,845 A | 9/1998 | Yoon |
| 5,814,052 A | 9/1998 | Nakao et al. |
| 5,823,946 A | 10/1998 | Chin |
| 5,827,216 A | 10/1998 | Igo et al. |
| 5,840,059 A | 11/1998 | March et al. |
| 5,855,586 A | 1/1999 | Habara et al. |
| 5,865,791 A | 2/1999 | Whayne et al. |
| 5,871,531 A | 2/1999 | Struble |
| 5,873,876 A | 2/1999 | Christy |
| 5,879,375 A | 3/1999 | Larson, Jr. et al. |
| 5,882,299 A | 3/1999 | Rastegar et al. |
| 5,893,869 A | 4/1999 | Barnhart et al. |
| 5,895,298 A | 4/1999 | Faupel et al. |
| 5,897,586 A | 4/1999 | Molina |
| 5,900,433 A | 5/1999 | Igo et al. |
| 5,906,579 A | 5/1999 | Vander Salm et al. |
| 5,906,620 A | 5/1999 | Nakao et al. |
| 5,908,429 A | 6/1999 | Yoon |
| 5,908,435 A | 6/1999 | Samuels |
| 5,910,124 A | 6/1999 | Rubin |
| 5,910,129 A | 6/1999 | Koblish et al. |
| 5,921,994 A | 7/1999 | Andreas et al. |
| 5,924,424 A | 7/1999 | Stevens et al. |
| RE36,269 E | 8/1999 | Wright |
| 5,941,819 A | 8/1999 | Chin |
| 5,957,936 A | 9/1999 | Yoon et al. |
| 5,961,440 A | 10/1999 | Schweich, Jr. et al. |
| 5,964,699 A | 10/1999 | Rullo et al. |
| 5,968,010 A | 10/1999 | Waxman et al. |
| 5,972,013 A | 10/1999 | Schmidt |
| 5,984,866 A | 11/1999 | Rullo et al. |
| 5,984,917 A | 11/1999 | Fleischman et al. |
| 5,991,668 A | 11/1999 | Leinders et al. |
| 5,997,525 A | 12/1999 | March et al. |
| 6,006,122 A | 12/1999 | Smits |
| 6,010,531 A | 1/2000 | Donlon et al. |
| 6,015,382 A | 1/2000 | Zwart et al. |
| 6,045,570 A | 4/2000 | Epstein et al. |
| 6,048,329 A | 4/2000 | Thompson et al. |
| 6,059,750 A | 5/2000 | Fogarty et al. |
| 6,067,942 A | 5/2000 | Fernandez |
| 6,071,281 A | 6/2000 | Burnside et al. |
| 6,081,738 A | 6/2000 | Hinohara et al. |
| 6,083,153 A | 7/2000 | Rullo et al. |

(56) References Cited

U.S. PATENT DOCUMENTS

| | | |
|---|---|---|
| 6,090,042 A | 7/2000 | Rullo et al. |
| 6,095,968 A | 8/2000 | Snyders |
| 6,110,170 A | 8/2000 | Taylor et al. |
| 6,120,431 A | 9/2000 | Magovern et al. |
| 6,132,438 A | 10/2000 | Fleischman et al. |
| 6,148,230 A | 11/2000 | KenKnight |
| 6,149,595 A | 11/2000 | Seitz et al. |
| 6,152,144 A | 11/2000 | Lesh et al. |
| 6,152,920 A | 11/2000 | Thompson et al. |
| 6,152,936 A | 11/2000 | Christy et al. |
| 6,155,968 A | 12/2000 | Wilk |
| 6,157,852 A | 12/2000 | Selmon et al. |
| 6,161,543 A | 12/2000 | Cox et al. |
| 6,162,195 A | 12/2000 | Igo et al. |
| 6,167,889 B1 | 1/2001 | Benetti |
| 6,199,556 B1 | 3/2001 | Benetti et al. |
| 6,200,303 B1 | 3/2001 | Verrior et al. |
| 6,206,004 B1 | 3/2001 | Schmidt et al. |
| 6,224,584 B1 | 5/2001 | March et al. |
| 6,231,518 B1 | 5/2001 | Grabek et al. |
| 6,237,605 B1 | 5/2001 | Vaska et al. |
| 6,241,667 B1 | 6/2001 | Vetter et al. |
| 6,258,021 B1 | 7/2001 | Wilk |
| 6,266,550 B1 | 7/2001 | Selmon et al. |
| 6,280,415 B1 | 8/2001 | Johnson |
| 6,283,127 B1 | 9/2001 | Sterman et al. |
| 6,290,674 B1 | 9/2001 | Roue et al. |
| 6,293,906 B1 | 9/2001 | Vanden Hoek et al. |
| 6,296,630 B1 | 10/2001 | Altman et al. |
| 6,311,692 B1 | 11/2001 | Vaska et al. |
| 6,311,693 B1 | 11/2001 | Sterman et al. |
| 6,314,962 B1 | 11/2001 | Vaska et al. |
| 6,314,963 B1 | 11/2001 | Vaska et al. |
| 6,319,201 B1 | 11/2001 | Wilk |
| 6,333,347 B1 | 12/2001 | Hunter et al. |
| 6,346,074 B1 | 2/2002 | Roth |
| 6,379,366 B1 | 4/2002 | Fleischman et al. |
| 6,423,051 B1 | 7/2002 | Kaplan et al. |
| 6,474,340 B1 | 11/2002 | Vaska et al. |
| 6,485,407 B2 | 11/2002 | Alferness et al. |
| 6,488,689 B1 | 12/2002 | Kaplan et al. |
| 6,494,211 B1 | 12/2002 | Boyd et al. |
| 6,551,303 B1 | 4/2003 | Van Tassel et al. |
| 6,561,969 B2 | 5/2003 | Frazier et al. |
| 6,592,552 B1 | 7/2003 | Schmidt |
| 6,610,055 B1 | 8/2003 | Swanson et al. |
| 6,610,072 B1 | 8/2003 | Christy et al. |
| 6,613,062 B1 | 9/2003 | Leckrone et al. |
| 6,632,229 B1 | 10/2003 | Yamanouchi |
| 6,652,555 B1 | 11/2003 | VanTassel et al. |
| 6,656,175 B2 | 12/2003 | Francischelli et al. |
| 6,666,861 B1 | 12/2003 | Grabek |
| 6,692,491 B1 | 2/2004 | Phan |
| 6,733,509 B2 | 5/2004 | Nobles et al. |
| 6,736,774 B2 | 5/2004 | Benetti et al. |
| 6,755,338 B2 | 6/2004 | Hahnen et al. |
| 6,786,898 B2 | 9/2004 | Guenst |
| 6,789,509 B1 | 9/2004 | Motsinger |
| 6,830,174 B2 | 12/2004 | Hillstead et al. |
| 6,830,576 B2 | 12/2004 | Fleischman et al. |
| 6,985,776 B2 | 1/2006 | Kane et al. |
| 7,011,671 B2 | 3/2006 | Welch |
| 7,041,111 B2 | 5/2006 | Chu |
| 7,056,294 B2 | 6/2006 | Khairkhahan et al. |
| 7,063,682 B1 | 6/2006 | Whayne et al. |
| 7,063,693 B2 | 6/2006 | Guenst |
| 7,175,619 B2 | 2/2007 | Koblish et al. |
| 7,186,214 B2 | 3/2007 | Ness |
| 7,207,988 B2 | 4/2007 | Leckrone et al. |
| 7,226,440 B2 | 6/2007 | Gelfand et al. |
| 7,226,458 B2 | 6/2007 | Kaplan et al. |
| 7,264,587 B2 | 9/2007 | Chin |
| 7,294,115 B1 | 11/2007 | Wilk |
| 7,297,144 B2 | 11/2007 | Fleischman et al. |
| 7,309,328 B2 | 12/2007 | Kaplan et al. |
| 7,318,829 B2 | 1/2008 | Kaplan et al. |
| 7,326,221 B2 | 2/2008 | Sakamoto et al. |
| 7,331,979 B2 | 2/2008 | Khosravi et al. |
| 7,473,260 B2 | 1/2009 | Opolski et al. |
| 7,608,091 B2 | 10/2009 | Goldfarb et al. |
| 7,610,104 B2 | 10/2009 | Kaplan et al. |
| 7,618,425 B2 | 11/2009 | Yamamoto et al. |
| 7,722,641 B2 | 5/2010 | van der Burg et al. |
| 7,736,347 B2 | 6/2010 | Kaplan et al. |
| 7,758,594 B2 * | 7/2010 | Lamson ............ A61B 17/0487 606/139 |
| 7,828,810 B2 | 11/2010 | Liddicoat et al. |
| 7,846,168 B2 | 12/2010 | Liddicoat et al. |
| 7,905,900 B2 | 3/2011 | Palermo et al. |
| 7,918,865 B2 | 4/2011 | Liddicoat et al. |
| 8,105,342 B2 | 1/2012 | Onuki et al. |
| 8,157,818 B2 | 4/2012 | Gartner et al. |
| 8,287,561 B2 | 10/2012 | Nunez et al. |
| 8,469,983 B2 | 6/2013 | Fung et al. |
| 8,636,767 B2 | 1/2014 | McClain |
| 8,715,302 B2 | 5/2014 | Ibrahim et al. |
| 8,721,663 B2 | 5/2014 | Kaplan et al. |
| 8,771,297 B2 | 7/2014 | Miller et al. |
| 8,795,297 B2 | 8/2014 | Liddicoat et al. |
| 8,795,310 B2 | 8/2014 | Fung et al. |
| 8,814,778 B2 | 8/2014 | Kiser et al. |
| 8,932,276 B1 | 1/2015 | Morriss et al. |
| 8,961,543 B2 | 2/2015 | Friedman et al. |
| 8,974,473 B2 | 3/2015 | Kaplan et al. |
| 8,986,278 B2 | 3/2015 | Fung et al. |
| 8,986,325 B2 | 3/2015 | Miller et al. |
| 8,996,133 B2 | 3/2015 | Kaplan et al. |
| 9,089,324 B2 | 7/2015 | McCaw et al. |
| 9,186,174 B2 | 11/2015 | Krishnan et al. |
| 9,198,664 B2 | 12/2015 | Fung et al. |
| 9,198,683 B2 | 12/2015 | Friedman et al. |
| 9,271,819 B2 | 3/2016 | Liddicoat et al. |
| 9,339,295 B2 | 5/2016 | Fung et al. |
| 9,408,608 B2 | 8/2016 | Clark et al. |
| 9,486,281 B2 | 11/2016 | Fung et al. |
| 9,498,206 B2 | 11/2016 | Fung et al. |
| 9,498,223 B2 | 11/2016 | Miller et al. |
| 9,522,006 B2 | 12/2016 | Liddicoat et al. |
| 9,724,105 B2 | 8/2017 | Kaplan et al. |
| 9,936,956 B2 | 4/2018 | Fung et al. |
| 10,045,784 B2 | 8/2018 | Friedman et al. |
| 10,130,369 B2 | 11/2018 | Fung et al. |
| 10,716,571 B2 | 7/2020 | Fung et al. |
| 2001/0025132 A1 | 9/2001 | Alferness et al. |
| 2002/0017306 A1 | 2/2002 | Cox et al. |
| 2002/0022860 A1 | 2/2002 | Borillo et al. |
| 2002/0049457 A1 | 4/2002 | Kaplan et al. |
| 2002/0058925 A1 | 5/2002 | Kaplan et al. |
| 2002/0062136 A1 | 5/2002 | Hillstead et al. |
| 2002/0068970 A1 | 6/2002 | Cox et al. |
| 2002/0103492 A1 | 8/2002 | Kaplan et al. |
| 2002/0107531 A1 | 8/2002 | Schreck et al. |
| 2002/0111636 A1 | 8/2002 | Fleischman et al. |
| 2002/0111637 A1 | 8/2002 | Kaplan et al. |
| 2002/0147456 A1 | 10/2002 | Diduch et al. |
| 2003/0014049 A1 | 1/2003 | Koblish et al. |
| 2003/0024537 A1 | 2/2003 | Cox et al. |
| 2003/0045900 A1 | 3/2003 | Hahnen et al. |
| 2003/0069577 A1 | 4/2003 | Vaska et al. |
| 2003/0083542 A1 | 5/2003 | Alferness et al. |
| 2003/0083674 A1 | 5/2003 | Gibbens, III |
| 2003/0109863 A1 | 6/2003 | Francischelli et al. |
| 2003/0120264 A1 | 6/2003 | Lattouf |
| 2003/0158464 A1 | 8/2003 | Bertolero |
| 2003/0181942 A1 | 9/2003 | Sutton et al. |
| 2003/0187460 A1 | 10/2003 | Chin et al. |
| 2003/0236535 A1 | 12/2003 | Onuki et al. |
| 2004/0030335 A1 | 2/2004 | Zenati et al. |
| 2004/0034347 A1 | 2/2004 | Hall et al. |
| 2004/0044361 A1 | 3/2004 | Frazier et al. |
| 2004/0049210 A1 | 3/2004 | VanTassel et al. |
| 2004/0059352 A1 | 3/2004 | Burbank et al. |
| 2004/0064138 A1 | 4/2004 | Grabek |
| 2004/0068267 A1 | 4/2004 | Harvie et al. |

(56) References Cited

U.S. PATENT DOCUMENTS

| | | |
|---|---|---|
| 2004/0078069 A1 | 4/2004 | Francischelli et al. |
| 2004/0102804 A1 | 5/2004 | Chin |
| 2004/0106918 A1 | 6/2004 | Cox et al. |
| 2004/0111101 A1 | 6/2004 | Chin |
| 2004/0116943 A1 | 6/2004 | Brandt et al. |
| 2004/0158127 A1 | 8/2004 | Okada |
| 2004/0162579 A1 | 8/2004 | Foerster |
| 2004/0225212 A1 | 11/2004 | Okerlund et al. |
| 2004/0225300 A1 | 11/2004 | Goldfarb et al. |
| 2004/0243176 A1 | 12/2004 | Hahnen et al. |
| 2004/0260273 A1 | 12/2004 | Wan |
| 2005/0033280 A1 | 2/2005 | Francischelli et al. |
| 2005/0033287 A1 | 2/2005 | Sra |
| 2005/0033321 A1 | 2/2005 | Fleischman et al. |
| 2005/0043743 A1 | 2/2005 | Dennis |
| 2005/0043745 A1 | 2/2005 | Alferness et al. |
| 2005/0080454 A1 | 4/2005 | Drews et al. |
| 2005/0085843 A1 | 4/2005 | Opolski et al. |
| 2005/0107824 A1 | 5/2005 | Hillstead et al. |
| 2005/0149068 A1 | 7/2005 | Williams et al. |
| 2005/0149069 A1 | 7/2005 | Bertolero et al. |
| 2005/0154376 A1 | 7/2005 | Riviere et al. |
| 2005/0165466 A1 | 7/2005 | Morris et al. |
| 2005/0256532 A1 | 11/2005 | Nayak et al. |
| 2006/0004323 A1 | 1/2006 | Chang et al. |
| 2006/0004388 A1 | 1/2006 | Whayne et al. |
| 2006/0009715 A1 | 1/2006 | Khairkhahan et al. |
| 2006/0020162 A1 | 1/2006 | Whayne et al. |
| 2006/0020271 A1 | 1/2006 | Stewart et al. |
| 2006/0020336 A1 | 1/2006 | Liddicoat |
| 2006/0034930 A1 | 2/2006 | Khosravi et al. |
| 2006/0095066 A1 | 5/2006 | Chang et al. |
| 2006/0100545 A1 | 5/2006 | Ayala et al. |
| 2006/0200169 A1 | 9/2006 | Sniffin |
| 2006/0212045 A1 | 9/2006 | Schilling et al. |
| 2006/0247672 A1 | 11/2006 | Vidlund et al. |
| 2006/0253128 A1 | 11/2006 | Sekine et al. |
| 2007/0010829 A1 | 1/2007 | Nobles et al. |
| 2007/0016228 A1 | 1/2007 | Salas |
| 2007/0027456 A1 | 2/2007 | Gartner et al. |
| 2007/0038229 A1 | 2/2007 | de la Torre |
| 2007/0060951 A1 | 3/2007 | Shannon |
| 2007/0083082 A1 | 4/2007 | Kiser et al. |
| 2007/0083225 A1 | 4/2007 | Kiser et al. |
| 2007/0083232 A1 | 4/2007 | Lee |
| 2007/0088369 A1 | 4/2007 | Shaw et al. |
| 2007/0100405 A1 | 5/2007 | Thompson et al. |
| 2007/0135822 A1 | 6/2007 | Onuki et al. |
| 2007/0149988 A1 | 6/2007 | Michler et al. |
| 2007/0156217 A1 | 7/2007 | Kaplan et al. |
| 2007/0156220 A1 | 7/2007 | Kaplan et al. |
| 2007/0179345 A1 | 8/2007 | Santilli |
| 2007/0249991 A1 | 10/2007 | Whayne et al. |
| 2007/0260278 A1 | 11/2007 | Wheeler et al. |
| 2007/0270637 A1 | 11/2007 | Takemoto et al. |
| 2007/0270891 A1 | 11/2007 | McGuckin, Jr. |
| 2008/0009843 A1 | 1/2008 | de la Torre |
| 2008/0015406 A1 | 1/2008 | Dlugos et al. |
| 2008/0033241 A1 | 2/2008 | Peh et al. |
| 2008/0033457 A1 | 2/2008 | Francischelli et al. |
| 2008/0039879 A1 | 2/2008 | Chin et al. |
| 2008/0065156 A1 | 3/2008 | Hauser et al. |
| 2008/0097489 A1 | 4/2008 | Goldfarb et al. |
| 2008/0154260 A1 | 6/2008 | Hoof |
| 2008/0228265 A1 | 9/2008 | Spence et al. |
| 2008/0245371 A1 | 10/2008 | Gruber |
| 2008/0269782 A1 | 10/2008 | Stefanchik et al. |
| 2008/0294174 A1 | 11/2008 | Bardsley et al. |
| 2008/0294175 A1 | 11/2008 | Bardsley et al. |
| 2008/0312664 A1 | 12/2008 | Bardsley et al. |
| 2009/0043317 A1 | 2/2009 | Cavanaugh et al. |
| 2009/0088728 A1 | 4/2009 | Dollar et al. |
| 2009/0088778 A1 | 4/2009 | Miyamoto et al. |
| 2009/0105753 A1 | 4/2009 | Greenhalgh et al. |
| 2009/0182326 A1 | 7/2009 | Zenati et al. |
| 2009/0196696 A1 | 8/2009 | Otsuka et al. |
| 2010/0069925 A1 | 3/2010 | Friedman et al. |
| 2010/0094314 A1 | 4/2010 | Hernlund |
| 2010/0174296 A1 | 7/2010 | Vakharia et al. |
| 2010/0191253 A1 | 7/2010 | Oostman et al. |
| 2010/0331820 A1 | 12/2010 | Giuseppe et al. |
| 2011/0034804 A1 | 2/2011 | Hubregtse et al. |
| 2011/0060350 A1 | 3/2011 | Powers et al. |
| 2011/0087270 A1 | 4/2011 | Penner et al. |
| 2011/0092997 A1 | 4/2011 | Kang |
| 2011/0106107 A1* | 5/2011 | Binmoeller ...... A61B 17/32056 606/139 |
| 2011/0112537 A1 | 5/2011 | Bernstein et al. |
| 2011/0245850 A1 | 10/2011 | van der Burg et al. |
| 2011/0282250 A1 | 11/2011 | Fung et al. |
| 2011/0295060 A1 | 12/2011 | Zenati et al. |
| 2012/0022558 A1 | 1/2012 | Friedman et al. |
| 2012/0109196 A1 | 5/2012 | McCaw et al. |
| 2012/0158022 A1 | 6/2012 | Kaplan et al. |
| 2012/0190927 A1 | 7/2012 | Uihlein |
| 2012/0209300 A1 | 8/2012 | Torrie |
| 2012/0330351 A1 | 12/2012 | Friedman et al. |
| 2014/0018831 A1 | 1/2014 | Kassab et al. |
| 2014/0171733 A1 | 6/2014 | Sternik |
| 2014/0222138 A1 | 8/2014 | Machold et al. |
| 2014/0276911 A1 | 9/2014 | Smith et al. |
| 2014/0330074 A1 | 11/2014 | Morriss et al. |
| 2014/0336572 A1 | 11/2014 | Heisel et al. |
| 2014/0336676 A1 | 11/2014 | Pong et al. |
| 2014/0364901 A1 | 12/2014 | Kiser et al. |
| 2014/0364907 A1 | 12/2014 | White et al. |
| 2015/0018853 A1 | 1/2015 | Friedman et al. |
| 2015/0025312 A1 | 1/2015 | de Canniere |
| 2015/0173765 A1 | 6/2015 | Friedman et al. |
| 2015/0119884 A1 | 4/2015 | Fung et al. |
| 2015/0157328 A1 | 6/2015 | Miller et al. |
| 2015/0182225 A1 | 7/2015 | Morejohn et al. |
| 2015/0190135 A1 | 7/2015 | Ibrahim et al. |
| 2015/0223813 A1 | 8/2015 | Willisamson et al. |
| 2015/0250482 A1 | 9/2015 | Slaughter et al. |
| 2015/0272618 A1 | 10/2015 | Fung et al. |
| 2015/0374380 A1 | 12/2015 | Miller et al. |
| 2016/0008001 A1 | 1/2016 | Winkler et al. |
| 2016/0008061 A1 | 1/2016 | Fung et al. |
| 2016/0106421 A1 | 4/2016 | Eliachar et al. |
| 2016/0120549 A1 | 5/2016 | Fung et al. |
| 2016/0235412 A1 | 8/2016 | Liddicoat et al. |
| 2016/0310144 A1 | 10/2016 | Kimura et al. |
| 2016/0310145 A1 | 10/2016 | Clark et al. |
| 2016/0317155 A1 | 11/2016 | Kimura et al. |
| 2016/0346028 A1 | 12/2016 | Rogers et al. |
| 2017/0209141 A1 | 7/2017 | Fung et al. |
| 2017/0245861 A1 | 8/2017 | Clark, III et al. |
| 2017/0290591 A1 | 10/2017 | Liddicoat et al. |
| 2017/0290592 A1 | 10/2017 | Miller et al. |
| 2017/0325819 A1 | 11/2017 | Kaplan et al. |
| 2018/0008342 A1 | 1/2018 | Ibrahim et al. |
| 2018/0085130 A1 | 3/2018 | Fung et al. |
| 2018/0092637 A1 | 4/2018 | Foerster |
| 2018/0310941 A1 | 11/2018 | Fung et al. |
| 2018/0325523 A1 | 11/2018 | Friedman et al. |

FOREIGN PATENT DOCUMENTS

| | | |
|---|---|---|
| EP | 0 598 219 B1 | 5/1994 |
| EP | 0 625 336 A2 | 11/1994 |
| EP | 1 010 397 A | 6/2000 |
| GB | 1 506 142 A | 4/1978 |
| JP | H-6-319742 A | 11/1994 |
| JP | 7-296645 A2 | 11/1995 |
| JP | 7-299073 A | 11/1995 |
| JP | 11-507262 A | 6/1999 |
| JP | 2001-120560 A | 5/2001 |
| JP | 2002-512071 A | 4/2002 |
| JP | 2002-540834 A | 12/2002 |
| JP | 2002-540901 A | 12/2002 |
| JP | 2003-225241 A | 8/2003 |
| JP | 2004-000601 A | 1/2004 |
| JP | 2005-110860 A | 4/2005 |

(56) References Cited

FOREIGN PATENT DOCUMENTS

| | | |
|---|---|---|
| JP | 2005-296645 A | 10/2005 |
| JP | 2005-531360 A | 10/2005 |
| JP | 2007-504886 A | 3/2007 |
| WO | WO-94/01045 A1 | 1/1994 |
| WO | WO-94/04079 A1 | 3/1994 |
| WO | WO-94/08514 A1 | 4/1994 |
| WO | WO-95/33408 A1 | 12/1995 |
| WO | WO-96/04854 A1 | 2/1996 |
| WO | WO-96/40356 A1 | 12/1996 |
| WO | WO-97/11644 A1 | 4/1997 |
| WO | WO-97/43957 A1 | 11/1997 |
| WO | WO-99/53845 A1 | 10/1999 |
| WO | WO-99/53987 A1 | 10/1999 |
| WO | WO-00/59383 A1 | 10/2000 |
| WO | WO-00/61202 A1 | 10/2000 |
| WO | WO-2004/002327 A1 | 1/2004 |
| WO | WO-2004/066828 A2 | 8/2004 |
| WO | WO-2004/066828 A3 | 8/2004 |
| WO | WO-2005/034767 A1 | 4/2005 |
| WO | WO-2005/034802 A2 | 4/2005 |
| WO | WO-2005/034802 A3 | 4/2005 |
| WO | WO-2006/096805 A1 | 9/2006 |
| WO | WO-2006/110734 A2 | 10/2006 |
| WO | WO-2006/115689 A1 | 11/2006 |
| WO | WO-2007/037516 A2 | 4/2007 |
| WO | WO-2007/037516 A3 | 4/2007 |
| WO | WO-2007/056502 A1 | 5/2007 |
| WO | WO-2008/017080 A2 | 2/2008 |
| WO | WO-2008/017080 A3 | 2/2008 |
| WO | WO-2008/036408 A2 | 3/2008 |
| WO | WO-2008/036408 A3 | 3/2008 |
| WO | WO-2008/091612 A2 | 7/2008 |
| WO | WO-2008/091612 A3 | 7/2008 |
| WO | WO-2008/121278 A2 | 10/2008 |
| WO | WO-2009/039191 A2 | 3/2009 |
| WO | WO-2009/094237 A1 | 7/2009 |
| WO | WO-2010/006061 A2 | 1/2010 |
| WO | WO-2010/006061 A3 | 1/2010 |
| WO | WO-2010/048141 A2 | 4/2010 |
| WO | WO-2010/048141 A3 | 4/2010 |
| WO | WO-2010/115030 A1 | 10/2010 |
| WO | WO-2012/170652 A1 | 12/2012 |

OTHER PUBLICATIONS

Al-Saady, N.M. et al. (1999). "Left Atrial Appendage: Structure, Function, and Role in Thromboembolism," *Heart* 82:547-554.

Albers, G.W. (Jul. 11, 1994). "Atrial Fibrillation and Stroke: Three New Studies, Three Remaining Questions," *Arch Intern Med* 154:1443-1448.

Alonso, M. et al. (Mar. 4, 2003). "Complications With Femoral Access in Cardiac Catheterization. Impact of Previous Systematic Femoral Angiography and Hemostasis With VasoSeal-Es® Collagen Plug," *Rev. Esp. Cardiol.* 56(6):569-577.

Aronow, W.S. et al. (Apr. 2009). "Atrial Fibrillation: The New Epidemic of the Age-ing World," *Journal of Atrial Fibrillation* 1(6):337-361.

Babaliaros, V.C. et al. (Jun. 3, 2008). "Emerging Applications for Transseptal Left Heart Catheterization: Old Techniques for New Procedures," *Journal of the American College of Cardiology* 51(22):2116-2122.

Bath, P.M.W. et al. (2005). "Current Status of Stroke Prevention in Patients with Atrial Fibrillation," *European Heart Journal Supplements* 7(Supplement C):C12-C18.

Benjamin, B.A. et al. (1994). "Effect of Bilateral Atrial Appendectomy on Postprandial Sodium Excretion in Conscious Monkeys," *Society for Experimental Biology and Medicine* 2006: 1 page.

Beygui, F. et al. (2005, e-pub. Oct. 21, 2005). "Multimodality Imaging of Percutaneous Closure of the Left Atrial Appendage," *Clinical Vignette*, 1 page.

Bisleri, G. et al. (Jun. 3, 2005). "Innovative Monolateral Approach for Closed-Chest Atrial Fibrillation Surgery," *The Annals of Thoracic Surgery* 80:e22-e25.

Björk, V.O. et al. (Aug. 1961). "Sequelae of Left Ventricular Puncture with Angiocardiography," *Circulation* 24:204-212.

Blackshear, J.L. et al. (Feb. 1996). "Appendage Obliteration to Reduce Stroke in Cardiac Surgical Patients With Atrial Fibrillation," *Ann. Thorac. Surg.* 61(2), 13 pages.

Blackshear, J.L. et al. (Oct. 1, 2003). "Thorascopic Extracardiac Obliteration of the Left Atrial Appendage for Stroke Risk Reduction in Atrial Fibrillation," *J. Am. Coll. Cardiol.* 42(7):1249-1252.

Bonanomi, G. et al. (Jan. 1, 2003). "Left Atrial Appendectomy and Maze," *Journal of the American College of Cardiology* 41(1):169-171.

Bonow, R.O. et al. (1998). "Guidelines for the Management of Patients With Valvular Heart Disease: Executive Summary: A Report of the American College of Cardiology/American Heart Association Task Force on Practice Guidelines (Committee on Management of Patients With Valvular Heart Disease)," *Journal of the American Heart Association* 98:1949-1984.

Botham, R.J. et al. (May 1959). "Pericardial Tamponade Following Percutaneous Left Ventricular Puncture," *Circulation* 19:741-744.

Brock, R. et al. (1956). "Percutaneous Left Ventricular Puncture in the Assessment of Aortic Stenosis," *Thorax* 11:163-171.

Burke, R.P. et al. (1992). "Improved Surgical Approach to Left Atrial Appendage Aneurysm," *Journal of Cardiac Surgery* 7(2):104-107.

Canaccord Adams (Aug. 11, 2008). "A-Fib: Near a Tipping Point," 167 pages.

Chung, M.K. (Jul. 2003). "Current Clinical Issues in Atrial Fibrillation," *Cleveland Clinic Journal of Medicine* 70(Supp. 3):S6-S11.

Coffin, L.H. (Jun. 1985). "Use of the Surgical Stapler to Obliterate the Left Atrial Appendage," *Surgery, Gynecology & Obstetric* 160:565-566.

Connolly, S.J. (Sep. 7, 1999). "Preventing Stroke in Atrial Fibrillation: Why Are So Many Eligible Patients Not Receiving Anticoagulant Therapy?" *Canadian Medical Association* 161(5):533-534.

Costa, R. et al. (2006). "Bi-Atrial Subxiphoid Epicardial Pacemaker in Superior Vena Cava Syndrome," *Arq. Bras. Cardiol.* 87:e45-e47.

Cox, J.L. et al. (Apr. 1991). "The Surgical Treatment of Atrial Fibrillation: IV. Surgical Technique," *J. Thorac. Cardiovasc. Surg.* 101(4):584-592.

Cox, J.L. et al. (Aug. 1995). "Modification of the Maze Procedure for Atrial Flutter and Atrial Fibrillation I. Rationale and Surgical Results," *J. Thorac. Cardiovasc. Surg.* 110(2):473-484.

Cox, J.L. et al. (Aug. 1995). "Modification of the Maze Procedure for Atrial Flutter and Atrial Fibrillation II. Surgical Technique of the Maze III Procedure," *J. Thorac. Cardiovasc. Surg.* 110(2):485-495.

Cox, J.L. et al. (Nov. 1999). "Impact of the Maze Procedure on the Stroke Rate in Patients with Atrial Fibrillation," *J. Thorac. Cardiovasc. Surg.* 118:833-840.

Cox, J.L. et al. (2004). "The Role of Surgical Intervention in the Management of Atrial Fibrillation," *Texas Heart Institute Journal* 31(3):257-265.

Crystal, E. et al. (Jan. 2003). "Left Atrial Appendage Occlusion Study (LAAOS): A Randomized Clinical Trial of Left Atrial Appendage Occlusion During Routine Coronary Artery Bypass Graft Surgery for Long-term Stroke Prevention," *Am Heart J* 145(1):174-178.

D'Avila, A. et al. (Apr. 2003). "Pericardial Anatomy for the Interventional Electrophysiologist," *Journal of Cardiovascular Electrophysiology* 14(4):422-430.

D'Avila, A. et al. (Nov. 2007). "Experimental Efficacy of Pericardial Instillation of Anti-inflammatory Agents During Percutaneous Epicardial Catheter Ablation to Prevent Postprocedure Pericarditis," *Journal of Cardiovascular Electrophysiology* 18(11):1178-1183.

Demaria, A.N. et al. (Dec. 17, 2003). "Highlights of the Year JACC 2003," *Journal of the American College of Cardiology* 42(12):2156-2166.

Deneu, S. et al. (Jul. 11, 1999). "Catheter Entrapment by Atrial Suture During Minimally Invasive Port-access Cardiac Surgery," *Canadian Journal of Anesthesia* 46(10):983-986.

Deponti, R. et al. (Mar. 7, 2006). "Trans-Septal Catheterization in the Electrophysiology Laboratory: Data From a Multicenter Survey Spanning 12 Years," *Journal of the American College of Cardiology* 47(5):1037-1042.

(56) References Cited

OTHER PUBLICATIONS

Donal, E. et al. (Sep. 2005). "The Left Atrial Appendage, a Small, Blind-Ended Structure: A Review of Its Echocardiographic Evaluation and Its Clinical Role," *Chest* 128(3):1853-1862.

Donnino, R. et al. (2007). "Left Atrial Appendage Thrombus Outside of a 'Successful' Ligation," *European Journal of Echocardiography* pp. 1-2.

Dullum, M.K.C. et al. (1999). "Xyphoid MIDCAB: Report of the Technique and Experience with a Less Invasive MIDCAB Procedure," *Heart Surgery Forum* 2(1):77-81.

Feinberg, W.M. et al. (Mar. 13, 1995). "Prevalence, Age Distribution, and Gender of Patients With Atrial Fibrillation," *Arch Intern Med* 155:469-473.

Fieguth, H.G. et al. (1997). "Inhibition of Atrial Fibrillation by Pulmonary Vein Isolation and Auricular Resection—Experimental Study in a Sheep Model," *European Journal of Cardio-Thoracic Surgery* 11:714-721.

Fisher, D.C. et al. (Dec. 1998). "Large Gradient Across a Partially Ligated Left Atrial Appendage," *Journal of the American Society of Echocardiography* 11(12):1163-1165.

Friberg, L. et al. (2006). "Stroke Prophylaxis in Atrial Fibrillation: Who Gets it and Who Does Not?" *European Heart Journal* 27:1954-1964.

Friedman, P.A. et al. (Aug. 2009). "Percutaneous Epicardial Left Atrial Appendage Closure: Preliminary Results of an Electrogram Guided Approach," *Journal of Cardiovascular Electrophysiology* 20(8):908-915.

Fuster, V. et al. (Oct. 2001). "ACC/AHA/ESC Guidelines for the Management of Patients with Atrial Fibrillation," *European Heart Journal* 22(20):1852-1923.

Garcia-Fernandez, M.A. et al. (Oct. 1, 2003). "Role of Left Atrial Appendage Obliteration in Stroke Reduction in Patients With Mitral Valve Prosthesis," *Journal of the American College of Cardiology* 42(7):1253-1258.

Gardiner, G.A. Jr. et al. (Apr. 1986). "Complications of Transluminal Angioplasty," *Radiology* 159:201-208.

Gillinov, A.M. (2007). "Advances in Surgical Treatment of Atrial Fibrillation," *Stroke* 38(part 2):618-623.

Gilman, R.A. et al. (Apr. 1963). "Direct Left Ventricular Puncture," *California Medicine* 98(4):200-203.

Goodwin, W.E. et al. (Nov. 1950). "Translumbar Aortic Puncture and Retrograde Catheterization of the Aorta in Aortography and Renal Arteriography," *Annals of Surgery* 132(5):944-958.

Gottlieb, L.K. et al. (Sep. 12, 1994). "Anticoagulation in Atrial Fibrillation," *Arch Intern Med.* 154:1945-1953.

Graffigna, A. et al. (1993). "Surgical Treatment of Wolff-Parkinson-White Syndrome: Epicardial Approach Without the Use of Cardiopulmonary Bypass," *J. Card. Surg.* 8:108-116.

Haissaguerre, M. et al. (Nov. 2005). "Catheter Ablation of Long-Lasting Persistent Atrial Fibrillation: Clinical Outcome and Mechanisms of Subsequent Arrhythmias," *Journal of Cardiovascular Electrophysiology* 16(11):1138-1147.

Halperin, J.L. et al. (Aug. 1988). "Atrial Fibrillation and Stroke: New Ideas, Persisting Dilemmas," *Journal of the American Heart Association* 19(8):937-941.

Halperin, J.L. et al. (Oct. 1, 2003). "Obliteration of the Left Atrial Appendage for Prevention of Thromboembolism," *Journal of the American College of Cardiology* 42(7):1259-1261.

Hammill, S.C. (May 2006). "Epicardial Ablation: Reducing the Risks," *J. Cardiovasc. Electrophysiol.* 17:550-552.

Hara, H. et al. (Jan. 2008). "Percutaneous Left Atrial Appendage Obliteration," *JACC: Cardiovascular Imagin* 1(1):92-93.

Hart, R.G. et al. (Nov. 2, 1999). "Atrial Fibrillation and Thromboembolism: A Decade of Progress in Stroke Prevention," *Annals of Internal Medicine* 131(9):688-695.

Hart, R.G. et al. (2001). "Atrial Fibrillation and Stroke: Concepts and Controversies," *Stroke* 32:803-808.

Hart, R.G. (Sep. 11, 2003). "Atrial Fibrillation and Stroke Prevention," *The New England Journal of Medicine* 349(11):1015-1016.

Healey, J.S. et al. (Oct. 2003). "Surgical Closure of the Left Atrial Appendage for the Prevention of Stroke: A Randomized Pilot Trial of Safety and Efficacy (The Left Atrial Appendage Occlusion Study—LAAOS)," presented at the Canadian Cardiovascular Congress 2003, Toronto, Canada, Abstract No. 666, 2 pages.

Healey, J.S. et al. (Aug. 2005). "Left Atrial Appendage Occlusion Study (LAAOS): Results of a Randomized Controlled Pilot Study of Left Atrial Appendage Occlusion During Coronary Bypass Surgery in Patients At Risk for Stroke," *American Heart Journal* 150(2):288-293.

Hein, R. et al. (2005). "Patent Foramen Ovale and Left Atrial Appendage: New Devices and Methods for Closure," *Pediatric Cardiology* 26(3):234-240.

Heist, E.K. et al. (Nov. 2006). "Analysis of the Left Atrial Appendage by Magnetic Resonance Angiography in Patients with Atrial Fibrillation," *Heart Rhythm* 3(11):1313-1318.

Ho, I. et al. (Apr. 24, 2007). "Percutaneous Epicardial Mapping Ablation of a Posteroseptal Accessory Pathway," *Circulation* 115:e418-e421.

Ho, S.Y. et al. (Nov. 1999). "Anatomy of the Left Atrium: Implications for Radiofrequency Ablation of Atrial Fibrillation," *Journal of Cardiovascular Electrophysiology* 10(11):1525-1533.

Hoit, B.D. et al. (Jan. 1993). "Altered Left Atrial Compliance After Atrial Appendectomy. Influence on Left Atrial and Ventricular Filling," *Circulation Research* 72(1):167-175.

Inoue, Y. et al. (Jul.-Aug. 1997). "Video Assisted Thoracoscopic and Cardioscopic Radiofrequency Maze Ablation," *Asaio Journal* 43(4):334-337, Abstract Only.

Jaïs, P. et al. (2003). "Radiofrequency Ablation for Atrial Fibrillation," *European Society of Cardiology* 5(Supplement H):H34-H39.

Johnson, W.D. et al. (2000). "The Left Atrial Appendage: Our Most Lethal Human Attachment! Surgical Implications," *Euro. J. Cardiothoracic. Surg.* 17:718-722.

Jongbloed, M.R.M. et al. (2005). "Clinical Applications of Intracardiac Echocardiography in Interventional Procedures," *Heart* 91:981-990.

Kamohara, K. et al. (Aug. 2006). "Evaluation of a Novel Device for Left Atrial Appendage Exclusion: The Second-generation Atrial Exclusion Device," *The Journal of Thoracic and Cardiovascular Surgery* 132(2):340-346.

Kanderian, A.S. et al. (2008). "Success of Surgical Left Atrial Appendage Closure: Assessment by Transesophageal Echocardiography," *Journal of the American College of Cardiology* 52(11):924-929.

Kato, H. et al. (Aug. 1, 1996). "Evaluation of Left Atrial Appendage Stasis in Patients With Atrial Fibrillation Using Transesophageal Echocardiography With an Intravenous Albumin-Contrast Agent," *The American Journal of Cardiology* 78:365-369.

Katz, E.S. et al. (Aug. 2000). "Surgical Left Atrial Appendage Ligation is Frequently Incomplete: A Transesophageal Echocardiographic Study," *Journal of the American College of Cardiology* 36(2):468-471.

Kenner, H.M. et al. (Dec. 1966). "Intrapericardial, Intrapleural, and Intracardiac Pressures During Acute Heart Failure in Dogs Studied without Thoracotomy," *Circulation Research* 19:1071-1079.

Kerut, E.K. et al. (Jul. 2008). "Anatomy of the Left Atrial Appendage," *Echocardiography* 25(6):669-673.

Khargi, K. et al. (2005). "Surgical Treatment of Atrial Fibrillation: A Systematic Review," *European Journal of Cardiothoracic Surgery* 27:258-265.

Kim, K.B. et al. (Jan. 1998). "Effect of the Cox Maze Procedure on the Secretion of Atrial Natriuretic Peptide," *J. Thorac. Cardiovasc. Surg.* 115(1):139-146; discussion 146-147.

Kistler, P.M. et al. (May 2007). "The Left Atrial Appendage: Not Just an Innocent Bystander," *J. Cardiovasc Electrophysiol* 18(5):465-466.

Klein, H. et al. (Apr. 1990). "The Implantable Automatic Cardioverter-Defibrillator," *Herz* 15(2):111-125, Abstract Only.

Kolb, C. et al. (Feb. 2004). "Incidence of Antitachycardia Therapy Suspension Due to Magnet Reversion in Implantable Cardioverter Defibrillators," *Pace* 27:221-223.

Krikorian, J.G. et al. (Nov. 1978). "Pericardiocentesis," *Am. J. Med.* 65(5):808-814.

(56) References Cited

OTHER PUBLICATIONS

Krum, D. et al. (2004). "Visualization of Remnants of the left Atrial Appendage Following Epicardial Surgical Removal," *Heart Rhythm* 1:249.

Lacomis, J.M. et al. (Oct. 2003). "Multi-Detector Row CT of the Left Atrium and Pulmonary Veins before Radio-frequency Catheter Ablation for Atrial Fibrillation," *Radio Graphics* 23:S35-S48.

Lacomis, J.M. et al. (2007, e-pub. Oct. 17, 2007). "Dynamic Multidimensional Imaging of the Human Left Atrial Appendage," *Europace* 9:1134-1140.

Lee, R. et al. (1999). "The Closed Heart MAZE: A Nonbypass Surgical Technique," *The Annals of Thoracic Surgery* 67:1696-1702.

Levinson, M.L. et al. (1998). "Minimally Invasive Atrial Septal Defect Closure Using the Subxyphoid Approach," *Heart Surg. Forum* 1(1):49-53, Abstract Only.

Lewis, D.R. et al. (1999). "Vascular Surgical Intervention for Complications of Cardiovascular Radiology: 13 Years' Experience in a Single Centre," *Ann. R. Coll. Surg. Engl.* 81:23-26.

Li, H. (2007). "Magnet Decoration, Beautiful but Potentially Dangerous for Patients with Implantable Pacemakers or Defibrillators," *Heart Rhythm* 4(1):5-6.

Lindsay, B.D. (1996). "Obliteration of the Left Atrial Appendage: A Concept Worth Testing," *The Annals of Thoracic Surgery* 61:515.

Lip, G.Y.H. et al. (Jun. 2001). "Thromboprophylaxis for Atrial Flutter," *European Heart Journal* 22(12):984-987.

Lustgarten, D.L. et al. (May/Jun. 1999). "Cryothermal Ablation: Mechanism of Tissue Injury and Current Experience in the Treatment of Tachyarrhythmias," *Progress in Cardiovascular Diseases* 41(6):481-498.

Macris, M. et al. (Jan. 1999). "Minimally Invasive Access of the Normal Pericardium: Initial Clinical Experience with a Novel Device," *Clin. Cardiol.* 22(Suppl. I):I-36-I-39.

Maisch, B. et al. (Jan. 1999). "Intrapreicardial Treatment of Inflammatory and Neoplastic Pericarditis Guided by Pericardioscopy and Epicardial Biopsy-Results from a Pilot Study," *Clin. Cardiol.* 22(Supp. I):I-17-I-22.

Mannam, A.P. et al. (Apr. 1, 2002). "Safety of Subxyphoid Pericardial Access Using a Blunt-Tip Needle," *The American Journal of Cardiology* 89:891-893.

Mattox, K.L. et al. (May 1997). "Newer Diagnostic Measure and Emergency Management," *Ches Surg Clin N Am.* 7(2):213-226, Abstract Only.

McCarthy, P.M. et al. (2008). "Epicardial Atrial Fibrillation Ablation," Chapter 23 in *Contemporary Cardiology: Atrial Fibrillation, From Bench to Bedside*, Natale, A. et al. eds., Humana Press,: Totowa, NJ, pp. 323-332.

McCaughan, J.J. Jr., et al. (Nov. 1957). "Aortography Utilizing Percutaneous Left Ventricular Puncture," located at <http://www.archsurg.com>, last visited on Apr. 7, 2009, 73:746-751, Abstract Only.

McClelland, R.R. (1978). "Congenital Aneurysmal Dilatation of the Left Auricle Demonstrated by Sequential Cardiac Blood-Pool Scintiscanning," *J. Nucl. Med.* 19(5):507-509.

Melo, J. et al. (Apr. 21, 2008). "Surgery for Atrial Fibrillation in Patients with Mitral Valve Disease: Results at Five Years from the International Registry of Atrial Fibrillation Surgery," *The Journal of Thoracic and Cardiovascular Surgery* 135(4):863-869.

Miller, P.S.J. et al. (Feb. 2005). "Are Cost Benefits of Anticoagulation for Stroke Prevention in Atrial Fibrillation Underestimated?" *Stroke* 36:360-366.

Miyasaka, Y. et al. (Jul. 11, 2006). "Secular Trends in Incidence of Atrial Fibrillation in Olmsted County, Minnesota, 1980 to 2000, and Implications on the Projections for Future Prevalence," *Circulation* 114:119-125.

Morris, J.J. Jr. (1979). "Transvenous versus Transthoracic Cardiac Pacing," Chapter 16 in *Cardiac Pacing: A Concise Guide to Clinical Practice*, pp. 239-245.

Mráz, T. et al. (Apr. 2007). "Role of Echocardiography in Percutaneous Occlusion of the left Atrial Appendage," *Echocardiography* 24(4):401-404.

Naclerio, E.A. et al. (1979). "Surgical Techniques for Permanent Ventricular Pacing," Chapter 10 in *Cardiac Pacing: A Concise Guide to Clinical Practice*, pp. 145-168.

Nakai, T. et al. (May 7, 2002). "Percutaneous Left Atrial Appendage Occlusion (PLAATO) for Preventing Cardioembolism: First Experience in Canine Model," *Circulation* 105:2217-2222.

Nakajima, H. et al. (2004). "Consequence of Atrial Fibrillation and the Risk of Embolism After Percutaneous Mitral Commissurotomy:The Necessity of the Maze Procedure," *The Annals of Thoracic Surgery* 78:800-806.

Odell, J.A. et al. (1996). "Thorascopic Obliteration of the Left Atrial Appendage: Potential for Stroke Reduction?" *Ann. Thorac. Surg.* 61:565-569.

O'Donnell, M. et al. (2005). "Emerging Therapies for Stroke Prevention in Atrial Fibrillation," *European Heart Journal* 7(Supplement C):C19-C27.

Omran, H. et al. (1997). "Left Atrial Appendage Function in Patients with Atrial Flutter," *Heart* 78:250-254.

Onalan, O. et al. (2005). "Nonpharmacologic Stroke Prevention in Atrial Fibrillation," *Expert Rev. Cardiovasc. Ther.* 3(4):619-633.

Onalan, O. et al. (2007). "Left Atrial Appendage Exclusion for Stroke Prevention in Patients With Nonrheumatic Atrial Fibrillation," *Stroke* 38(part 2):624-630.

Ostermayer, S. et al. (2003). "Percutaneous Closure of the Left Atrial Appendage," *Journal of Interventional Cardiology* 16(6):553-556.

Ota, T. et al. (2006). "Epicardial Atrial Ablation Using a Novel Articulated Robotic Medical Probe via a Percutaneous Subxiphoid Approach," *National Institute of Health* 1(6):335-340.

Ota, T. et al. (Oct. 2007). "Impact of Beating Heart left Atrial Ablation on Left-sided Heart Mechanics," *The Journal of Thoracic and Cardiovascular Surgery* 134:982-988.

Pennec, P.-Y. et al. (2003). "Assessment of Different Procedures for Surgical Left Atrial Appendage Exclusion," *The Annals of Thoracic Surgery* 76:2167-2168.

Perk, G. et al. (Aug. 2009). "Use of Real Time Three-Dimensional Transesophageal Echocardiography in Intracardiac Catheter Based Interventions," *J. Am Soc Echocardiogr* 22(8):865-882.

Pollick C. (Feb. 2000). "Left Atrial Appendage Myopathy," *Chest* 117(2):297-308.

Poulsen, T.S. et al. (Feb. 15, 2005). "Is Aspirin Resistance or Female Gender Associated With a High Incidence of Myonecrosis After Nonurgent Percutaneous Coronary Intervention?" *J. Am. Coll. Cardiol.* 45(4):635-636.

Reznik, G. et al. (Oct. 1992). "Percutaneous Endoscopic Implantation of Automatic Implantable Cardioverter/Defibrillator (AICD): An Animal Study of a New Nonthoracotomy Technique," *J. Laparoendosc. Surg.* 2(5):255-261, Abstract Only.

Robicsek, F. (1987). "Closed-Chest Decannulation of Transthoracically Inserted Aortic Balloon Catheter without Grafting," *Journal of Cardiac Surgery* 2(2):327-329.

Ross, J. Jr. et al. (Jun. 3, 2008). "Transseptal Left Heart Catheterization: A 50-Year Odyssey," *Journal of the American College of Cardiology* 51(22):2107-2115.

Rubin, D.N. et al. (Oct. 1, 1996). "Evaluation of Left Atrial Appendage Anatomy and Function in Recent-Onset Atrial Fibrillation by Transesophageal Echocardiography," *Am J Cardiol* 78:774-778.

Ruchat, P. et al. (2002). "Off-pump Epicardial Compartmentalization for Ablation of Atrial Fibrillation," *Interactive Cardio Vascular and Thoracic Surgery* 1:55-57.

Salzberg, S.P. et al. (2008). "Surgical Left Atrial Appendage Occlusion: Evaluation of a Novel Device with Magnetic Resonance Imaging," *European Journal of Cardiothoracic Surgery* 34:766-770.

Sapp, J. et al. (Dec. 2001). "Electrophysiology and Anatomic Characterization of an Epicardial Accessory Pathway," *Journal of Cardiovascular Electrophysiology* 12(12):1411-1414.

(56) References Cited

OTHER PUBLICATIONS

Scharf, C. et al. (2005). "Catheter Ablation for Atrial Fibrillation: Pathophysiology, Techniques, Results and Current Indications," *Continuous Medical Education* 8:53-61.

Scherr, D. et al. (Apr. 2009). "Incidence and Predictors of left Atrial Thrombus Prior to Catheter Ablation of Atrial Fibrillation," *Journal of Cardiovascular Electrophysiology* 20(4):379-384.

Schmidt, H. et al. (Sep. 2001). "Prevalence of Left Atrial Chamber and Appendage Thrombi in Patients With Atrial Flutter and Its Clinical Significance," *Journal of the American College of Cardiology* 38(3):778-784.

Schneider, B. et al. (2005, e-pub. Aug. 22, 2005). "Surgical Closure of the Left Atrial Appendage—A Beneficial Procedure?" *Cardiology* 104:127-132.

Schweikert, R.A. et al. (Sep. 16, 2003). "Percutaneous Pericardial Instrumentation for Endo-Epicardial Mapping of Previously Failed Ablation," *Circulation* 108:1329-1335.

Schweikert, R.A. et al. (2005). "Epicardial Access: Present and Future Applications for Interventional Electrophysiologists," Chapter 25 in New Arrhythmia Technolgies, Wang, P.J. ed., Blackwell Publishing, pp. 242-256.

Seferovic, P. et al. (Jan. 1999). "Initial Clinical Experience with the PerDUCER® Device: Promising New Tool in the Diagnosis and Treatment of Pericardial Disease," *Clin. Cardiol.* 22(Supp I):I-30-I-35.

Sengupta, P.P. et al. (2005). "Transoesophageal Echocardiography," *Heart* 91:541-547.

Sharada, K. et al. (2005). "Non-Surgical Transpericardial Catheter Ablation of Post-Infarction Ventricular Tachycardia," *Indian Heart J* 57:58-61.

Sievert, H. et al. (Apr. 23, 2002). "Percutaneous Left Atrial Appendage Transcatheter Occlusion to Prevent Stroke in High-Risk Patients With Atrial Fibrillation," *Circulation* 105:1887-1889.

Singer, D.E. et al. (Sep. 2004). "Antithrombotic Therapy in Atrial Fibrillation: The Seventh ACCP Conference on Antithrombotic and Thrombolytic Therapy," *Chest* 126(3):429S-456S.

Smith, P.W. et al. (Nov. 1956). "Diagnosis of Mitral Regurgitation by Cardioangiography," *Circulation* 14:847-853.

Soejima, K. et al. (2004). "Subxiphoid Surgical Approach for Epicardial Catheter-Based Mapping and Ablation in Patients With Prior Cardiac Surgery or Difficult Pericardial Access," *Circulation* 110:1197-1201.

Sosa, E. et al. (1996). "A New Technique to Perform Epicardial Mapping in the EP Laboratory," *J. Cardiovasc. Electrophysiol.* 7(6):531-536.

Sosa, E. et al. (Mar. 1998). "Endocardial and Epicardial Ablation Guided by Nonsurgical Transthoracic Epicardial Mapping to Treat Recurrent Ventricular Tachycardia," *J. Cardiovasc. Elecytophysiol.* 9(3):229-239.

Sosa, E. et al. (Dec. 14, 1999). "Different Ways of Approaching the Normal Pericardial Space," *Circulation* 100(24):e115-e116.

Sosa, E. et al. (Jul. 15, 2002). "Gaining Access to the Pericardial Space," *The American Journal of Cardiology* 90:203-204.

Sosa, E. et al. (Apr. 2005). "Epicardial Mapping and Ablation Techniques to Control Centricular Tachycardia," *Journal of Cardiovasc. Electrphsiol.* 16(4):449-452.

Sparks, P.B. et al. (2001). "Is Atrial Flutter a Risk Factor for Stroke?" *Journal of the American College of Cardiology* 38(3):785-788.

Spodick, D.H. (Nov. 1970). "Medical History of the Pericardium," *The American Journal of Cardiology* 26:447-454.

Stewart, J.M. et al. (Apr. 1992). "Bilateral Atrial Appendectomy Abolishes Increased Plasma Atrial Natriuretic Peptide Release and Blunts Sodium and Water Excretion During Volume Loading in Conscious Dogs," *Circulation Research* 70(4):724-732.

Stewart, S. (1974). "Placement of the Sutureless Epicardial Pacemaker Lead by the Subxiphoid Approach," *Ann. Of Thoracic Surg.* 18(3):308-313.

Stoddard, M.F. et al. (1995). "Left Atrial Appendage Thrombus is not Uncommon in Patients with Acute Atrial Fibrillation and a Recent Embolic Event: A Transesophageal Echocardiographic Study," *J. Am. Coll. Cardiol.* 25:452-459, Abstract Only.

Stokes, K. (Jun. 1990). "Implantable Pacing Lead Technology," *IEEE Engineering in Medicine and Biology* pp. 43-49.

Stöllberger, C. et al. (2000). "Is the Left Atrial Appendage Our Most Lethal Attachment?" *European Journal of Cardio-Thoracic Surgery* 18:625-626.

Stöllberger, C. et al. (Dec. 2003). "Elimination of the Left Atrial Appendage to Prevent Stroke or Embolism?: Anatomic, Physiologic, and Pathophysiologic Considerations," 124(6):2356-2362.

Stöllberger, C. et al. (2006). "Stroke Prevention by Means of Epicardial Occlusion of the Left Atrial Appendage," *Journal of Thoracic and Cardiovascular Surgery* 132(1):207-208.

Stöllberger, C. et al. (2007). "Arguments Against Left Atrial Appendage Occlusion for Stroke Prevention," *Stroke* 38:e77.

Stöllberger, C. et al. (2007). "Leave the Left Atrial Appendage Untouched for Stroke Prevention!" *Journal of Thoracic and Cardiovascular Surgery* 134(2):549-550.

Su, P. et al. (Sep. 2008, e-pub. May 8, 2007). "Occluding the Left Atrial Appendage: Anatomical Considerations," *Heart* 94(9):1166-1170.

Subramanian, V.A. (Jun. 1997). "Less Invasive Arterial CABG on a Beating Heart," *Ann. Thorac. Surg.* 63(6 Suppl.):S68-S71.

Subramanian, V.A. et al. (Dec. 1997). "Minimally Invasive Direct Coronary Artery Bypass Grafting: two-Year Clinical Experience," *Ann. Thorac. Surg.* 64(6):1648-1653, Abstract Only.

Suehiro, S. et al. (1996). "Echocardiography-Guided Pericardiocentesis With a Needle Attached to a Probe," *Ann. Thoracic Surg.* 61:741-742.

Sun, F. et al. (Feb. 2006). "Subxiphoid Access to Normal Pericardium with Micropuncture Set: Technical Feasibility Study in Pigs," *Radiology* 238(2):719-724.

Szili-Torok, T. et al. (2001). "Transseptal Left heart Catheterisation Guided by Intracardiac Echocardiography," *Heart* 86:e11-e15.

Tabata, T. et al. (Feb. 1, 1998). "Role of Left Atrial Appendage in left Atrial Reservoir Function as Evaluated by Left Atrial Appendage Clamping During Cardiac Surgery," *The American Journal of Cardiology* 81:327-332.

Tomar, M. et al. (Jul.-Aug. 2006). "Transcatheter Closure of Fossa Ovalis Atrial Septal Defect: A Single Institutional Experience," *Indian Heart Journal* 58(4):325-329.

Troughton, R.W. et al. (Feb. 28, 2004). "Pericarditis," *The Lancet* 363:717-727.

Ulicny K.S. et al. (Jun. 1992). "Conjoined Subrectus Pocket for Permanent Pacemaker Placement in the Neonate," *Ann Thorac Surg.* 53(6):1130-1131, Abstract Only.

Valderrabano, M. et al. (Sep. 2004). "Percutaneous Epicardial Mapping During Ablation of Difficult Accessory Pathways as an Alternative to Cardiac Surgery," *Heart Rhythm* 1(3):311-316.

Von Korn, H. et al. (2006). "Simultaneous Combined Interventional Percutaneous Left Atrial Auricle and Atrial Septal Defect Closure," *Heart* 92:1462.

Wang, T.J. et al. (Aug. 27, 2003). "A Risk Score for Predicting Stroke or Death in Individuals With New-Onset Atrial Fibrillation in the Community," *American Medical Association* 290(8):1049-1056.

Watkins, L. et al. (Nov. 1982). "Implantation of the Automatic Defibrillator: The Subxiphoid Approach," *Ann. of Thoracic Surg.* 34(5):515-520.

W.L. Gore & Associates (Aug. 11, 2006). "Gore Helex™ Septal Occluder," located at <http://www.fda.gov/cdrh/pdf5/p050006a.pdf>, last visited on Jun. 14, 2007, 3 pages.

Wolber, T. et al. (Jan. 2007). "Potential Interference of Small Neodymium Magnets with Cardiac pacemakers and Implantable Cardioverter-defibrillators," *Heart Rhythm* 4(1):1-4.

Wolf, P.A. et al. (Oct. 1978). "Epidemiologic Assessment of Chronic Atrial Fibrillation and Risk of Stroke: The Fiamingham Study," *Neurology* 28:973-977.

Wolf, P.A. et al. (Aug. 1991). "Atrial Fibrillation as an Independent Risk Factor for Stroke: The Framingham Study," *Stroke* 22(8):983-988.

(56) References Cited

OTHER PUBLICATIONS

Wolf, P.A. et al. (Feb. 9, 1998). "Impact of Atrial Fibrillation on Mortality, Stroke, and Medical Costs," *Arch Intern Med* 158:229-234.
Wong, J.W.W. et al. (2006). "Impact of Maze and Concomitant Mitral Valve Surgery on Clinical Outcomes," *The Annals of Thoracic Surgery* 82:1938-1947.
Wongcharoen, W. et al. (Sep. 2006). "Morphologic Characteristics of the Left Atrial Appendage, Roof, and Septum: Implications for the Ablation of Atrial Fibrillation," *Journal of Cardiovascular Electrophysiology* 17(9):951-956.
Wood, M.A. (Jan. 2006). "Percutaneous Pericardial Instrumentation in the Electrophysiology Laboratory: A Case of Need," *Heart Rhythm* 3(1):11-12.
Wudel, J.H. et al. (Apr. 3, 2008). "Video-Assisted Epicardial Ablation and left Atrial Appendage Exclusion for Atrial Fibrillation: Extended Follow-Up," *The Annals of Thoracic Surgery* 85:34-38.
Wyse, D.G. et al. (Dec. 5, 2002). "Of 'Left Atrial Appendage Amputation, Ligation, or Occlusion in Patients with Atrial Fibrillation'," *N Engl J Med* 347(23):1825-1833, Abstract Only.
Yamada, Y. et al. (Aug. 2006). "Video-Assisted Thoracoscopy to Treat Atrial Tachycardia Arising from Left Atrial Appendage," *Journal of Cardiovascular Electrophysiology* 17(8):895-898.
Zapolanski, A. et al. (May 2008). "Safe and Complete Exclusion of the left Atrial Appendage, A Simple Epicardial Approach," *Innovations* 3(3):161-163.
Zenati, M.A. et al. (Sep. 2003). "Left Heart Pacing Lead Implantation Using Subxiphoid Videopericardioscopy," *Journal of Cardiovascular Electrophysiology* 14(9):949-953.
Zenati, M.A. et al. (2004). "Mechanical Function of the Left Atrial Appendage Following Epicardial Bipolar Radiofrequency Ablation," *Cardiothoracic Techniques and Technologies X*, Abstract 121A, p. 176.
Zenati, M.A. et al. (2005). "Modification of the Left Atrial Appendage," Chapter 12 in Innovative Management of Atrial Fibrillation, Schwartzman, David ed., Blackwell Science Ltd., 5 pages.
Extended European Search Report dated Jul. 10, 2015, for European Patent Application No. 15153029.2, filed on Mar. 25, 2008, 6 pages.
Extended European Search Report dated Feb. 10, 2017, for EP Application No. 10 759 425.1, filed on Apr. 1, 2010, 7 pages.
Extended European Search Report dated Nov. 15, 2018, for EP Application No. 16769732.5 , 7 pages.
International Search Report dated Feb. 27, 2007, for PCT Application No. PCT/US2008/003938, filed on Mar. 25, 2008, 5 pages.
International Search Report dated Jun. 1, 2010, for PCT Application No. PCT/US2010/029668, filed on Apr. 1, 2010, 2 pages.
International Search Report dated Jun. 24, 2016, for PCT Application No. PCT/US2016/024117, filed on Mar. 24, 2016, 2 pages.
Invitation to Pay Additional Fees mailed May 31, 2016, for PCT Application No. PCT/US16/24103; 2 pages.
Written Opinion of the International Searching Authority dated Feb. 27, 2007, for PCT Application No. PCT/US2008/003938, filed on Mar. 25, 2008, 10 pages.
Written Opinion of the International Searching Authority dated Jun. 1, 2010, for PCT Application No. PCT/US2010/029668, filed on Apr. 1, 2010, 8 pages.
Written Opinion of the International Searching Authority dated Jun. 24, 2016, for PCT Application No. PCT/US2016/024117, filed on Mar. 24, 2016, 4 pages.
Non-Final Office Action dated Mar. 13, 2008 for U.S. Appl. No. 10/963,371, filed Oct. 11, 2004, 13 pages.
Non-Final Office Action dated Aug. 6, 2008 for U.S. Appl. No. 10/963,371, filed Oct. 11, 2004, 14 pages.
Final Office Action dated Jun. 22, 2009, for U.S. Appl. No. 10/963,371, filed Oct. 11, 2004, 11 pages.
Notice of Allowance dated Sep. 17, 2010, for U.S. Appl. No. 10/963,371, filed Oct. 11, 2004, 7 pages.
Non-Final Office Action dated Jun. 26, 2009, for U.S. Appl. No. 11/600,671, filed Nov. 15, 2006, 9 pages.
Final Office Action dated Apr. 14, 2010, for U.S. Appl. No. 11/600,671, filed Nov. 15, 2006, 7 pages.
Notice of Allowance dated Sep. 17, 2010, for U.S. Appl. No. 11/600,671, filed Nov. 15, 2006, 7 pages.
Non-Final Office Action dated Jul. 22, 2010, for U.S. Appl. No. 12/037,802, filed Feb. 26, 2008, 10 pages.
Final Office Action dated Apr. 26, 2011, for U.S. Appl. No. 12/037,802, filed Feb. 26, 2008, 9 pages.
Non-Final Office Action dated Jan. 16, 2013, for U.S. Appl. No. 12/037,802, filed Feb. 26, 2008, 10 pages.
Final Office Action dated Nov. 8, 2013, for U.S. Appl. No. 12/037,802, filed Feb. 26, 2008, 15 pages.
Notice of Allowance dated Apr. 3, 2014, for U.S. Appl. No. 12/037,802, filed Feb. 26, 2008, 8 pages.
Non-Final Office Action dated Mar. 7, 2012, for U.S. Appl. No. 12/124,023, filed May 20, 2008, 13 pages.
Final Office Action dated Oct. 18, 2012, for U.S. Appl. No. 12/124,023, filed May 20, 2008, 15 pages.
Non-Final Office Action dated May 31, 2013, for U.S. Appl. No. 12/124,023, filed May 20, 2008, 14 pages.
Non-Final Office Action dated May 4, 2015, for U.S. Appl. No. 12/124,023, filed May 20, 2008, 8 pages.
Notice of Allowance dated Oct. 21, 2015, for U.S. Appl. No. 12/124,023, filed May 20, 2008, 9 pages.
Non-Final Office Action dated Dec. 30, 2009, for U.S. Appl. No. 11/400,714, filed Apr. 7, 2006, 8 pages.
Final Office Action dated Jul. 21, 2010, for U.S. Appl. No. 11/400,714, filed Apr. 7, 2006, 10 pages.
Notice of Allowance dated Nov. 24, 2010, for U.S. Appl. No. 11/400,714, filed Apr. 7, 2006, 8 pages.
Non-Final Office Action dated Dec. 22, 2011, for U.S. Appl. No. 13/033,532, filed Feb. 23, 2011, 8 pages.
Final Office Action dated Jul. 11, 2012, for U.S. Appl. No. 13/033,532, filed Feb. 23, 2011, 8 pages.
Final Office Action dated Jun. 8, 2017, for U.S. Appl. No. 14/625,540, filed Feb. 18, 2015, 14 pages.
Final Office Action dated Sep. 6, 2018, for U.S. Appl. No. 14/625,540, filed Feb. 18, 2015, 15 pages.
Non-Final Office Action dated Apr. 2, 2014, for U.S. Appl. No. 13/033,532, filed Feb. 23, 2011, 8 pages.
Final Office Action dated Aug. 12, 2014, for U.S. Appl. No. 13/033,532, filed Feb. 23, 2011, 6 pages.
Non-Final Office Action dated Oct. 28, 2015, for U.S. Appl. No. 13/033,532, filed Feb. 23, 2011, 9 pages.
Final Office Action dated Apr. 1, 2016, for U.S. Appl. No. 13/033,532, filed Feb. 23, 2011, 8 pages.
Non-Final Office Action dated Nov. 15, 2010, for U.S. Appl. No. 12/055,213, filed Mar. 25, 2008, 18 pages.
Non-Final Office Action dated Apr. 28, 2011, for U.S. Appl. No. 12/055,213, filed Mar. 25, 2008, 20 pages.
Final Office Action dated Oct. 28, 2011, for U.S. Appl. No. 12/055,213, filed Mar. 25, 2008, 15 pages.
Non-Final Office Action dated Sep. 18, 2013, for U.S. Appl. No. 12/055,213, filed Mar. 25, 2008, 15 pages.
Notice of Allowance dated Mar. 4, 2014, for U.S. Appl. No. 12/055,213, filed Mar. 25, 2008, 9 pages.
Non-Final Office Action dated Oct. 27, 2011, for U.S. Appl. No. 12/363,359, filed Jan. 30, 2009, 11 pages.
Final Office Action dated May 4, 2012, for U.S. Appl. No. 12/363,359, filed Jan. 30, 2009, 10 pages.
Non-Final Office Action dated Jun. 17, 2014, for U.S. Appl. No. 12/363,359, filed Jan. 30, 2009, 7 pages.
Final Office Action dated Nov. 14, 2014, for U.S. Appl. No. 12/363,359, filed Jan. 30, 2009, 10 pages.
Non-Final Office Action dated Sep. 10, 2015, for U.S. Appl. No. 12/363,359, filed Jan. 30, 2009, 13 pages.
Final Office Action dated Mar. 17, 2016, for U.S. Appl. No. 12/363,359, filed Jan. 30, 2009, 10 pages.
Non-Final Office Action dated Nov. 9, 2011, for U.S. Appl. No. 12/363,381, filed Jan. 30, 2009, 10 pages.
Final Office Action dated May 16, 2012, for U.S. Appl. No. 12/363,381, filed Jan. 30, 2009, 8 pages.

(56) References Cited

OTHER PUBLICATIONS

Notice of Allowance dated Apr. 1, 2014, for U.S. Appl. No. 12/363,381, filed Jan. 30, 2009, 9 pages.
Notice of Allowance dated Dec. 29, 2014, for U.S. Appl. No. 12/363,381, filed Jan. 30, 2009, 9 pages.
Non-Final Office Action dated Feb. 17, 2011, for U.S. Appl. No. 12/212,511, filed Sep. 17, 2008, 14 pages.
Final Office Action dated Sep. 20, 2011, for U.S. Appl. No. 12/212,511, filed Sep. 17, 2008, 8 pages.
Non-Final Office Action dated Apr. 2, 2012, for U.S. Appl. No. 12/212,511, filed Sep. 17, 2008, 5 pages.
Final Office Action dated Jul. 24, 2012, for U.S. Appl. No. 12/212,511, filed Sep. 17, 2008, 6 pages.
Notice of Allowance dated Feb. 22, 2013, for U.S. Appl. No. 12/212,511, filed Sep. 17, 2008, 8 pages.
Notice of Allowance dated Mar. 18, 2013, for U.S. Appl. No. 12/212,511, filed Sep. 17, 2008, 6 pages.
Non-Final Office Action dated Mar. 29, 2013, for U.S. Appl. No. 12/752,873, filed Apr. 1, 2010, 16 pages.
Non-Final Office Action dated Dec. 2, 2016, for U.S. Appl. No. 14/625,540, filed Feb. 18, 2015, 20 pages.
Final Office Action dated Jan. 13, 2014, for U.S. Appl. No. 12/752,873, filed Apr. 1, 2010, 10 pages.
Non-Final Office Action dated Nov. 10, 2014, for U.S. Appl. No. 12/752,873, filed Apr. 1, 2010, 10 pages.
Notice of Allowance dated Jul. 22, 2015, for U.S. Appl. No. 12/752,873, filed Apr. 1, 2010, 8 pages.
Non-Final Office Action dated Mar. 31, 2015, for U.S. Appl. No. 13/490,919, filed Jun. 7, 2012, 14 pages.
Final Office Action dated Nov. 18, 2015, for U.S. Appl. No. 13/490,919, filed Jun. 7, 2012, 10 pages.
Non-Final Office Action dated Oct. 16, 2017, for U.S. Appl. No. 15/080,410, filed Mar. 24, 2016, 14 pages.
Non-Final Office Action dated Jan. 4, 2018, for U.S. Appl. No. 15/080,398, filed Mar. 24, 2016, 6 pages.
Non-Final Office Action dated Jan. 12, 2018, for U.S. Appl. No. 14/928,836, filed Oct. 30, 2015, 12 pages.
Non-Final Office Action dated Jan. 17, 2018, for U.S. Appl. No. 15/041,777, filed Feb. 11, 2016, 13 pages.
Non-Final Office Action dated Jan. 26, 2018, for U.S. Appl. No. 14/625,540, filed Feb. 18, 2015, 16 pages.
Notice of Allowance dated Apr. 11, 2016, for U.S. Appl. No. 14/195,797, filed Mar. 3, 2014, 14 pages.
Notice of Allowance dated Feb. 13, 2018, for U.S. Appl. No. 15/080,410, filed Mar. 24, 2016, 10 pages.
Supplemental Notice of Allowability dated Feb. 27, 2018, for U.S. Appl. No. 15/080,410, filed Mar. 24, 2016, 2 pages.
Notice of Allowance dated Jul. 13, 2018, for U.S. Appl. No. 15/080,398, filed Mar. 24, 2016, 10 pages.
Final Office Action dated Nov. 23, 2018, for U.S. Appl. No. 14/928,836, filed Oct. 30, 2015, 12 pages.
Extended European Search Report dated Nov. 20, 2018, for EP Application No. 16769738.2 , 7 pages.
Extended European Search Report dated Feb. 20, 2019, for EP Application No. 18211384.5, 8 pages.
Extended European Search Report dated Dec. 13, 2019, for EP Application No. 19179162.3, 8 pages.
Non-Final Office Action dated May 30, 2019, for U.S. Appl. No. 14/928,836, filed Oct. 30, 2015, 10 pages.
Non-Final Office Action dated Mar. 27, 2019, for U.S. Appl. No. 14/625,540, filed Feb. 18, 2015, 14 pages.
Non-Final Office Action dated Mar. 15, 2019, for U.S. Appl. No. 15/634,982, filed Jun. 27, 2017, 10 pages.
Final Office Action dated Sep. 12, 2019, for U.S. Appl. No. 14/625,540, filed Feb. 18, 2015, 16 pages.
Final Office Action dated Sep. 17, 2019, for U.S. Appl. No. 14/928,836, filed Oct. 30, 2015, 11 pages.
Final Office Action dated Sep. 26, 2019, for U.S. Appl. No. 15/634,982, filed Jun. 27, 2017, 7 pages.
Non-Final Office Action dated Oct. 30, 2019, for U.S. Appl. No. 15/934,144, filed Mar. 23, 2018, 19 pages.
Notice of Allowance dated Mar. 12, 2020 for U.S. Appl. No. 15/934,144, filed Mar. 23, 2018, 9 pages.
Non-Final Office Action dated Mar. 20, 2020 for U.S. Appl. No. 14/625,540, filed Feb. 18, 2015, 15 pages.
Notice of Allowance dated May 28, 2020 for U.S. Appl. No. 14/928,836, filed Oct. 30, 2015, 8 pages.
Notice of Allowance dated Jul. 13, 2020 for U.S. Appl. No. 14/928,836, filed Oct. 30, 2015, 3 pages.
Non-Final Office Action dated Jul. 29, 2020 for U.S. Appl. No. 15/634,982, filed Jun. 27, 2017, 9 pages.
Notice of Allowance dated Sep. 18, 2020 for U.S. Appl. No. 14/928,836, filed Oct. 30, 2015, 3 pages.

\* cited by examiner

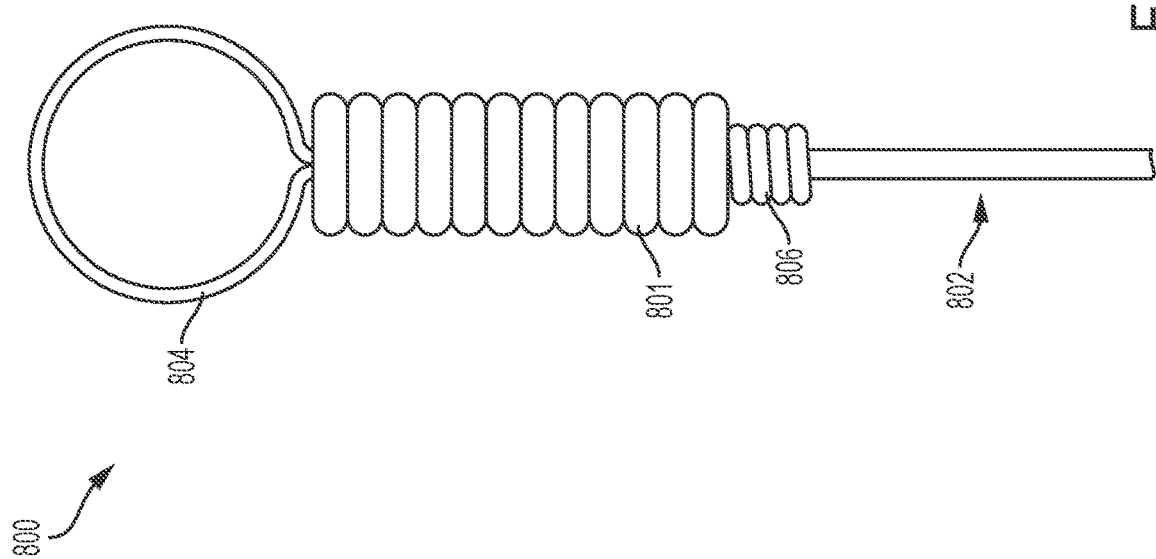
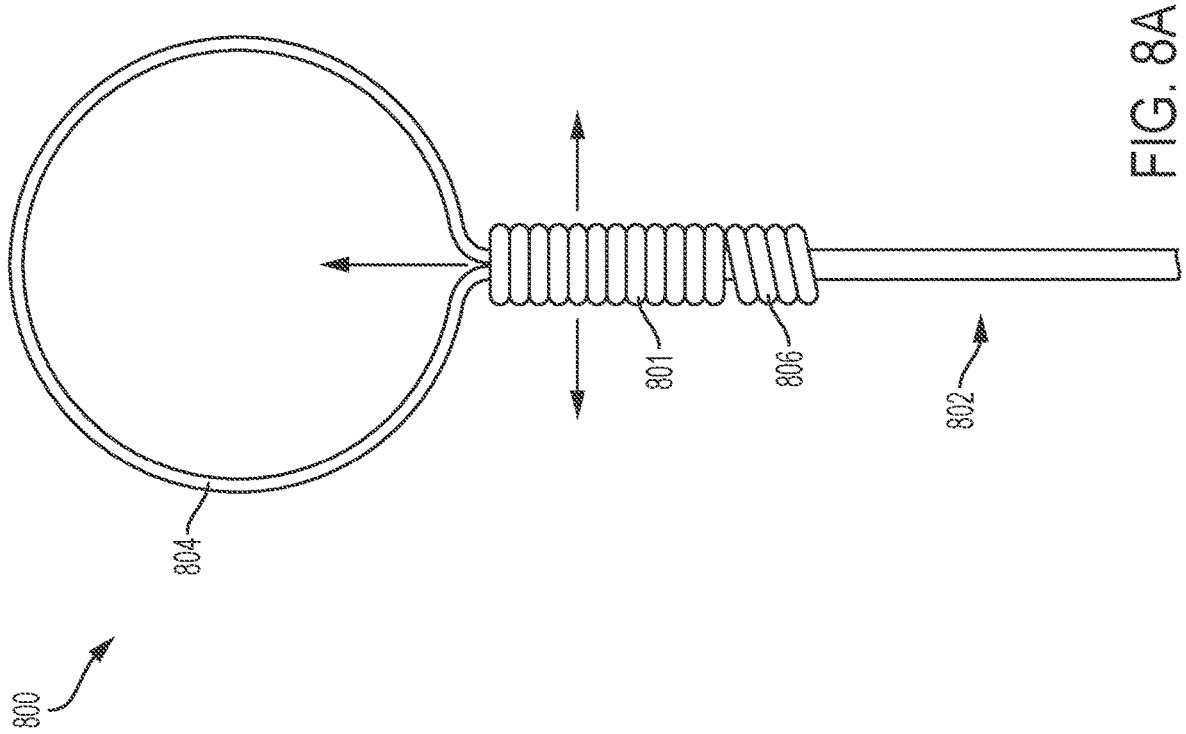

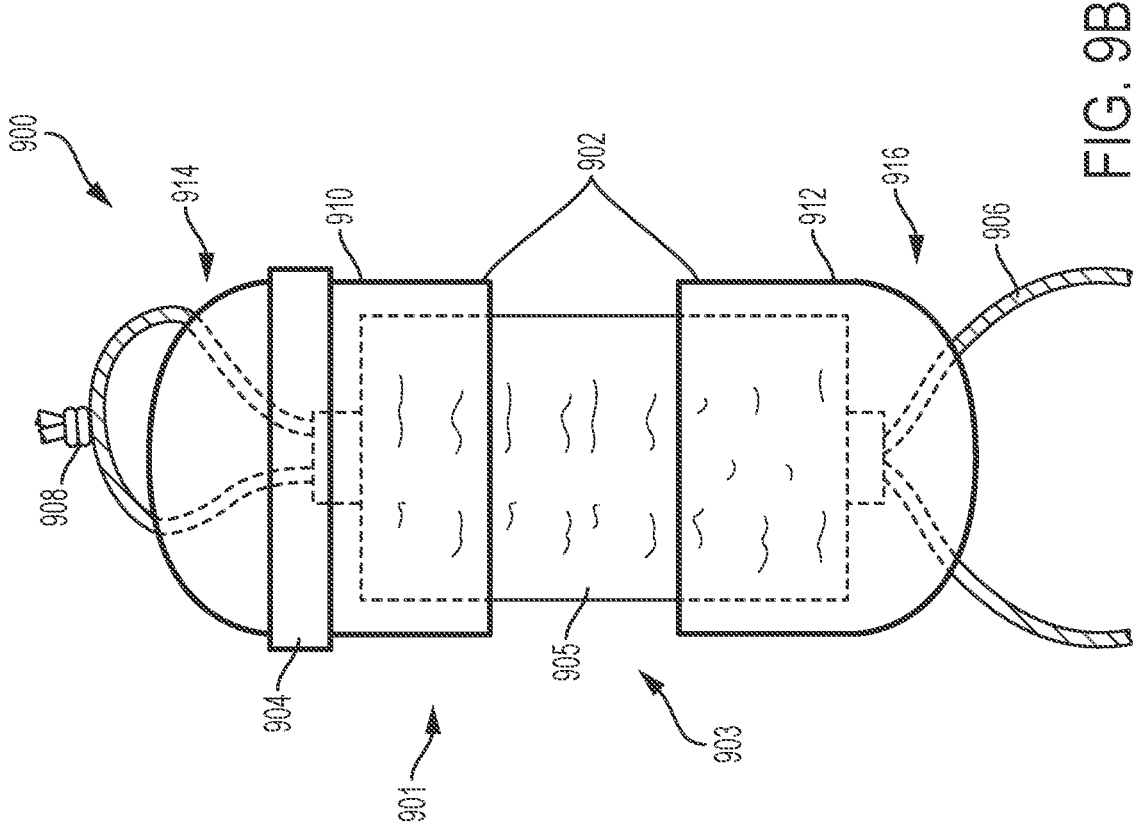
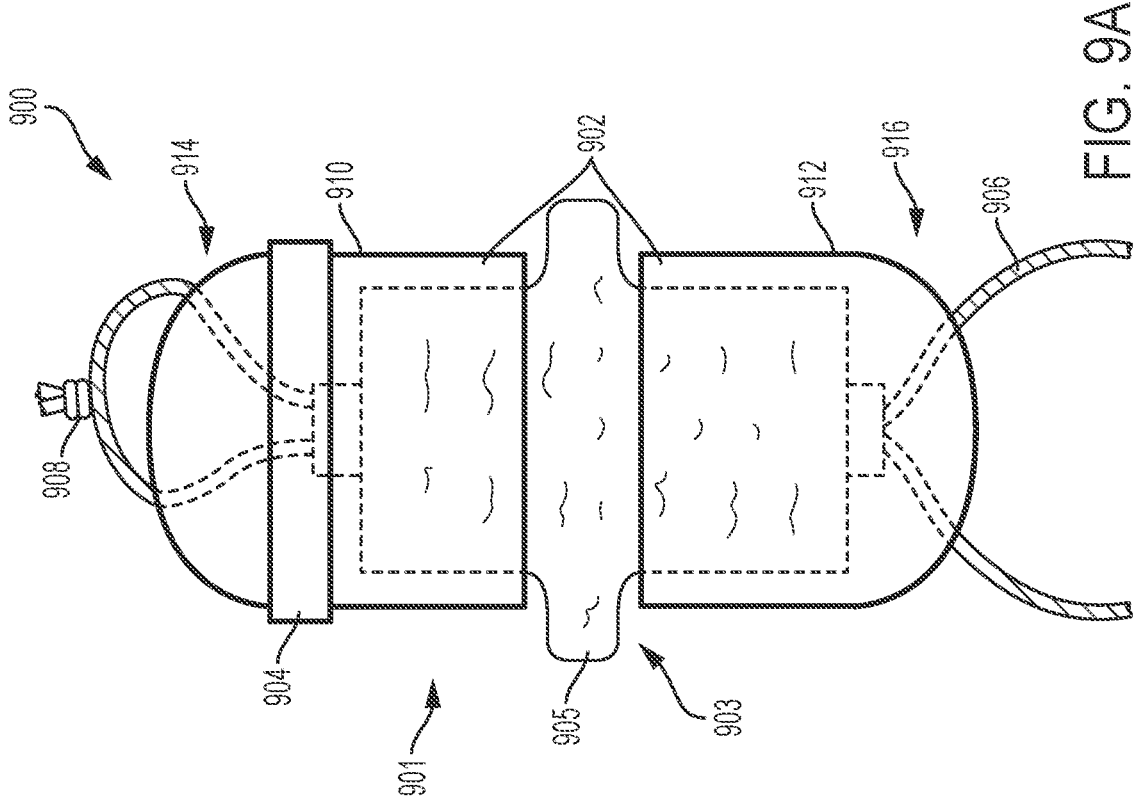

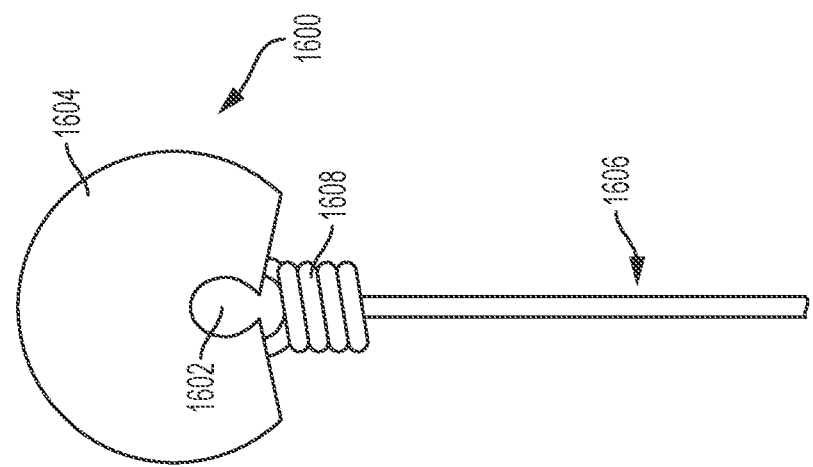
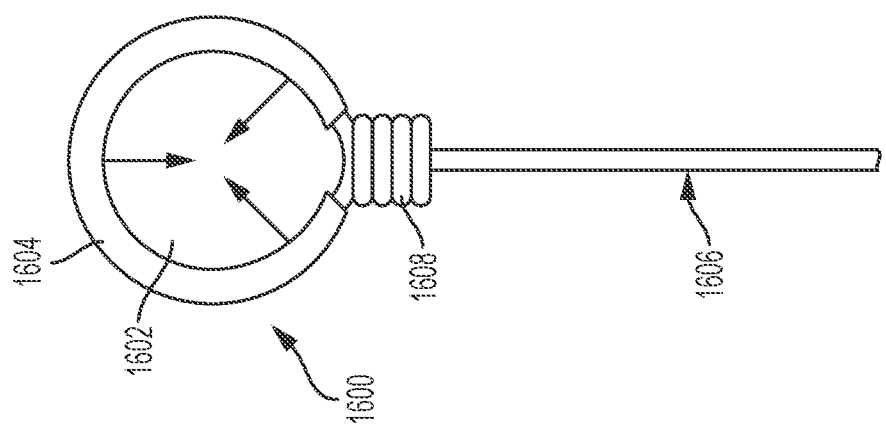

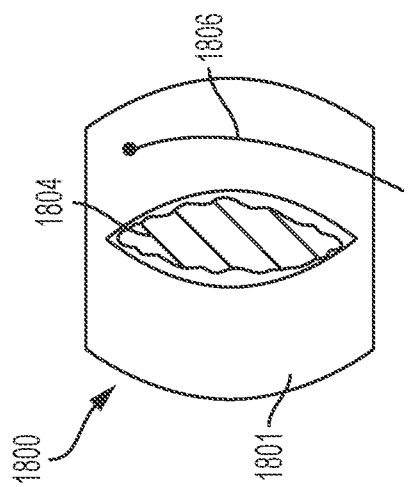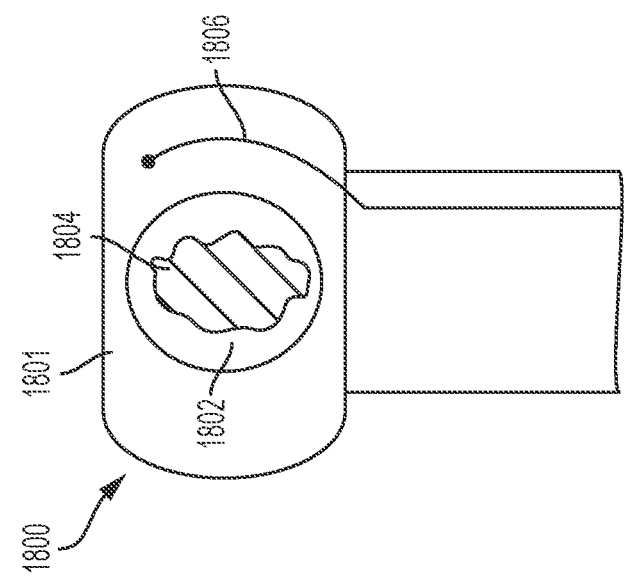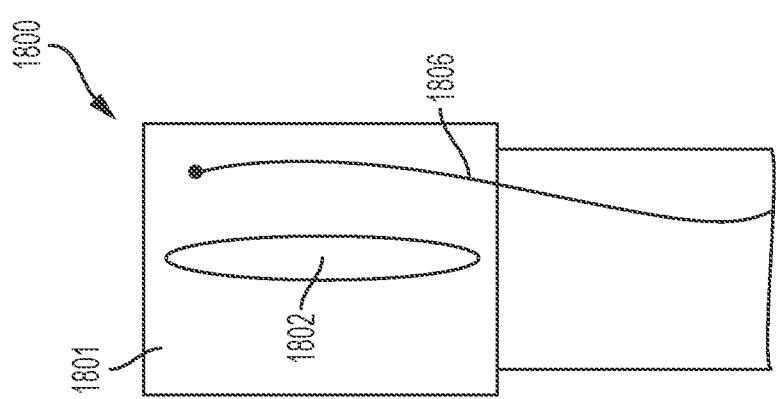

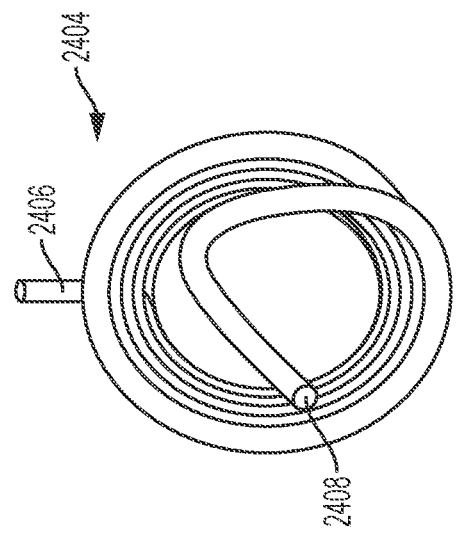
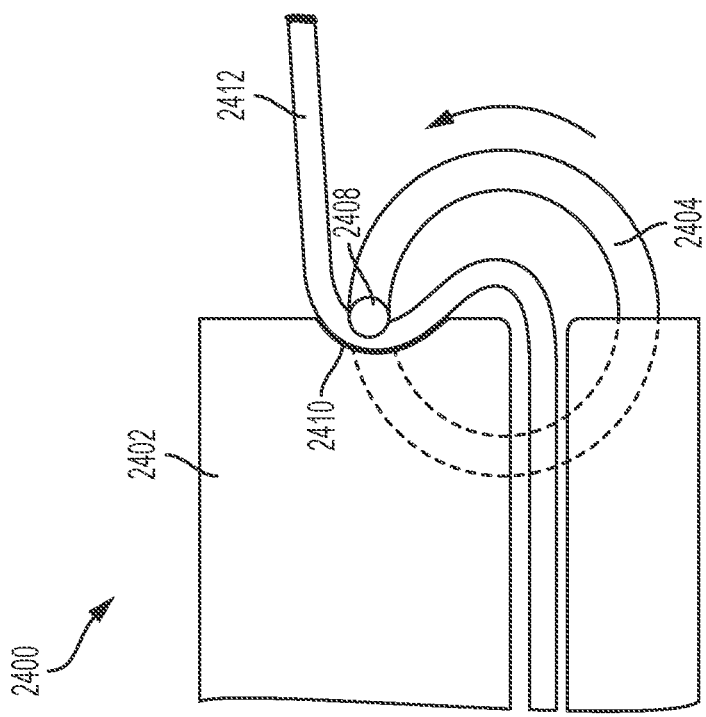
FIG. 24B
FIG. 24A

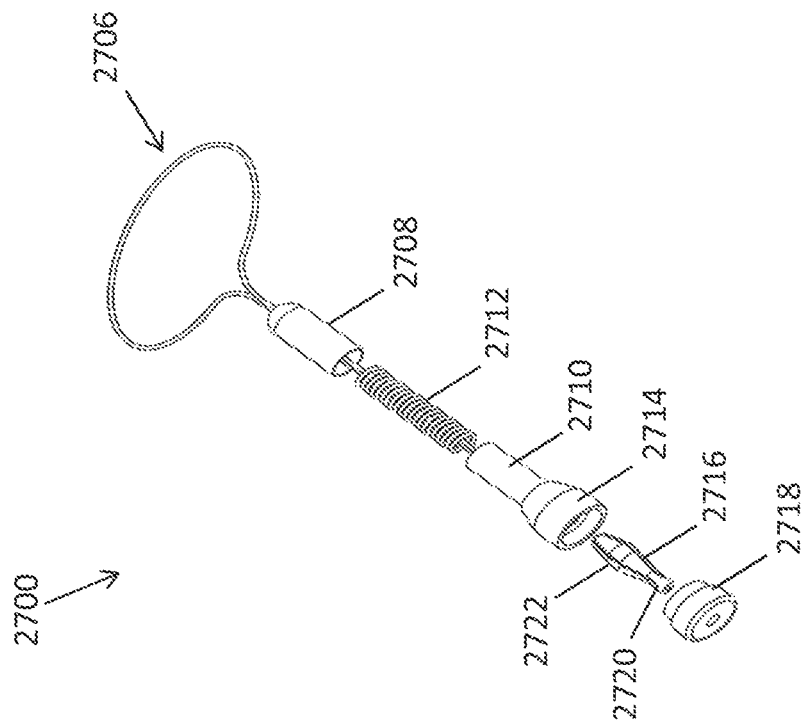
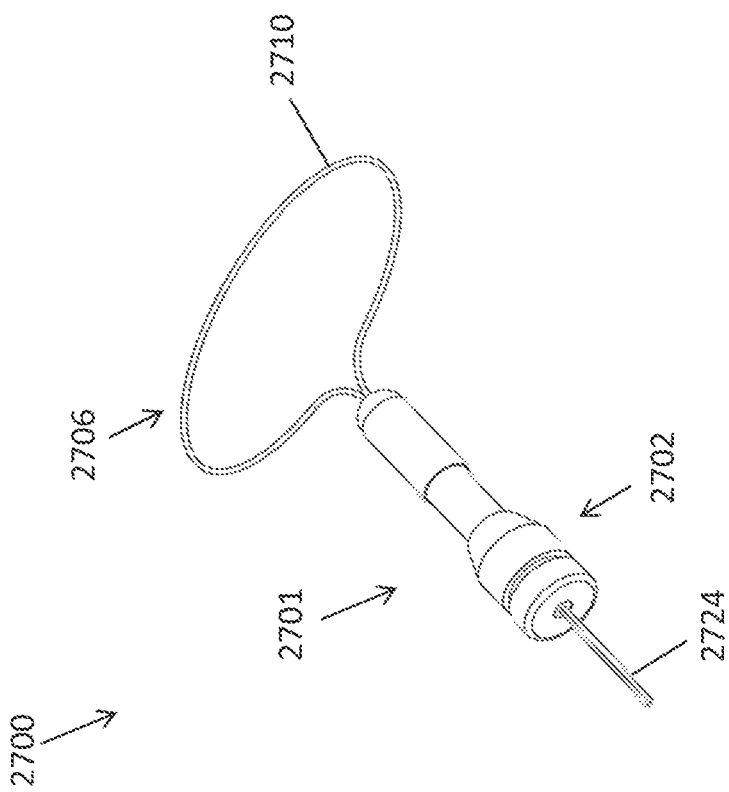

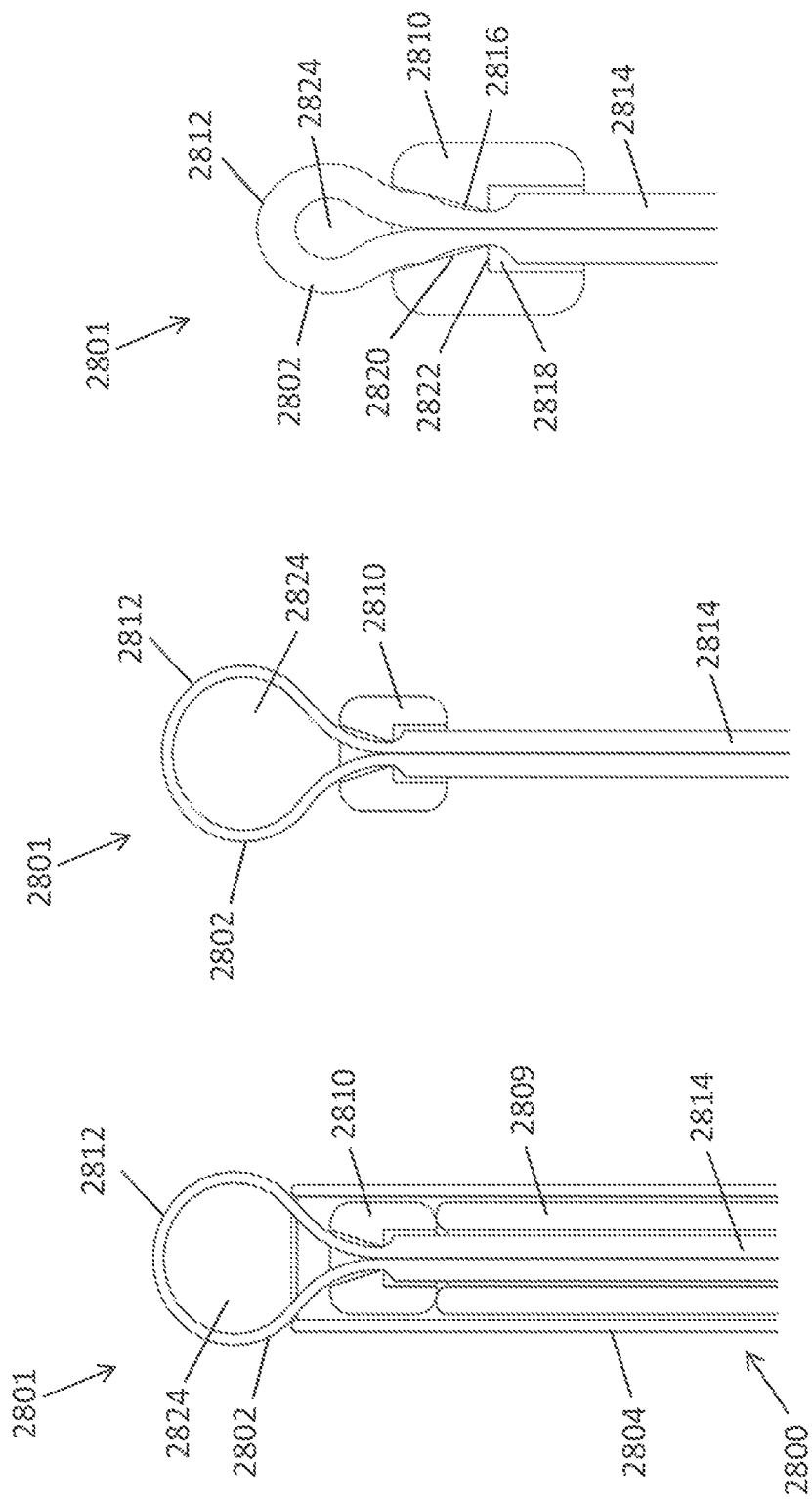

TISSUE LIGATION DEVICES AND METHODS THEREFOR

CROSS-REFERENCE TO RELATED APPLICATIONS

This application is a continuation of U.S. patent application Ser. No. 15/080,398, filed on Mar. 24, 2016, which issued as U.S. Pat. No. 10,130,369 on Nov. 20, 2018, and which claims priority to U.S. Provisional Patent Application Ser. No. 62/137,740, filed on Mar. 24, 2015, each of which is hereby incorporated by reference herein in its entirety.

BACKGROUND

Atrial fibrillation is a common problem that afflicts millions of patients. Unfortunately, atrial fibrillation often results in the formation of a thrombus, or clot, in the appendage of the left atrium. This presents a problem, inasmuch as the thrombus can dislodge and embolize to distant organs, resulting in adverse events such as a stroke. For this reason, most patients with atrial fibrillation are treated with a blood thinner to help prevent the formation of a thrombus. Blood thinners, however, can present health risks (e.g., bleeding), particularly in the elderly, and often also require that the user make significant lifestyle changes.

Several methods have been developed to address the potential problem of thrombus formation in the left atrial appendage. One such method is suturing along the base, or ostial neck of the appendage, where it joins the atrial chamber. In this way, blood flow into the atrial appendage is cut-off, eliminating the risk of thrombus formation therein. This is typically done through open-heart surgery, making the availability of the procedure available to only those who are otherwise undergoing an open-heart procedure, or who are at particularly high risk. In addition, open-heart surgery requires general anesthesia and has a number of well-known risks, making it less desirable. Furthermore, after the left atrial appendage has been sutured, the tissue may remodel and shrink. Through this process, an area that was tightly closed at the time of suturing may develop leaks over time.

Other methods have also been investigated, including methods of stapling the base of the appendage and methods of filling the appendage with a space occupying or occluding member. However, stapling is not a preferred method given the fragility of the appendage and the likelihood of its rupture. Occlusion devices may not effectively prevent all blood flow into the appendage, leaving areas of potential thrombus formation.

Additional devices and methods for closing the left atrial appendage would therefore be desirable. In particular, devices and methods for closing the left atrial appendage using minimally invasive, intravascular, or a combination of these techniques, would be desirable in order to avoid the need for opening the chest. Of course, additional devices for use in open surgical procedures are desirable as well, especially when those devices offer additional advantages over standard devices.

BRIEF SUMMARY

Described herein are tissue closure devices and methods for closing, ligating, or otherwise restricting a target tissue, such as the left atrial appendage. In some embodiments, a tissue closure device may comprise an elongate body, a snare at least partially housed within the elongate body, a suture at least partially housed within the elongate body, and a tightening element coupled to the suture. The suture may comprise a suture loop, and the tightening element may be configured to decrease the size of the suture loop when the area of a tissue within the suture loop decreases. In some variations, the tightening element may comprise a compressed configuration and an expanded configuration, and the tightening element may be configured to decrease the size of the suture loop when the tightening element is in the compressed configuration. The tightening element may comprise a force generator, and the force generator may comprise a compression spring, an expandable polymer, a shape memory alloy, and/or a bladder. In variations of force generators that comprise a bladder, the bladder may be at least partially filled with a liquid. In some embodiments, the tightening element may comprise a housing, and the force generator may be at least partially disposed in the housing. In some variations, the closure device may comprise a one-way mechanism configured to prevent expansion of the tightening element in a proximal direction relative to the suture. In some of these variations, the one way mechanism may be configured to prevent movement of the suture through the one-way mechanism in a distal direction. In some variations, the one-way mechanism may comprise a one-way suture knot. In other variations, the one-way mechanism may comprise a one-way lock. In still other variations, the one-way mechanism may comprise a suture knot and a one-way lock. In these variations, the tightening element may be positioned proximal to the suture knot. In some embodiments of the closure device, the snare and the suture loop may be releasably coupled.

In some variations, the tissue closure devices described here may comprise an elongate body, a snare at least partially housed within the elongate body, and a tightening element coupled to the snare. The snare may comprise a snare loop and a shape memory alloy, and the tightening element may be configured to decrease a size of the snare loop when an area of a tissue within the snare loop decreases. In some of these variations, the tightening element may comprise a compressed configuration and an expanded configuration and the tightening element may be configured to decrease the size of the snare loop when the tightening element is in the compressed configuration. In some instances, the tightening element may comprise a force generator, and in some of these instances, the force generator may comprise a compression spring. In some variations, the tightening element may comprise a housing, and the force generator may be at least partially disposed in the housing. In some embodiments, an increase in the length of the force generator may result in a decrease in a size of the snare loop. The snare loop and the tightening element may be configured to exert an initial closure force on the tissue, and maintain the initial closure force when the area of the tissue within the snare loop decreases. The snare and the tightening element may be releasable from the closure device.

In some variations, the tightening element may further comprise a lock. The lock may be configured to prevent movement of the snare through the lock in a distal direction. In some instances, the force generator may be positioned distal to the lock. In some embodiments, the lock may comprise teeth. In other embodiments, the snare may comprise protrusions and the lock may be configured to prevent the protrusions from moving distally through the lock. In still other embodiments, the lock may comprise a collar that may comprise an adjustable diameter and the collar may be configured to prevent the size of the snare loop from increasing. In some of these embodiments, the lock may further comprise a body that may at least partially house the collar, and a cap that may be coupled to the collar and the body. In these variations, movement of the cap relative to the body may adjust the diameter of the collar.

In some embodiments, the tissue closure device described here may comprise an elongate body, a snare at least partially housed within the elongate body, and a tightening element that has an aperture. In these embodiments, the tightening element may be configured to decrease the size of the aperture when the area of a tissue within the aperture decreases. In some variations, the tightening element may comprise an expandable polymer and/or a balloon. In variations of tightening elements comprising a balloon, the balloon may be configured to be at least partially filled with a liquid and/or a foam. In some variations, the tightening element may comprise an expanded configuration and a compressed configuration, and the tightening element may be configured to decrease the size of the aperture when the tightening element is in the compressed configuration. In other variations, the tightening element may comprise an open configuration and a closed configuration, and the tightening element may be configured to decrease the size of the aperture when the tightening element is in the open configuration.

In some variations, the tightening element may comprise a force generator and a lock, the force generator may comprise a loop and ends, and the loop may at least partially define the aperture. In some instances, the closure device may further comprise a pusher slideably disposed in the elongate body and the pusher may be configured to move the lock. In these variations, the force generator may have a cross-sectional diameter and the cross-sectional diameter of the force generator may decrease when a tensile force is applied to the force generator. In some embodiments, the tightening element may comprise an open configuration in which the loop may be configured to encircle a target tissue and the loop and the ends may be relaxed, a tensioned-closed configuration in which the loop may be configured to apply a closure force to the target tissue and the loop and the ends may be tensioned, and a relaxed-closed configuration in which the loop may be configured to apply a closure force to the target tissue, the loop may be tensioned, and the ends may be relaxed. In some of these embodiments, the lock may comprise a lumen therethrough, and the lumen may comprise a narrow region that may be configured to prevent the force generator from moving through the lumen when the tightening element is in the open configuration and the relaxed-closed configuration. In some embodiments, the narrow region may comprise a cylindrical portion and a conical portion that form a ledge, a crimped cylinder, a flattened cylinder, or depressible tabs. In some variations, the tightening element may be configured to move from the open configuration to the tensioned-closed configuration when the lock is advanced distally. In some instances, a cross-sectional diameter of the ends of the force generation may be greater than a cross-sectional diameter of the loop of the force generator when the tightening element is in the relaxed-closed configuration.

In some variations, the method of ligating tissue may comprise advancing a closure device to a target tissue, where the closure device may comprise a snare, a suture, and a tightening element. The suture may comprise a suture loop, and the tightening element may comprise a compressed configuration and an expanded configuration. The tightening element may be configured to decrease the size of the suture loop when the tightening element is in the compressed configuration. The method may further comprise positioning the suture loop around the target tissue and releasing the suture loop and the tightening element from the closure device when the tightening element is in the compressed configuration. In some variations, the snare may comprise a snare loop, which may be configured to be opened and closed. In some variations, the method may further comprise closing the snare loop around the target tissue. In some variations, the suture loop may be tightened around the target tissue after the snare loop has been closed around the target tissue. In some variations, the snare loop may be opened to disengage the snare loop from the target tissue. The methods may further comprise confirming closure of the target tissue with a visualization technique prior to releasing the suture loop and the tightening element from the closure device. In some variations, the suture loop and the tightening element may be released from the closure device by severing the suture.

In some embodiments, a tissue closure device may comprise an elongate body with a proximal end and a distal end, a snare having a snare loop, and an actuating mechanism. The snare loop may be positioned at the distal end of the elongate body, and the actuating mechanism may be configured to rotate the snare loop relative to a longitudinal axis of the elongate body. In some variations, the actuating mechanism may be configured to rotate the elongate body and the snare loop. In some variations, the actuating mechanism may be configured to rotate the snare loop independently of the elongate body. In some variations, the actuating mechanism may comprise a lever. In some embodiments, the tissue closure device may further comprise a handle at the proximal end of the elongate body. In some of these embodiments, the handle may comprise a slot and the actuating mechanism may traverse the slot. In some variations, the slot may be configured to limit rotation of the snare loop. In some variations, the tissue closure device may comprise at least one detent configured to at least temporarily hold the snare loop in a specified rotational position.

BRIEF DESCRIPTION OF THE DRAWINGS

FIGS. 8A and 8B illustrate a variation of a tightening element and suture loop arrangement described here comprising an expandable polymer coil in a compressed configuration and an expanded configuration, respectively.

FIGS. 9A and 9B depict a variation of a tightening element and suture loop arrangement described here comprising a bladder in a compressed configuration and an expanded configuration, respectively.

FIGS. 16A and 16B depict a variation of a tightening element described here having an aperture and comprising an expandable polymer in a compressed configuration and an expanded configuration, respectively.

FIGS. 18A and 18B show a variation of a tightening element described here comprising an aperture in a closed configuration and an open configuration, respectively. FIG. 18C depicts a variation of a tightening element separated from the closure device.

FIGS. 20A and 20D are perspective views, FIG. 20B is a perspective view with a portion of the handle removed, and FIG. 20C is a top view.

FIG. 24A depicts a cross-sectional side view of a portion of a one-way lock, and FIG. 24B depicts a variation of a torsion spring that may be used in the one-way lock depicted in FIG. 24A.

FIGS. 27A and 27B depict perspective and exploded views, respectively, of a variation of a tightening element and snare loop arrangement.

FIGS. 28A-28F depict cross-sectional side views of a variation of a tightening element comprising an aperture.

DETAILED DESCRIPTION

Figure 1:
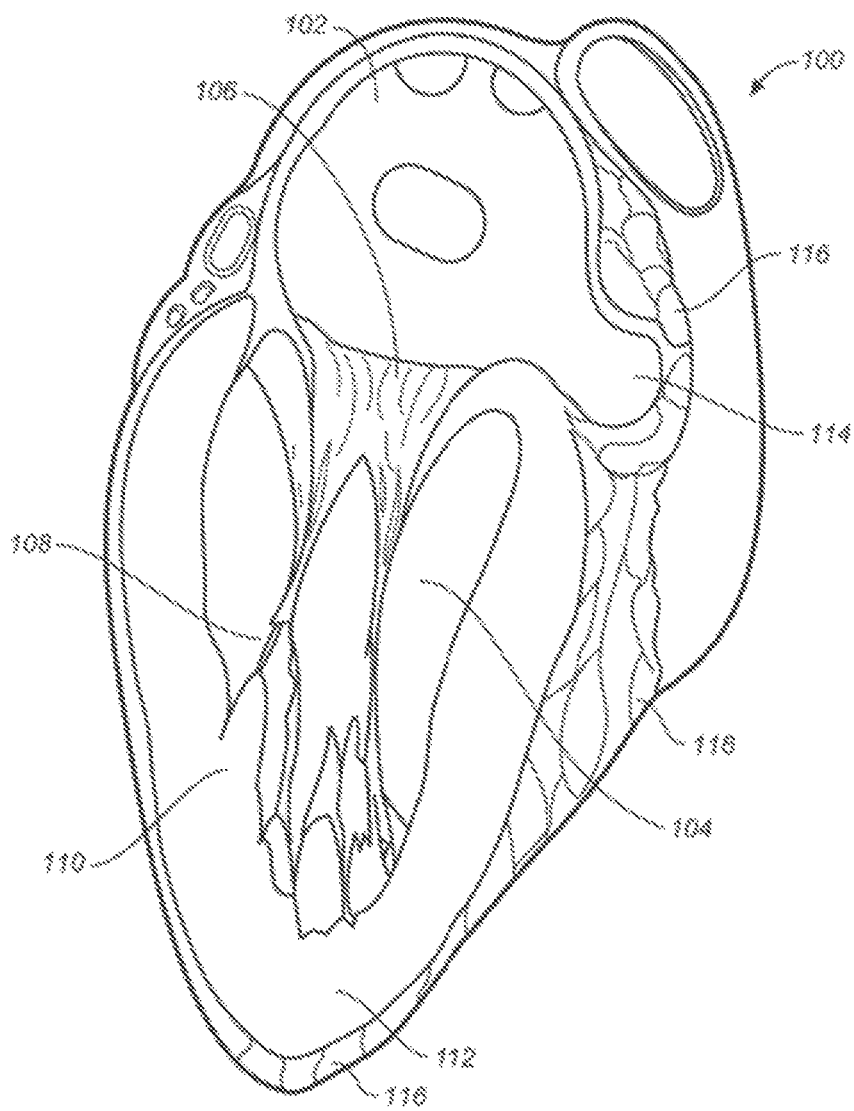
FIG. 1 provides a cross-sectional representation of a heart showing various anatomic structures.

Described here are devices and methods for closing tissue. While these closure devices and methods may be used in several anatomic locations (e.g., in the gastrointestinal tract, the hepatobiliary system, the reproductive system), this description will focus on closure of the left atrial appendage. The cardiac anatomy that is relevant to closure of the left atrial appendage is shown in the cross-sectional view of the heart (100) in FIG. 1. The left atrium (102) and the left ventricle (104) are separated by the mitral valve (also known as the bicuspid valve), which is defined by a pair of mitral valve leaflets (106). The leaflets (106) are connected to chordae tendinae (108) that are, in turn, connected to papillary muscles (110). The papillary muscles (110) join the ventricular wall (112). The left atrial appendage (114) is formed from the wall of the left atrium (102).

The left atrial appendage (114) is located within the boundaries of the pericardium (116) and is in close proximity to the ventricular wall (112). The left atrial appendage (114) typically has a tubular shape that approximates a cone, with a slight narrowing or neck in the plane of the orifice where it joins the left atrium (102). In patients with atrial fibrillation, the left atrial appendage (114) is the most common location for thrombosis formation. Over time, a thrombus may become dislodged and embolize, which can cause a stroke. For this reason, procedures to treat atrial fibrillation often include exclusion of the left atrial appendage from the left atrium. In patients with atrial fibrillation, the left atrial appendage is often excluded or removed during other procedures, such as mitral valve surgery. The devices and methods described here help to ensure proper closure of the left atrial appendage at the neck or base of the left atrial appendage, along the anatomic ostial plane, and help to maintain this closure even as tissue remodels over time. In this way, exclusion of the entire left atrial appendage from systemic circulation may be facilitated.

Generally, the closure devices described herein comprise an elongate body, a handle, and a closure element or snare, such as those described in U.S. Pat. No. 8,771,297, entitled "Devices, Systems, and Methods for Closing the Left Atrial Appendage" and filed on Mar. 25, 2008, and U.S. patent application Ser. No. 12/752,873, entitled "Tissue Ligation Devices and Controls Therefor" and filed on Apr. 1, 2010, now U.S. Pat. No. 9,198,664, issued on Dec. 1, 2015, the contents of each of which are hereby incorporated by reference in their entirety. In addition, the closure devices described herein may comprise a tightening element, which may be coupled to a suture or a snare. These devices may be suitable for use with minimally invasive access to the left atrial appendage (e.g., through a small incision above, beneath or through the rib cage, through an incision in the costal cartilage or the xiphoid, through a port, through the vasculature, and the like.). The devices described herein may also be suitable for use with open surgical access to the left atrial appendage (e.g., a median sternotomy, a mini sternotomy, a thoracotomy, a thoracoscopy, and the like.).

The elements of the closure devices may function together to close a target tissue. The closure devices may have a handle or other control mechanism (e.g., a surgical master-slave robotic system) coupled to a proximal end of the elongate body and a snare, tightening element, and/or suture positioned at the distal end of the elongate body. The handle may be used to control and/or actuate the snare, tightening element, and/or suture. The snare may comprise a snare loop, which may be used to temporarily close, tighten, ligate or otherwise restrict tissue. To facilitate this, a user may open and close the snare loop. Closing the snare loop may allow for low-profile advancement of the snare loop to a target location, and/or may allow the snare loop to tighten around a target tissue. Conversely, opening the snare loop may allow the snare loop to be placed around one or more target tissues, or may allow the snare loop to release one or more target tissues previously restricted by the snare loop.

Temporary closure of a target tissue by the snare loop may allow the quality of the closure (e.g., the effectiveness of the closure at stopping material from moving through the tissue, the position of the closure) to be determined prior to releasing a more permanent closure element, such as a tightening element coupled to a suture or a tightening element coupled to the snare itself. Opening and closing the snare loop may allow it to be positioned or repositioned until proper closure has been confirmed (e.g., confirmed with a visualization technique). The closure device may comprise one or more features that may facilitate proper positioning of the snare loop around the target tissue. For example, as will be described in detail herein, the closure device may comprise an actuating mechanism configured to rotate the snare loop relative to a longitudinal axis of the elongate body. In some variations, the snare loop may be temporarily coupled to the suture and/or tightening element, such that actuation (e.g., rotation, opening, closing) of the snare loop may also actuate the suture and/or tightening element. For example, in some variations, a retention member may temporarily couple the snare loop and the suture.

The closure devices described herein may comprise an element or elements configured to be released at a target tissue in order to keep the tissue closed after the closure device has been withdrawn from the body. In some embodiments, a tightening element may be released from the closure device at the target tissue. The tightening element may be configured to maintain a continuous closure force on the target tissue, even if the size of the target tissue decreases over time. In some variations, the tightening element may be coupled to a suture loop that may be positioned at the distal end of the elongate body. In these variations, the suture loop and tightening element arrangement may be released from the closure device. The suture loop may tightly encircle and/or close the target tissue, while the tightening element may store mechanical energy and apply a force to the suture loop and/or target tissue. The tightening element may be configured to decrease the size of the suture loop if the size of the tissue within the suture loop decreases, due to remodeling for example. In some embodiments, the tightening element may be coupled to a snare instead of a suture loop. In these variations, the snare may encircle and/or close the target tissue while the tightening element applies a force to the snare loop and/or target tissue to maintain tissue closure. In other variations, the tightening element itself may encircle and close the target tissue instead of a suture loop. In these variations, the tightening element may comprise an aperture, through which the target tissue may be positioned, and the aperture size may decrease if the tissue within the aperture shrinks. Each of these features will be described in more detail below, and it should be appreciated that the closure devices described here may comprise any combination of these features.

In use, a distal end of an elongate body may be advanced into a patient's body toward a target tissue (e.g., the left atrial appendage). This advancement may be done in a minimally invasive manner. During advancement, the snare loop may be closed to help prevent it from snagging or catching on tissue or other obstructions. Once the distal end of the elongate body has reached a location at or near the target tissue, the snare loop may be opened. The snare loop may then be advanced, moved, rotated, or otherwise manipulated to encircle at least a portion of the target tissue. The snare loop may be closed around the tissue to temporarily close, ligate, or otherwise restrict the target tissue. In some variations, the snare loop may be re-opened, repositioned, and re-closed as necessary until proper closure is confirmed. In variations in which the closure devices comprise a suture loop, opening and closing the snare loop may also open and close the suture loop. In some of these variations, the snare loop and the suture loop may be temporarily coupled to facilitate this coordinated movement.

After sufficient closure by the snare loop has been confirmed, a more permanent closure element or elements may be deployed from the closure device. In variations of closure devices comprising a tightening element and suture loop arrangement, the suture loop may be tightened around a target tissue, and the suture loop and tightening element may be released from the closure device. When the tightening element is released, it may be in a configuration in which it may act to maintain the suture loop tightly around the target tissue. In variations in which only a snare is utilized, the snare and the tightening element may be released from the closure device. When the tightening element is released, it may be in a configuration in which it may maintain the snare loop tightly around the target tissue, even if the size or amount of target tissue within the snare loop decreases. In variations of the closure device in which the tightening element itself encircles and closes the target tissue, the tightening element may be positioned such that the target tissue is at least partially within the aperture of the tightening element. The tightening element may then be released from the closure device. In these variations, when the tightening element is released, it may be in a configuration in which the aperture size may be decreased to maintain the tightening element tightly around the tissue to keep it closed.

In variations in which the snare loop is removed from the body, to remove the closure device from the body, the snare loop may be opened to release the target tissue. Once the target tissue is released, the snare loop may be closed to facilitate low-profile withdrawal. The tightening element and suture loop arrangement, or in some variations, just the tightening element, may remain at the target tissue when the closure device is withdrawn.

Devices

Figure 2A:
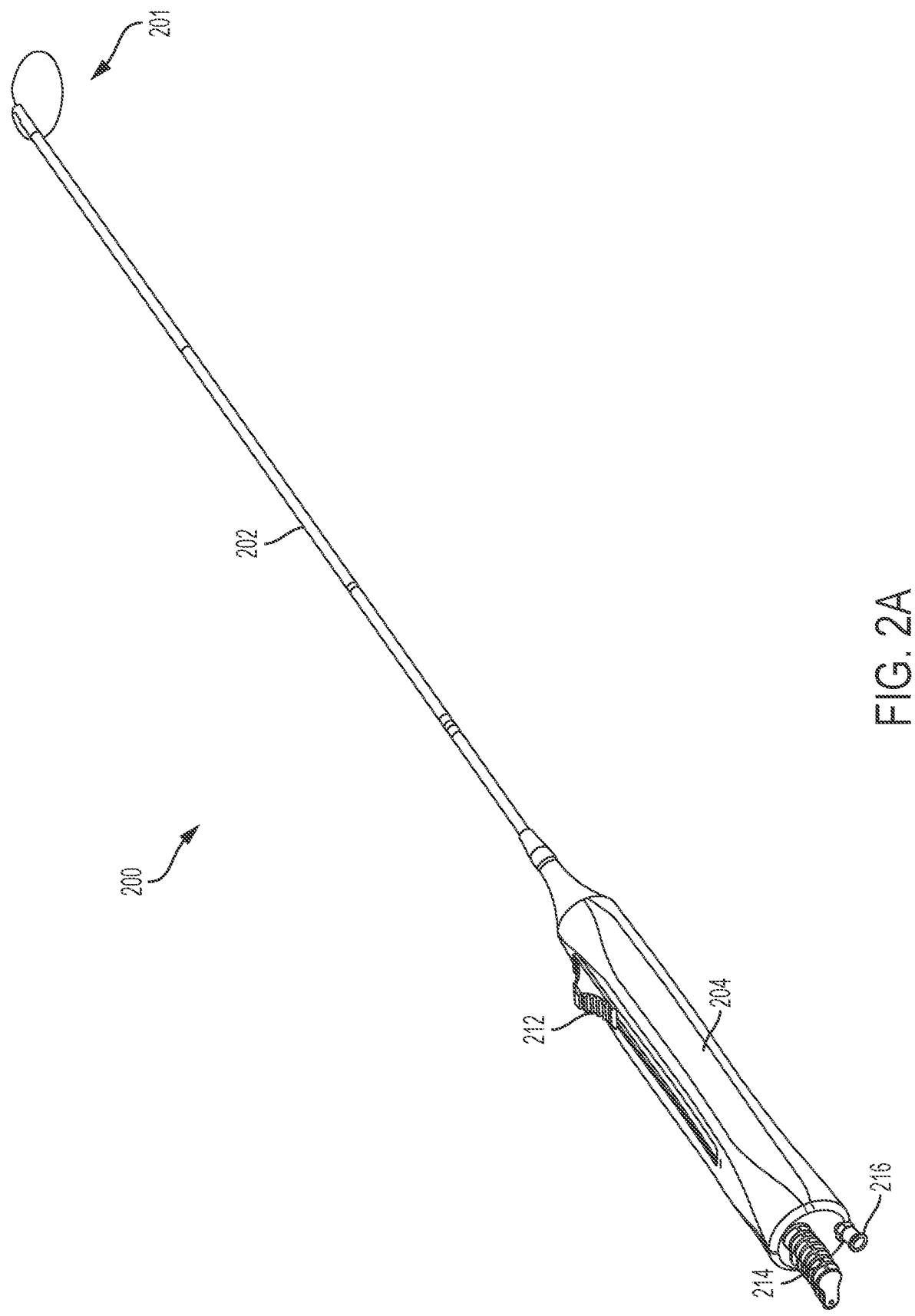
FIG. 2A is a perspective view of a variation of a closure device described here.
Figure 2B:
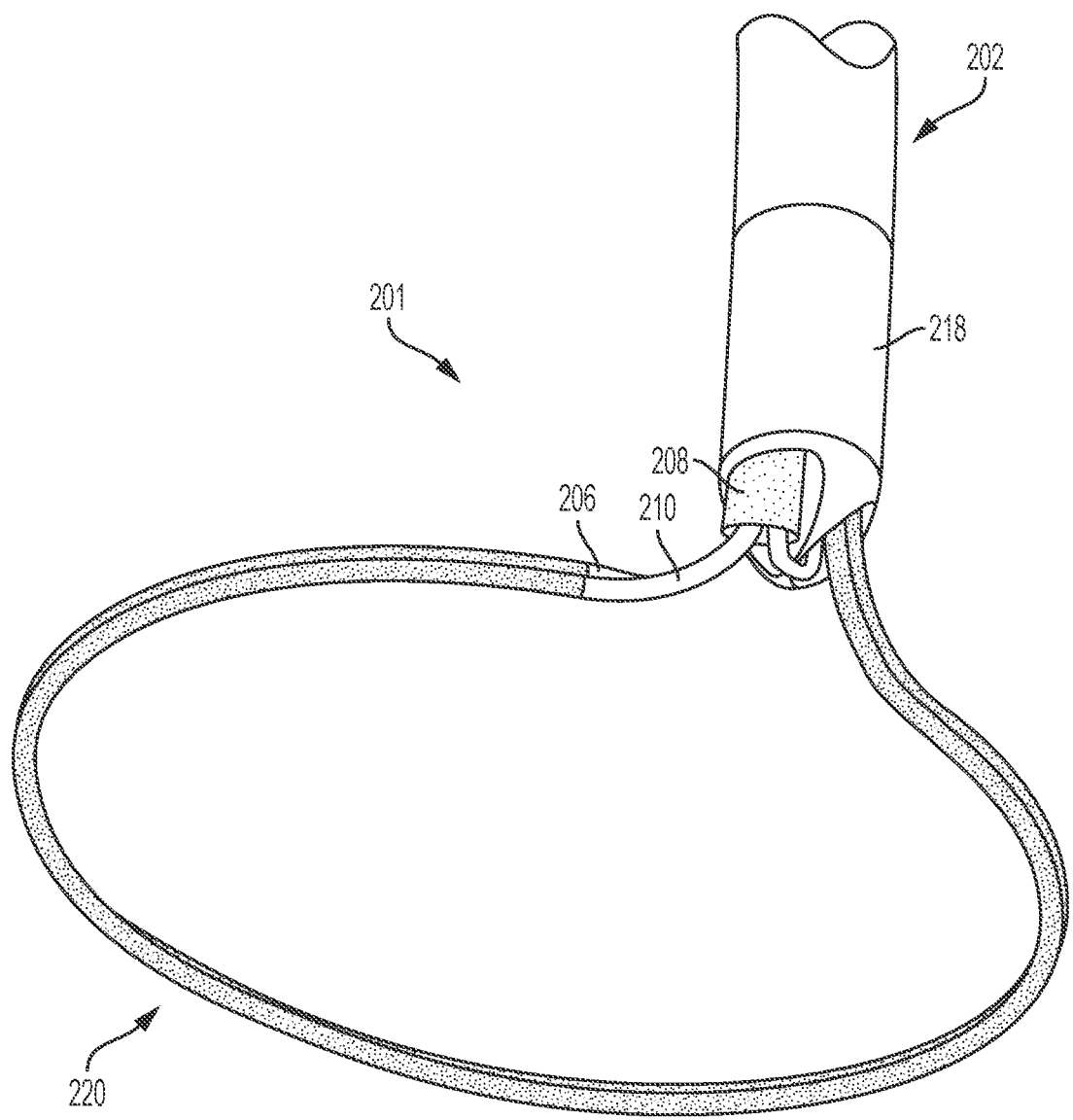
FIG. 2B is a magnified view of a distal portion of a variation of a closure device described here.

FIG. 2A depicts an illustrative closure device (200) and FIG. 2B provides a magnified view of a distal portion (201) of this closure device. As shown, the closure device (200) may comprise an elongate body (202), a handle (204), a snare (206), a tightening element (208), and a suture (210). The elongate body (202) may comprise one or more lumens, sub-lumens, and/or recesses to house at least portions of the snare (206), tightening element (208), and/or suture (210). Other portions of these elements may extend out of the distal end of the elongate body (202) and may be used to engage a target tissue. The handle (204) may be positioned at the proximal end of the elongate body (202) and may comprise one or more features to control the snare (206), tightening element (208), and/or suture (210). For example, the handle (204) shown in FIG. 2A comprises a linear actuation slide (212) configured to control (e.g., open, close) the snare (206) and a fob (214) that may be configured to control (e.g., open, close, compress, release) the tightening element (208) and/or the suture (210). In addition, the handle (204) may comprise a feature, such as a port (216), for introducing and advancing one or more instruments (e.g., a guidewire, a catheter) into the closure device (200). In some variations, the handle (204) may comprise separate controls for the suture (210) and the tightening element (208). For example, in some instances, the fob (214) may be configured to control (e.g., tighten, release) the suture (210) and a separate actuation element, for example, a slide, knob, or the like, may be configured to control (e.g., open, close, compress, release) the tightening element.

As seen in FIG. 2B, the elongate body (202) may comprise a distal tip (218), which may house at least a portion of the snare (206), suture (210), and/or tightening element (208). It should be appreciated that when reference is made to an elongate body, this may also include a distal tip. The portion of the snare (206) extending from the distal tip (218) may form a loop that may be temporarily closed around a target tissue. The portion of the suture (210) extending from the distal tip (218) may also form a loop that may encircle the target tissue. The suture (210) may be coupled to the tightening element (208), and the suture (210) and tightening element (208) may be released from the closure device (200) together. The tightening element (208) may produce a force that acts to keep the loop of the suture (210) tightly around the tissue to maintain closure.

In some variations, the loop of the suture (210) may be temporarily coupled to the loop of the snare (206), and actuation of the snare (206) may also actuate the suture (210). For example, a retention member (220) is shown in FIG. 2B connecting the snare (206) and the suture (210). The retention member (220) may be an element with a first lumen, which may house the snare (206), and a second lumen, which may house the suture (210). The suture (210) may be released from the retention member (220) prior to the release of the suture (210) and tightening element (208) from the closure device (200). For example, the suture (210) may be pulled through a slit or weakened region in the second lumen of the retention member (220) in order to decouple the suture (210) from the snare (206). Variations of retention members suitable for use with the closure devices described herein are discussed in detail in U.S. Pat. No. 8,771,297, entitled "Devices, Systems, and Methods for Closing the Left Atrial Appendage" and filed on Mar. 25, 2008, and U.S. Pat. No. 9,198,664, entitled "Tissue Ligation Devices and Controls Therefor" and filed on Apr. 1, 2010, which were previously incorporated by reference in their entirety.

While the closure device shown in FIGS. 2A and 2B comprises a tightening element coupled to a suture loop (a tightening element and suture loop arrangement), it should be appreciated that in other embodiments, the closure device may not comprise such an arrangement. For example, in some variations, the tightening element may be coupled to the snare loop directly (a tightening element and snare loop arrangement) and a suture loop may not be needed. In other variations, the tightening elements may comprise an aperture, and the tightening element may be configured to maintain a continuous closure force on a tissue without the use of a suture loop. In these variations, an aperture or loop of the tightening element itself may extend past the distal end of the elongate body, as opposed to a suture loop. A retention member may or may not temporarily couple this variation of tightening element to the snare. The types of tightening elements, those configured to be coupled to a suture loop or a snare loop as part of a tightening element and suture loop arrangement or tightening element and snare loop arrangement, respectively, and those comprising an aperture and configured for use without a suture loop, are be described in detail herein.

Snare

Figure 3A:
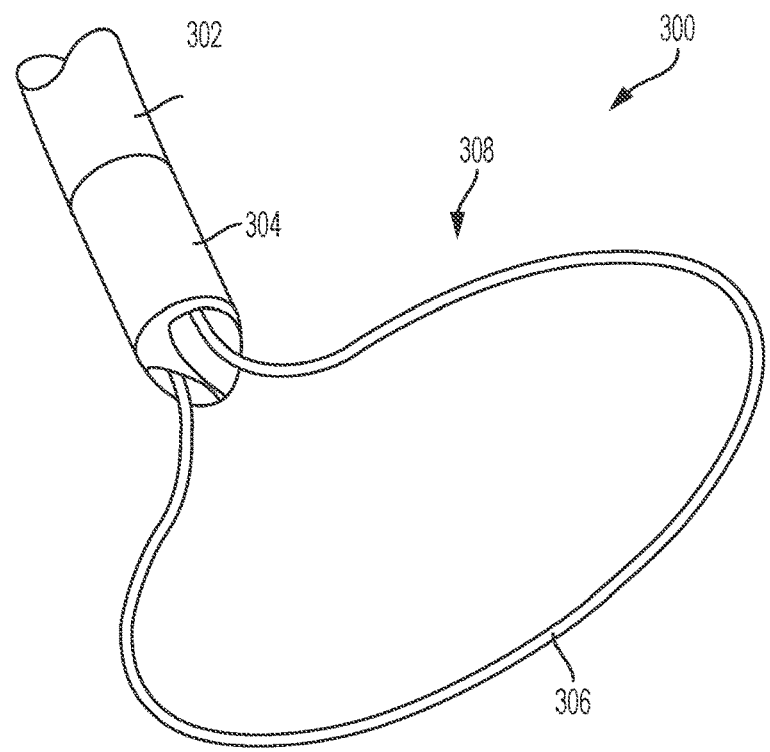
FIG. 3A shows a distal portion of a variation of a closure device described here.
Figure 3B:
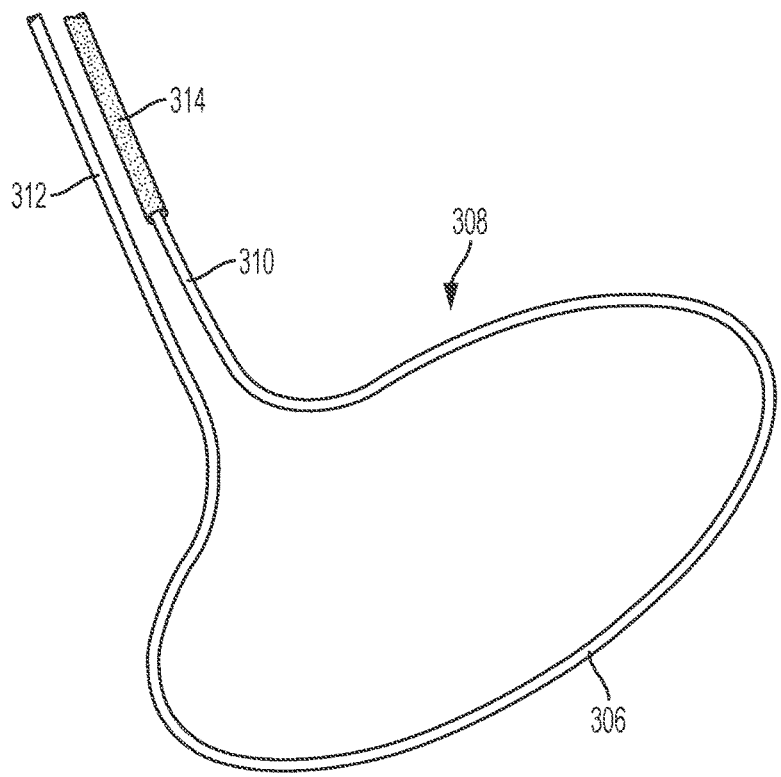
FIG. 3B shows a distal portion of a variation of a snare described here with the elongate body removed.

As mentioned above, in variations of closure devices comprising a snare, a portion of the snare may be housed in the elongate body, and another portion of the snare may extend from the distal end of the elongate body to form a snare loop. FIG. 3A shows a distal portion of a tissue closure device (300) comprising an elongate body (302), a tip (304), and a snare (308) having a snare loop (306). FIG. 3B shows a distal portion of the snare (308) without the elongate body (302) or the tip (304). It should be appreciated that the tightening element, suture, and retention member are also not shown in these figures. The snare (308) may comprise snare ends (310, 312), which may be housed in the elongate body (302) and/or the tip (304). The snare (308) may comprise a fixed end (310), which may be held stationary relative to one or more portions of the closure device (300), and a free end (312), which may be advanced and retracted through the elongate body (302). Movement of the free end (312) may change the amount of the snare (308) that is disposed outside of elongate body (302), and thus, may change the size of the snare loop (306). Specifically, distal advancement of the free end (312) through the elongate body (302) may open, or increase the size (e.g., diameter, circumference, etc.) of, the snare loop (306). Proximal retraction of the free end (312) may close, or decrease the size of, the snare loop (306).

The free end (312) of the snare (308) may be manipulated in any suitable manner. In some variations, the free end (312) may be attached directly to one or more portions of the handle. In other variations, the free end (312) may be attached to a hypotube, rod, or other rigid structure. This structure may in turn be moved by the handle, which may help facilitate advancement or retraction of the free end (312) through the elongate body (302). In some variations, both ends of the snare (308) may be free, and they may be advanced and retracted together and/or separately. It should be appreciated that in variations of closure devices comprising a retention member configured to couple the snare loop to a suture loop and/or tightening element, movement of the snare loop may also move the suture loop and/or tightening element.

In variations where one end of the snare (308) is fixed relative to the closure device (300), the fixed end (310) may be attached to any suitable portion of the device. For example, in some variations, the fixed end (310) of the snare (308) may be fixedly held in, on, or near a tip (304) of the elongate body (302). In other variations, the fixed end (310) may be affixed in one or more lumens of the elongate body (302). In still other variations, the fixed end (310) may be attached to the handle of the closure device (300). As shown in FIG. 3B, the fixed end (310) of the snare (308) may be attached to an anchoring feature (314) that may facilitate fixation to a suitable portion of the closure device (300). Although one end of the snare (306) may be fixed relative to the closure device (300), it should be appreciated that this fixed end (310) may be only temporarily fixed, and it may be configured to be releasable. Configuring the fixed end (310) to be releasable may serve a number of useful functions. In some instances, the moveable portion of the snare (306) may become stuck or caught on tissue. In these instances, it may be desirable to release the fixed end (310) in order to allow the closure device (300) to release ensnared tissue. Further detail regarding variations of releasable snares may be found in U.S. patent application Ser. No.

14/195,797, entitled "Tissue Ligation Devices and Methods Therefor" and filed on Mar. 3, 2014, the content of which is hereby incorporated by reference herein in its entirety.

The snares described here may be made of any suitable material or combination of materials. For example, in some variations the snare may be made from a shape-memory material, such as a shape-memory alloy (e.g., a nickel titanium alloy, and the like). In other variations, the snare may be made from stainless steel, polyester, nylon, polyethylene, polypropylene, combinations thereof, and the like. In variations where the snare is made from a shape-memory material, the snare loop may be configured to take on a particular shape or configuration when the snare loop is opened, but may still be at least partially withdrawn into the elongate body to close the snare loop. Variations of snares and snare loop shapes are described in detail in U.S. Pat. No. 9,198,664, entitled "Tissue Ligation Devices and Controls Therefor" and filed on Apr. 1, 2010, which was previously incorporated by reference in its entirety.

Tightening Element

While in some variations the snare loop may be configured to close a target tissue temporarily, the tightening element and suture loop or snare loop arrangement, or the tightening element alone, may be released from the closure device to apply a continuous closure force to the target tissue. The tightening element may be configured to hold the target tissue closed even if the tissue shrinks (e.g., there's a decrease in the tissue size, volume, area, amount) over time, due to remodeling for example. Utilizing a tightening element and suture or snare loop arrangement, or a tightening element alone, may reduce the risk of leaks developing through the ligated tissue, as compared to using a conventional suture loop for tissue closure. As mentioned above, leakage of material into and out of the left atrial appendage may be undesirable as it may result in thrombus formation and embolization, which may cause a stroke.

Two general types of tightening elements will be described in detail herein. A first type of tightening element may be coupled to a suture or snare having a loop, forming a tightening element and suture loop or snare loop arrangement. In these variations, the tightening element and suture or snare loop arrangement may be released from the closure device at a target tissue. The suture or snare loop may be configured to tightly encircle a target tissue, and the tightening element may exert a force on the suture or snare loop and/or the tissue. If the tissue within the suture or snare loop shrinks (e.g., there's a decrease in the area of tissue inside of the suture loop, a decrease in the volume of tissue inside of the suture loop), the tightening element may decrease the size of the suture or snare loop (e.g., the length of suture forming the suture loop, the area inside of the suture loop) to keep the tissue closed. In this way, the suture or snare loop may be maintained tightly around the target tissue, and the chance of leakage through the tissue may be reduced.

A second type of tightening element may not be coupled to a suture loop, and the tightening element itself may be configured to encircle the target tissue. This variation of tightening element may comprise an aperture, through which the target tissue may be positioned when the tightening element is released from the closure device. The aperture may comprise a variable size (e.g., diameter, circumference, area), and the tightening element may be configured such that if the size or amount of tissue within the aperture decreases, the aperture size may decrease as well. In this way, the tightening element may be maintained tightly around the target tissue to keep it closed.

Tightening Element and Suture Loop Arrangement

Figure 4:
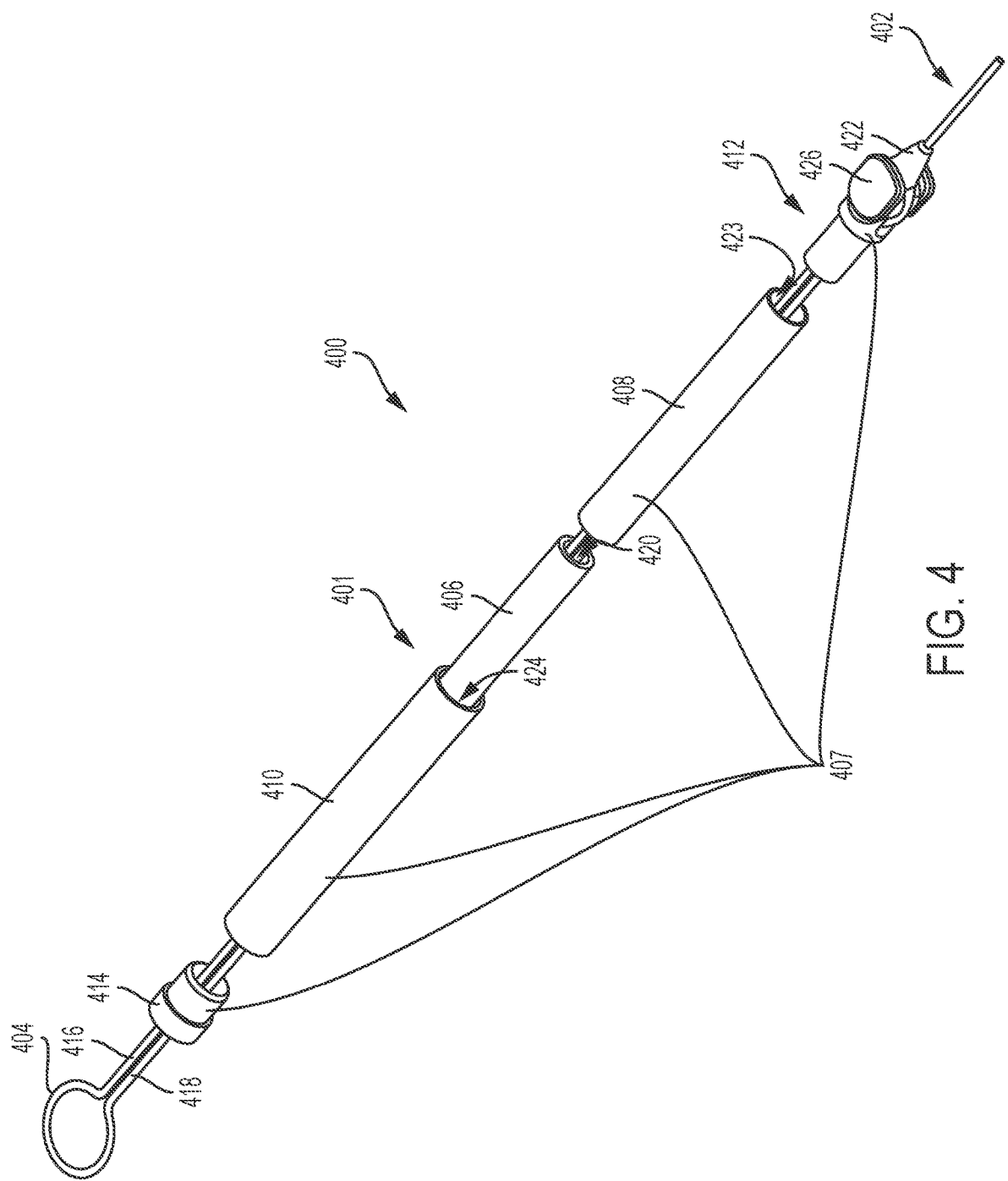
FIG. 4 is an exploded perspective view of a variation of a tightening element and suture loop arrangement described here comprising a suture knot.

FIG. 4 illustrates an exemplary tightening element and suture loop arrangement (400) comprising a tightening element (401) configured to be coupled to a suture (402) having a suture loop (404). The components of the tightening element (401) have been partially separated in this figure for clarity. The tightening element (401) may comprise a force generator (406) that is at least partially housed in a housing (407). The force generator (406) may be the component of the tightening element (401) that stores energy and produces a force. For example, the force generator (406) may be any element that has elasticity, such that when it is compressed longitudinally, it tends, or is biased, to expand back to its original size. Changes in the size and/or the shape of the force generator (406), by compression and expansion for example, may result in changes in the size and/or the shape of the tightening element (401) and changes in the size of the suture loop (404). The force generator (406) may include structures and/or materials such as compression springs, expandable polymers, and bladders.

The housing (407) may cover or enclose at least a portion of the force generator (406) and may serve several useful purposes, which will be described in more detail herein. As shown in FIG. 4, the housing (407) may comprise an inner tube (408) and an outer tube (410), and at least a portion of the inner tube (408) may be slidably disposed in the outer tube (410). The force generator (406) may be at least partially disposed in a lumen or lumens (423, 424) of the inner and/or outer tubes (408, 410). In some variations, the inner tube (408) and/or the outer tube (410) may slide relative to the other tube to allow the housing (407) to change length when the length of the force generator (406) changes. The housing (407) may also comprise proximal and distal caps (412, 414), and a force produced by the force generator (406) may be applied to the suture (402) and/or a tissue via these caps (412, 414).

The suture (402) may have two strands or legs (416, 418), which may extend from the suture loop (404) into the distal cap (414), through a lumen (420) in the force generator (406), and out of the proximal cap (412), thereby coupling the suture (402) and the tightening element (401). It should be appreciated, however, that the suture and the tightening element may be coupled in any suitable way, such that changes in the size of the tightening element may change the size of the suture loop. For example, the two suture strands or legs may extend through the same or different lumens of the tightening element, at least one leg may travel along the outside of the tightening element, or only one leg may extend through the tightening element and the other leg may be fixed to a distal portion of the tightening element.

As shown in FIG. 4, the suture legs (416, 418) may form a suture knot (422) proximal to the proximal cap (412) of the tightening element (401). In some variations, the tightening element (401) may have a feature to center or otherwise position the suture knot (422) relative to the tightening element (401) and/or the closure device, such as a hub (426) of the proximal cap (412). The suture knot (422) may hold the proximal end of the tightening element (401) stationary as the force generator (406) expands and/or compresses. Expansion of the force generator (406) may result in the length of the tightening element (401) increasing. As the tightening element (401) expands longitudinally, suture (402) from the suture loop (404) may be drawn through the distal cap (414) into the tightening element (401), and the size of the suture loop (404) may decrease.

The suture knot (422) may be a one-way surgical knot (e.g., a Meltzer knot), such that suture (402) may be pulled proximally through the suture knot (422), but may not move distally through the suture knot (422). This type of one-way mechanism may allow the suture loop (404) to be tightened without changing the length of the tightening element (401). A one-way mechanism may include a structure or structures other than a suture knot, such as a one-way lock, that directs expansion of the tightening element in one direction and/or allows movement of suture in one direction.

Figure 5A:
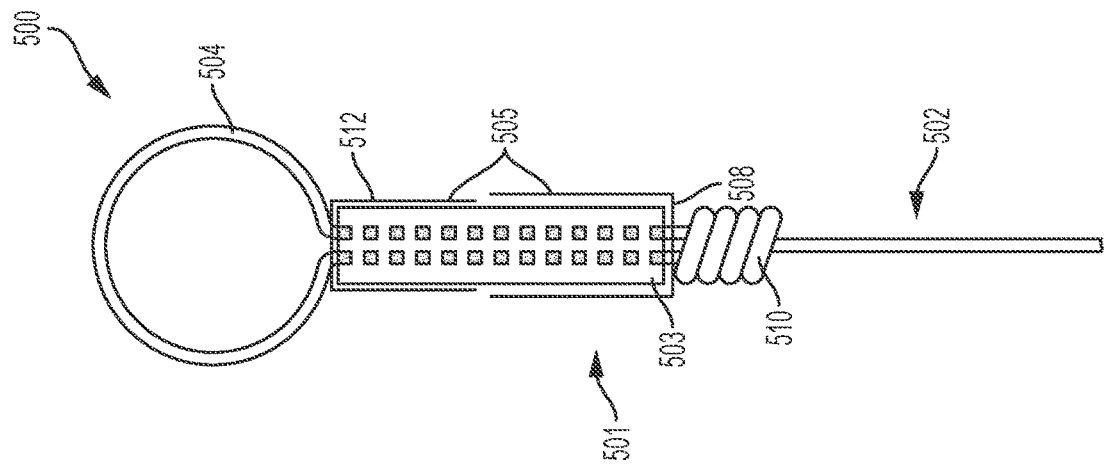
FIGS. 5A-5C show a variation of a tightening element and suture loop arrangement described here.
Figure 5B:
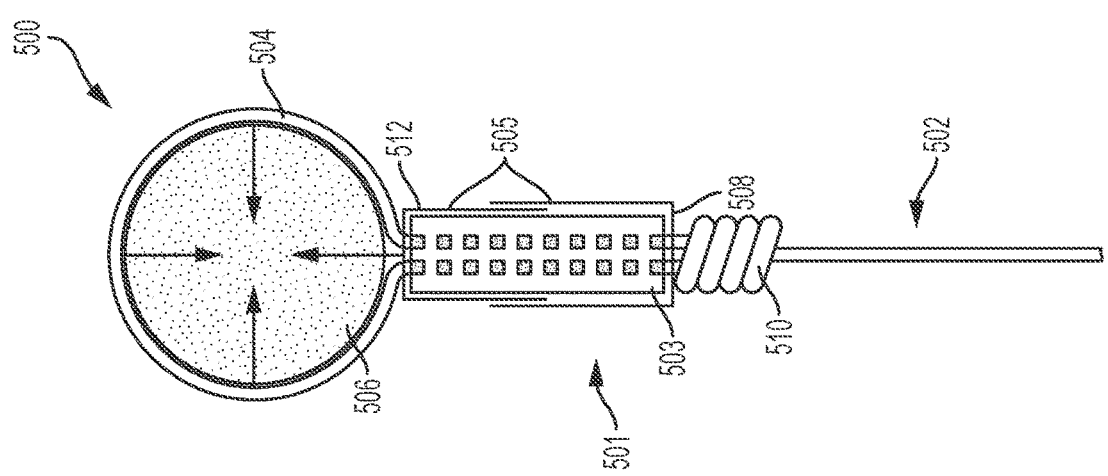
Figure 5C:
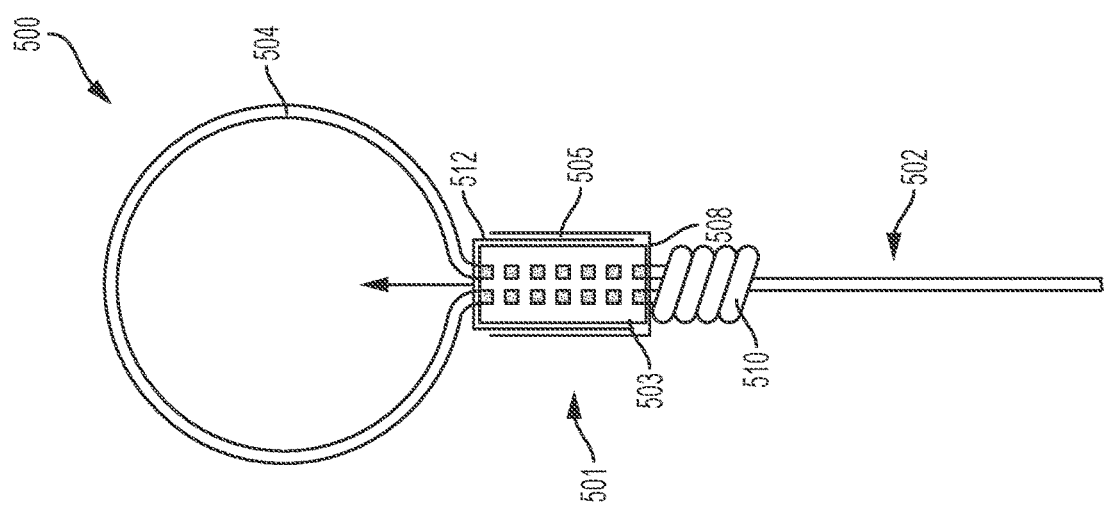

FIGS. 5A-5C depict an illustrative tightening element and suture loop arrangement (500) that may be used with the closure devices described herein. These figures generally demonstrate how a tightening element and suture loop arrangement (500) may be configured to apply a continuous closure force to a target tissue (506). The arrangement (500) may include a tightening element (501) comprising a force generator (503) and a housing (505), and a suture (502) comprising a suture loop (504) and a suture knot (510). The tightening element (501) may be disposed distal to the suture knot (508). A first portion of the suture (502), represented by dashed lines in FIGS. 5A-5C, may be housed in the tightening element (501) (e.g., in a lumen or lumens of the force generator (503), a lumen or lumens of the housing (505)). A second portion of the suture (502) may extend distally from the tightening element (501) and form a suture loop (504).

The tightening element (501) may change size (e.g., length, area, volume) and/or shape in order to change the size (e.g., length, diameter, area within) of the suture loop (504). For example, the length of the tightening element (501) may be modified by compression or expansion of the force generator (503), which may change the amount of suture (502) that is housed in the tightening element (501) and the amount of suture (502) that forms the suture loop (504). As seen in the progression from FIG. 5A to FIG. 5C, when the tightening element (501) expands longitudinally, the amount of suture (502) housed in the tightening element (501) increases and the size of the suture loop (504) decreases. The configuration of the housing (505) may allow the length of the tightening element (501) to change when the length of the force generator (503) changes. For example, in the variation shown in FIGS. 5A-5C, one portion of the housing (505) may slide relative to another to accommodate this change in length.

In some variations, a suture knot (510) may prevent the proximal end (508) of the tightening element (501) from moving. Therefore, expansion of the force generator (503) and the tightening element (501) may result in the distal end (512) of the tightening element (501) moving distally, indicated by the direction of the arrow in FIG. 5A. This distal movement may decrease the size of the suture loop (504) (e.g., the length of suture forming the suture loop, the area within the suture loop). Configuring the distal end (512) of the tightening element (501) to move over the suture (502) while the proximal end (508) remains stationary may ensure that a change in the length of the tightening element (501) results in a change in the size of the suture loop (504). While a suture knot (510) is depicted in FIGS. 5A-5C, it should be appreciated that any one-way mechanism could be employed that prevents proximal movement of the proximal end (508) of the tightening element (501). Other one-way mechanisms, such as one-way locks, will be described in more detail herein.

If the proximal end (508) of the tightening element (501) is stationary while the length of the tightening element (501) changes, then the change in length of the suture loop (504) may be about twice as much as the change in length of the tightening element (501). This is due to the fact that the two legs or ends of a suture loop (504) may each change in length by the amount that the tightening element (501) changes in length. As the tissue (506) within the suture loop (504) may shrink over time, it may be desirable for the size of the suture loop (504) to change enough that the suture loop (504) may remain tightly around the tissue (504) as the tissue shrinks. To accommodate shrinking of the left atrial appendage, it may be desirable for the tightening element (501) and the suture (502) to be configured such that the suture loop (504) may change in length by at least about 16 mm. In order to achieve this, a tightening element (501) that may change in length by at least about 8 mm may be used.

FIGS. 5A, 5B, and 5C show the force generator (503) and the tightening element (501) in fully compressed, partially compressed, and expanded configurations, respectively. At least a portion of the force generator (503) may be elastic, and this may bias the force generator (503), and thus the tightening element (501), towards the expanded configuration. In other words, unless obstructed, the force generator (503) and the tightening element (501) may tend to return to the expanded configuration after being compressed. In addition, elasticity may allow the force generator (503) to store energy and exert a force when it is in the compressed configuration. Any amount of longitudinal compression of the force generator (503) may cause it to store energy and exert a force, although the amount of energy and the magnitude of force may change based on the degree of compression. For this reason, a force generator (503) and a tightening element (501) may be considered to be in the compressed configuration whether they are fully compressed or partially compressed. In other words, the compressed configuration may include a range of compressed states.

If unobstructed, the compressed force generator (503) and tightening element (501) may fully expand to the expanded configuration shown in FIG. 5C. As mentioned above, this expansion may decrease the size of the suture loop (504). However, if a tissue (506) is within the suture loop (504) (e.g., tissue in the plane of the suture loop opening and inside of the boundaries of the opening defined by the suture loop and the tightening element), the force generator (503) and tightening element (501) may only be able to partially expand. As the force generator (503) and tightening element (501) expand, the suture loop (504) size may be decreased until it is tightly around the tissue (506) and a closure force is exerted on the tissue (506). FIG. 5B shows the suture loop (504) tightly around the tissue (506). The tissue (506) within the suture loop (504) may prevent further tightening of the suture loop (504) and further expansion of the force generator (503) and tightening element (501). Thus, the force generator (503) may be held in the compressed configuration and may continuously exert a force. In the variation shown in FIGS. 5A-5C, the force produced by the force generator (503) may be directly applied to the housing (505), and, in turn, the housing (505) may apply a force to the suture (502) and/or the tissue (506). It should be appreciated that when reference is made to the tightening element (501) producing or exerting a force, the force may originate from the force generator (503), and this force may be transferred to other components of the tightening element (501) (e.g., the housing (505)) before it is applied to the suture (502) and/or tissue (506).

Depending on the configuration of the tightening element (501) and the suture (502) (e.g., the areas of each element that contact the tissue (506)), the force produced by the tightening element (501) may be directly applied to the tissue (506) and/or to the suture (502). Force applied to the suture (502) may, in turn, be applied to the tissue (506) via the suture loop (504). The result may be that the tissue (506)

experiences forces directed radially inward, as indicated by the arrows in FIG. 5B. If the tissue (506) within the suture loop (504) shrinks over time, the force generator (503) and the tightening element (501) may expand further and decrease the suture loop (504) size until the suture loop (504) once again exerts a closure force on the tissue (506). Characteristics of the force generator (e.g., the spring constant in the case of a force generator comprising a compression spring) may be tailored or modified to provide a continuous force to a tissue that is large enough to keep the tissue closed, but not so large as to cause inadvertent tissue damage.

Force Generator

A tightening element configured to be coupled to a suture loop or a snare loop may comprise a force generator that may store mechanical energy when compressed longitudinally. When released from a compressed configuration, the force generator may exhibit elasticity and may expand longitudinally towards its original size and/or exert a force. It should be appreciated that movement of the force generator between compressed and expanded configurations may also move the tightening element between compressed and expanded configurations, respectively. Thus, the force generator may be the component of the tightening element that drives or causes the changes in length of the tightening element and the suture or snare loop. The force generator may also be the component of the tightening element responsible for producing a tissue closure force; although, the force may be applied to the housing or other components of the tightening element before it is directly applied to the suture/snare and/or the target tissue. For example, an increase in the length of the force generator may result in a decrease in the size of the suture or snare loop. This concept was described in more detail with respect to FIGS. 5A-5C.

Figure 7:
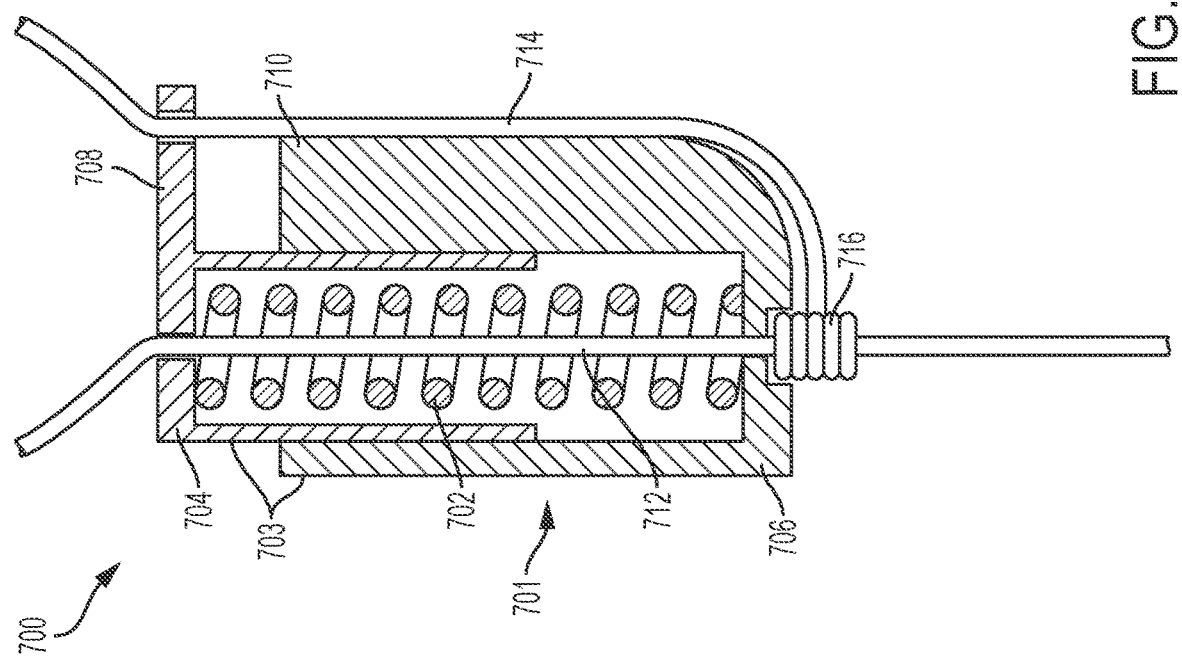
FIG. 7 depicts a variation of a tightening element and suture loop arrangement described here comprising a compression spring and stops.
Figure 6:
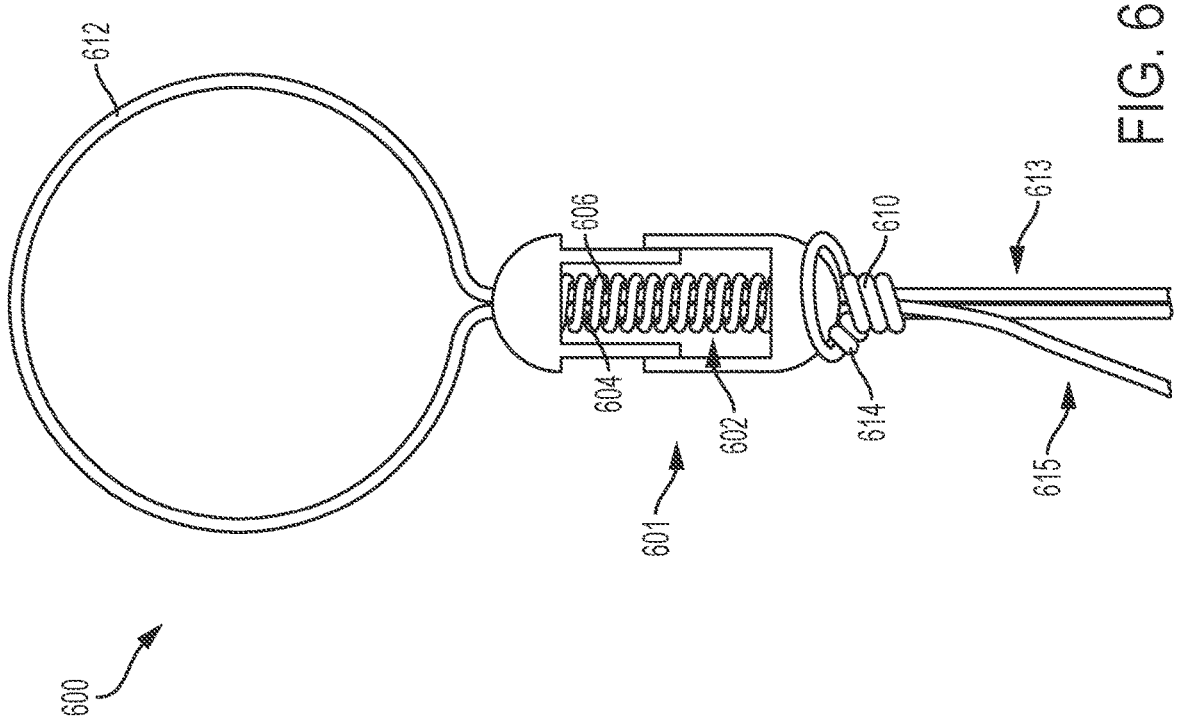
FIG. 6 depicts a variation of a tightening element and suture loop arrangement described here comprising a compression spring.

In some embodiments, the force generator may comprise one or more compression springs. FIGS. 6 and 7 illustrate two variations of tightening element and suture loop arrangements (600, 700). In these arrangements (600, 700), the tightening elements (601, 701) include force generators (602, 702) comprising compression springs. The properties of the spring and its configuration within a tightening element may determine the magnitude of force that the spring may exert and the change in size of the suture loop. For example, the spring constant of the spring and the distance it is able to compress may determine the range of forces the spring is able to exert. For a given change in length (i.e., distance compressed), a spring with a higher spring constant may store more mechanical energy and be able to exert a greater force than a spring with a lower spring constant. In addition, compression springs may exert a greater force the farther they are compressed. A longer compression spring may be able to be compressed farther and exert a greater force than a shorter compression spring with the same spring constant. Thus, the spring constant and the length of the compression spring used in a tightening element may be selected such that the force exerted by the spring is sufficient to keep a tissue closed. For example, in variations of tightening elements used to close the left atrial appendage, the spring may have a spring constant between about 2 lb/in and about 3.5 lb/in. In some variations, the spring may expand or lengthen a distance of about 0.4 inches (1.02 cm) to about 0.6 inches (1.52 cm) to maintain a continuous closure force on the tissue as the amount or size of the tissue within the loop reduces. For example, in some of these variations, the spring may expand or lengthen about 0.5 inches (1.27 cm). In some instances, the force exerted by the spring or other force generator may be about 0.5 lbs to about 2.5 lbs, about 0.6 lbs to about 2.1 lbs, about 0.65 lbs to about 0.85 lbs, about 0.87 lbs to about 1.00 lb, about 0.91 lbs to about 1.10 lbs, and/or about 1.14 lbs to about 2.04 lbs.

In some variations, the amount of compression and/or expansion of the force generator may be at least partially determined by the housing. For example, FIG. 7 depicts a tightening element and suture loop arrangement (700) with a tightening element (701) that comprises a housing (703) configured to control compression of the force generator (702). As shown there, the housing (703) comprises inner and outer tubes (704, 706) that may each comprise a stop (708, 710). The stops (708, 710) may contact each other when the force generator (702) has been compressed a specified distance, which may block further compression. Compressing a force generator a specified distance may cause the force generator to exert a specified force, as the force exerted by a force generator may be directly related to its change in length, such as in variations of force generators comprising a compression spring. It may be desirable for a force generator to exert a specified force when released from the closure device, as this may help to ensure that the force produced by the force generator is large enough to keep the tissue closed. For example, in some variations, the tightening element and/or the force generator may be configured so that the force generator exerts a force sufficient to effectuate closure of the left atrial appendage when the tightening element is released from the closure device. A stop may comprise any portion of the tightening element that contacts another portion of the tightening element to limit compression or expansion of the force generator.

A force generator may comprise one or more lumens or channels through which one or both suture strands or legs may be at least partially disposed. For example, in the variation of the tightening element and suture loop arrangement (600) shown in FIG. 6, both legs (604, 606) extend through a lumen of the force generator (602). In contrast, in FIG. 7, one suture leg (712) extends through a lumen of the force generator (702), while the other suture leg (714) travels outside of the force generator (702). In some variations, neither suture leg may travel through the force generator.

The force generator may comprise one or more structures other than a compression spring. It should be appreciated, however, that the one or more other structures may have any combination of the properties that were described with respect to a compression spring (e.g., the relationship between change in length and magnitude of force generated). For example, a force generator may comprise any elastic element that, when longitudinally compressed, tends to expand back to its original size and/or shape. In some variations, the force generator may comprise an expandable polymer (e.g., ePTFE, rubbers, silicone, urethanes, hydrogels, biogels, bio based elastomers, polylactic acid, and the like). In these variations, the expandable polymer may have any suitable configuration or shape, including but not limited to cylindrical, rectangular prism, conical, or irregular shape.

As seen in FIGS. 8A and 8B, in some variations of a tightening element and suture loop arrangement (800), the force generator (801) may comprise an expandable polymer configured as a coil. FIG. 8A shows the force generator (801) in a compressed configuration, and FIG. 8B shows the force generator (801) in an expanded configuration. As seen in these figures, the force generator (801) may comprise an expandable polymer that may expand longitudinally (indicated by the open arrow in FIG. 8A) and/or laterally (indicated by the closed arrows in FIG. 8A). When the force generator (801) is coupled to a suture (802) comprising a suture loop (804) and a suture knot (806) with the configuration shown in FIGS. 8A and 8B, only longitudinal expansion and compression of the force generator (801) may change the size of the suture loop (804). However, it should be appreciated that in other configurations, such as where the ends of the suture travel on the outside of the force generator, lateral expansion and compression of the force generator may change the size of the suture loop. In addition, while FIGS. 8A and 8B show the force generator (801) expanding uniformly (i.e., each area of the force generator expands approximately the same amount), a force generator comprising an expandable polymer may be configured to expand more in some regions than in others. FIGS. 8A and 8B also illustrate an example of a tightening element that does not include a housing. In these variations, the force generator may directly apply a force to the suture and/or the tissue, as opposed to indirectly applying a force the suture and/or the tissue via the housing.

Figure 22B:
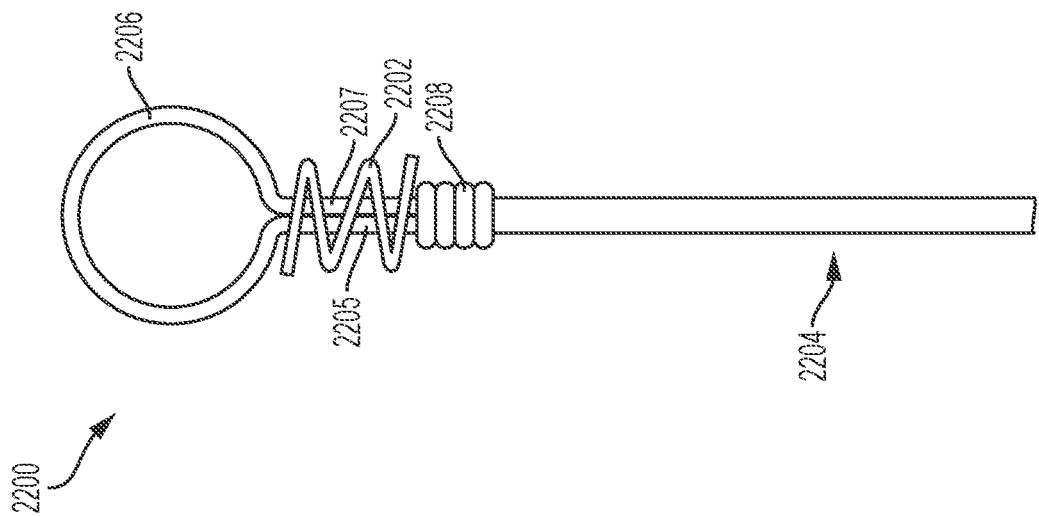
FIGS. 22A and 22B illustrate a variation of a tightening element and suture loop arrangement described here comprising a folded force generator in a compressed configuration and an expanded configuration, respectively.
Figure 22A:
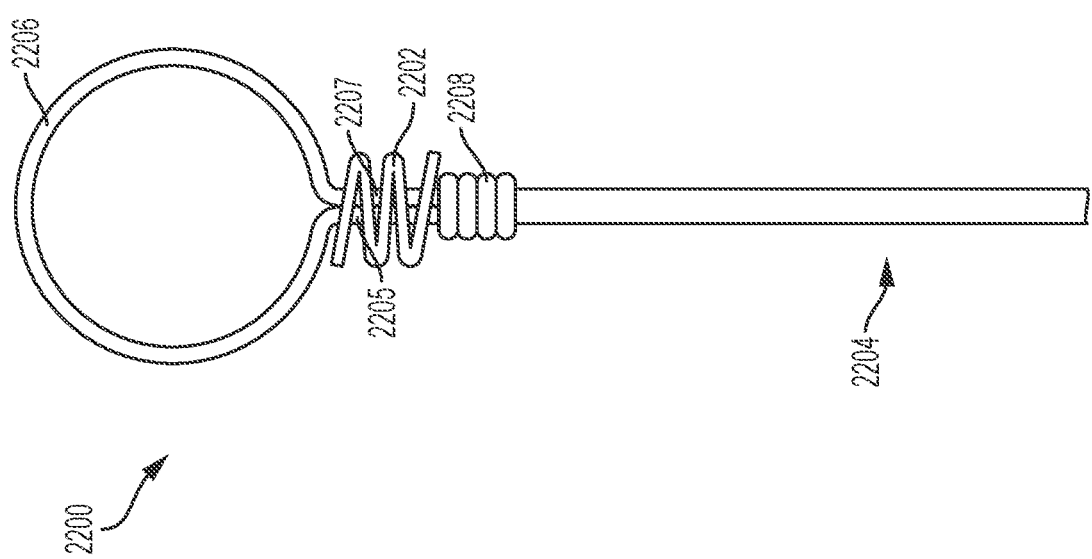

FIGS. 22A and 22B illustrate a variation of a tightening element and suture loop arrangement (2200) having a force generator (2202) that is folded and/or that has an accordion shape. The force generator (2202) may be coupled to a suture (2204) comprising a suture loop (2206) and a suture knot (2208) and may be configured such that an increase in the length of the force generator (2202) may result in a decrease in the size of the suture loop (2206). The force generator (2202) may comprise one or more lumens therethrough through which a portion of the suture loop (2206), for example, a first suture leg (2205) and a second suture leg (2207), may be slideably disposed. The force generator (2202) may comprise a compressed configuration, shown in FIG. 22A, and an expanded configuration, shown in FIG. 22B. The force generator (2202) may comprise one or more elastic materials such that it is biased towards the unfolded or expanded configuration. As the force generator (2202) expands or unfolds, its length (e.g., longitudinal distance) may increase. While the force generator (2202) shown in FIGS. 22A and 22B comprises four folds, it should be appreciated that a force generator may comprise any suitable number of folds (e.g., 1, 2, 3, 5, 6, 7, more than 7). The force generator (2202) may comprise any suitable elastic material or materials (e.g., elastic polymer, shape memory alloy, and the like), and in some variations the force generator (2202) may be a pledget.

FIGS. 9A and 9B show a tightening element and suture loop arrangement (900) having a force generator (903) that comprises a bladder (905). The bladder (905) may be filled with one or more liquids, gases, and/or solids (e.g., saline, silicone, hydroxyethyl starch, succinylated modified fluid gelatin, urea linked gelatin, compounded sodium lactate, balanced salt solution such as PlasmaLyte, and the like). In some variations, the bladder (905) may be at least partially filled with a foam or a gel. The tightening element (901) and bladder (905) are shown in the compressed configuration in FIG. 9A and in the expanded configuration in FIG. 9B. In the compressed configuration, the length of the tightening element (901) (i.e., the longitudinal distance between the proximal end of the housing (916), the end closest to the suture knot (908), and the distal end of the housing (916), the end closest to the suture loop (906)) is less than the length of the tightening element (901) in the expanded configuration. The housing (902) may have a gap that divides the housing into proximal and distal portions (910, 912). During expansion, the distal portion (912) may move distally away from the proximal portion (910), which may increase the length of the tightening element (901) and decrease the size of the suture loop (906). Thus, the proximal and distal ends (914, 916) of the housing may be farther away from each other when the tightening element (901) is in the expanded configuration than when the tightening element (901) is in the compressed configuration.

The size and/or shape of the bladder (905) may change during expansion and compression in order to change the length of the tightening element (901) (i.e., change the distance between the proximal and distal portions (910, 912) of the housing (902)). In some variations, one or more of the materials that fills the bladder (905) and/or comprises a wall or other layer of the bladder (905) may be elastic and biased towards an expanded configuration with a larger size (e.g., volume, surface area). In these variations, compression of the tightening element (901) may decrease the size of one or more of the materials that fills the bladder (905) or comprises a layer of the bladder (905). If unobstructed, the compressed elastic material or materials will tend to expand back to their original sizes, expanding the tightening element (901) in the process.

In other variations, the bladder (905) may change shape when compressed, and its size (e.g., volume, surface area) may or may not change. For example, when the tightening element (901) is compressed by moving the distal and proximal portions (910, 912) of the housing (902) closer together, the bladder (905) may protrude laterally through the gap in the housing (902), as seen in FIG. 9A. Therefore, during compression, the shape of the bladder (905) may change such that its length (i.e., the longitudinal distance between the proximal and distal ends of the bladder) decreases, but its volume and/or surface area may not. The bladder (905) may comprise a frame, wall, or other structure that biases the bladder (905) towards its original shape. Thus, if unobstructed, the bladder (905) may tend to return to its original shape with a greater length, which may increase the length of the tightening element (901) and decrease the size of the suture loop (906). While the expanded shape of the bladder (905) is shown in FIG. 9B as cylindrical, the bladder (905) may comprise any suitable shape (e.g., rectangular prism, sphere, cone). It should be appreciated that the force generator (e.g., bladder, expandable polymer) may change in both size and shape when the tightening element is compressed and expanded.

Housing

In some embodiments, the tightening element may comprise a housing that may cover or enclose at least a portion of the force generator. The housing may have any suitable configuration that allows the tightening element to expand and compress. For example, in some variations, the housing may have an expandable and compressible shape, such as an accordion tube. In other variations, the housing may comprise a material that may expand and compress to accommodate changes in the length of the tightening element. In still other variations, the housing may comprise components that may move relative to each other to allow the tightening element to expand and compress. For example, returning to FIG. 4, the housing (407) may comprise an inner tube (408) at least partially disposed in an outer tube (410). The inner and outer tubes (408, 410) may slide relative to one another, which may accommodate changes in the length of the force generator (406) that may be at least partially housed in the lumens (423, 424) of the inner and outer tubes (408, 410). The force generator may be partially or completely enclosed in the housing, and in some variations, the amount of the force generator enclosed within the housing may vary. For example, a housing may enclose or otherwise cover more of a tightening element when the tightening element is in the compressed configuration than when the tightening element is in the expanded configuration, as may be the case with the housing (902) shown in FIGS. 9A and 9B.

In variations of tightening elements comprising a housing, the housing may serve one or more useful purposes, such as protecting the force generator. For example, a force generator may be sealably enclosed within a housing to isolate the force generator from an environment outside of the housing. This may be advantageous in variations of force generators that comprise materials that may be damaged if exposed to body fluids and/or other materials in the body. In some variations, the housing may shield the force generator from tissue or other material outside of the housing that may interfere with the function of the force generator. For example, the housing may prevent tissue from entering a coil of a compression spring, which could interfere with the compressibility of the spring. In some instances, the housing may also act to protect the tissue or other anatomical structures located near the force generator from catching on or otherwise being damaged by the force generator.

In some variations, the housing may facilitate expansion or compression of a force generator in a specific direction. For example, the inner and outer tubes (408, 410) shown in FIG. 4 may move relative to one another predominantly in a longitudinal direction. This may at least partially restrict the force generator (406) to expansion and compression in a longitudinal direction. In variations of tightening element and suture loop arrangements in which changes in the length (i.e., dimension along the longitudinal axis) of the force generator may change the size of the suture loop, directing the force generator to expand and compress longitudinally may make changes in suture loop size more efficient. In other words, the change in suture loop size (e.g., length of suture forming the suture loop, area within the loop) for a given change in size and/or shape of the force generator may be maximized by directing expansion of the force generator in a longitudinal direction.

As was discussed with respect to FIG. 7, the housing may comprise one or more stops to limit the amount of expansion or compression of a force generator. As the force exerted by a force generator may be related to its change in size (e.g., length, volume), a housing that controls the change in size of the force generator may also control the force that the force generator exerts. This may be advantageous, as compressing a force generator a specified amount, such as until one or more stops block further compression, may result in the force generator exerting a specified force. The tightening element may be configured so that the specified force is a closure force. Thus, the tightening element may be configured to exert a force sufficient to close the left atrial appendage, or other target tissue, through selection of a particular force generator and the use of appropriately placed stops. Therefore, a user may know that if a force generator is released when it is compressed the maximum amount allowed by the housing, then an appropriate closure force may be applied to a target tissue. Put another way, in these variations, a user may be able to better predict the amount of force that will be generated by the force generator and applied to a target tissue upon release of the tightening element at the target tissue prior to a procedure.

As the housing may be the outermost portion of the tightening element, it may comprise one or more features that may engage (e.g., attach to, couple to, contact) other elements of the closure device. For example, the housing may comprise a structure that engages a structure of the elongate body. This engagement may facilitate containment of the tightening element within a specific portion of the elongate body (e.g., a compartment, a recess) and/or release of the tightening element from the elongate body. In some variations, the housing may comprise a feature that may engage a portion of the elongate body to facilitate compression of the tightening element and/or tightening of the suture loop. For example, as depicted in FIGS. 9A and 9B, the housing (902) may comprise a lip (904), which may be used to hold the housing (902) in place when the suture loop (906) is tightened. As will be described in detail herein, the suture loop (906) may be tightened by pulling suture through the suture knot (908) proximally. In order to hold the tightening element (910) stationary and prevent it from also being pulled proximally, a counter force may be applied to the lip (904).

The housing (407) may be made of any suitable material or materials. For example, the housing may comprise one or more biocompatible metals (e.g., titanium, stainless steel, biocompatible alloys) and/or biocompatible polymers (e.g., silicone, polyurethane). For instance, in some variations, the housing (407) may comprise one or more hypotubes and/or one or more thin-walled plastic tubes.

One-Way Mechanism

The suture and/or the tightening element may comprise a one-way mechanism that may have one or more useful functions. For example, the one-way mechanism may direct the expansion of the tightening element in a distal direction, such as by blocking the expansion of the tightening element in a proximal direction. This may ensure that as the tightening element expands, it draws in suture from the suture loop at its distal end and decreases the size of the suture loop. A one-way mechanism may also allow suture to move through or around it in one direction, but may prevent suture from moving through or around it in an opposite direction. For example, the one-way mechanism may allow suture to be pulled through it proximally to decrease the size of the suture loop, while preventing suture from moving through it distally to increase the size of the suture loop. Therefore, there may be at least two ways to decrease the size of a suture loop coupled to a tightening element—the tightening element may expand distally, and/or the suture may be pulled proximally through a one-way mechanism.

A one-way mechanism that allows a suture loop to be tightened independently of changes in the size of the tightening element may provide several benefits. For example, this mechanism may allow for a wider range of suture loop sizes than if the size of the suture loop was only controlled by changes in the size of the tightening element. The change in size of the suture loop due to the tightening element alone may be limited by the change in length of the tightening element. More specifically, as described in more detail herein, the change in length of the suture loop may be about twice as much as the change in length of the tightening element. Given the fact that the tightening element may be implanted in the body, it may be advantageous for the size (e.g., length, volume) of the tightening element to be minimized. This may facilitate advancement into the body and/or minimize inadvertent contact between the tightening element and adjacent anatomical structures. Thus, the properties of a tightening element may be such that its change in length may accommodate only the expected changes in the size of a suture loop after it has been released from the closure device, due to changes in the size of a tissue within the suture loop, for example.

In use, the suture loop may be tightened around a target tissue initially via the one-way mechanism, and subsequently via the tightening element. For example, after the suture loop is positioned around the target tissue, one or more free ends or strands of the suture may be pulled proximally through the one-way mechanism to tighten the suture loop around the tissue. The one-way mechanism may prevent the suture loop from increasing in size, or loosening, over time. When the suture loop and tightening element are released from the closure device, the tightening element may be in the compressed configuration. Any further tightening of the suture loop, such as tightening that may occur if the tissue within the suture loop shrinks, may be accomplished by expansion of the tightening element.

In some variations, the one-way mechanism may allow the tightening element to be compressed by pulling a free end or strand of the suture through the one-way mechanism. For example, when the free end of the suture is pulled proximally through the one-way mechanism, the suture loop size may decrease until the suture loop is tightly around the target tissue. At that point, the tissue within the suture loop may not be compressed further, and the suture loop size may not be decreased further. Pulling the free end of the suture farther proximally in this situation may compress the tightening element between the one-way mechanism and the suture loop. In some variations, using the same mechanism to tighten the suture loop around a tissue and to move the tightening element into a compressed configuration may be advantageous, such as by simplifying the steps of the methods, decreasing the procedure time, and/or simplifying the actuating mechanisms of the closure device.

In some variations, the suture may comprise a one-way mechanism. For example, as seen in FIG. 4, the suture (402) may comprise a one-way suture knot (422) (e.g., a one-way surgical knot, one-way slip knot, Meltzer knot, modified Meltzer knot, Roeder knot, or the like). The suture knot (422) may function as a one-way mechanism by allowing suture (402) to be pulled through the suture knot (422) proximally, but preventing suture (402) from moving through it distally. In addition, the suture knot (422) may block the proximal end of the tightening element (401) from moving proximally over the suture (402), thus directing expansion of the tightening element (401) distally.

In some variations, such as the variation shown in FIG. 6, a first suture (613) may comprise a suture loop (612), and a second suture (615) may comprise a one-way mechanism. For example, in some variations, the second suture (615) may comprise a first knot (610) that is tied around the first suture (613) proximally to the tightening element (601). The first suture (613) may move through the first knot (610), which may be a two-way slip knot, in order to change the size of the suture loop (612). When the suture loop (612) is at a desired size, the second suture (615) may be tied around first suture (613) again to form a second knot (614). The second knot (614), which may be, for example, two half-hitches, may hold the first suture (613) and the first knot (610) in place, thereby preventing proximal movement of the tightening element (601). In this way, the second suture (615) may comprise a one-way mechanism, the first and second knots (610, 614), that directs expansion of the tightening element (601) distally.

In other variations, a first suture may comprise a suture loop and a first knot, and a second suture may comprise a second knot. In these variations, the first knot may be a one-way suture knot, and the second knot may be formed in the vicinity of the first knot to prevent it from loosening or moving. In other words, a second suture and second knot may be used to stabilize a one-way mechanism formed in a first suture. It should be appreciated that any unidirectional locking structure may be positioned in proximity to a suture knot to provide stability to the knot and/or contribute to the function of the one-way mechanism. Examples of unidirectional locking structures, such as beads with teeth, are described in detail in U.S. Pat. No. 9,198,664, entitled "Tissue Ligation Devices and Controls Therefor" and filed on Apr. 1, 2010, which was previously incorporated by reference herein in its entirety.

Figure 10:
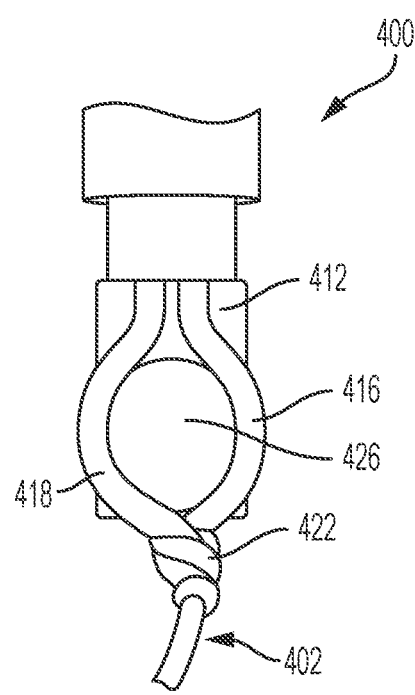
FIG. 10 depicts a proximal portion of a variation of a tightening element and suture loop arrangement.

In variations of one-way mechanisms comprising a suture knot, the tightening element may be configured to orient and/or facilitate the functioning of the suture knot. For example, if the suture knot is centered relative to the proximal end of the tightening element, then the suture knot may be better able to prevent suture from moving through it and/or block expansion of the tightening element in the proximal direction. The tightening element (401) shown in FIG. 4 comprises a proximal cap (412) with a circular hub (426). FIG. 10 shows a magnified view of a proximal portion of the tightening element and suture loop arrangement (400) depicted in FIG. 4, including the proximal cap (412). As seen there, the legs (416, 418) of the suture (402) may extend around opposite sides of the hub (426) and may come together at a proximal portion of its base to form a suture knot (422). Tying the suture knot (422) around a circular structure, such as the hub (426), may facilitate centering of the suture knot (422) relative to the proximal end of the tightening element. Tying the suture knot (422) around the hub (426) may also decrease the chances of the suture knot (422) loosening over time.

In some variations of one-way knots, such as a Meltzer knot, the orientation of the suture legs relative to the knot or the orientation of one suture leg relative to the other suture leg may impact how well the knot locks. A seen in FIG. 10, the legs (416, 418) travel around the hub (426) and approach the suture knot (422) more laterally than if the legs (416, 418) extended straight through the proximal cap (412) to reach the suture knot (422). In other words, the hub (426) may cause the suture legs (416, 418) to approach and/or enter the suture knot (422) at an angle relative to each other, as opposed to the suture legs (416, 418) approaching and/or entering the suture knot (422) in parallel. In some variations, the angle of one suture leg (416) relative to the other suture leg (418) may be any suitable angle greater than zero, including, but not limited to between about 15 degrees and about 180 degrees, between about 45 degrees and about 180 degrees, between about 90 degrees and about 180 degrees, or between about 30 degrees and about 120 degrees. This lateral approach and angled orientation of the legs (416, 418) may help the suture knot (422) remain locked (i.e., decrease the chances that the suture knot (422) will loosen over time). FIG. 7 illustrates another example of a tightening element and suture loop arrangement (700) comprising one suture leg (712) that approaches and enters the suture knot (716) at an angle (e.g., an angle greater than zero, about 90 degrees, between about 30 degrees and about 120 degrees) relative to the other suture leg (714). In this variation, one suture leg (712) extends through the housing (703), and the other suture leg (714) travels outside of the housing (703). In this way, a portion of the housing (703) may separate the suture legs (714) and may prevent them from approaching and entering the suture knot (716) in a parallel orientation.

In some variations, the tightening element may comprise a one-way mechanism, such as a one-way lock. This may be instead of, or in addition to, the suture comprising a one-way mechanism, such as a suture knot. A one-way lock may, for example, be any structure capable of allowing movement of the suture relative to the one-way lock in one direction, but resisting movement in a second direction. In some of these variations, the one-way lock may be placed at least partially around the suture, and it may comprise one or more teeth or projections to allow suture to be advanced through the lock in one direction, but prevent or resist movement of the suture in the opposite direction. In other variations, the one-way lock may be moveable between at least two positions or configurations. In a first position, the one-way lock may allow movement of the suture relative to the one-way lock in one or more directions. In a second position, the one-way lock may resist movement of the suture relative to the one-way lock in one or more directions. It should be appreciated that the tightening element may comprise the one-way lock, or the one-way lock may be a separate element that may be applied with the closure device or a different device. For example, the one-way lock may comprise any unidirectional locking structure, as described in detail in U.S. Pat. No. 9,198,664, entitled "Tissue Ligation Devices and Controls Therefor" and filed on Apr. 1, 2010, which was previously incorporated by reference in its entirety.

Figure 11:
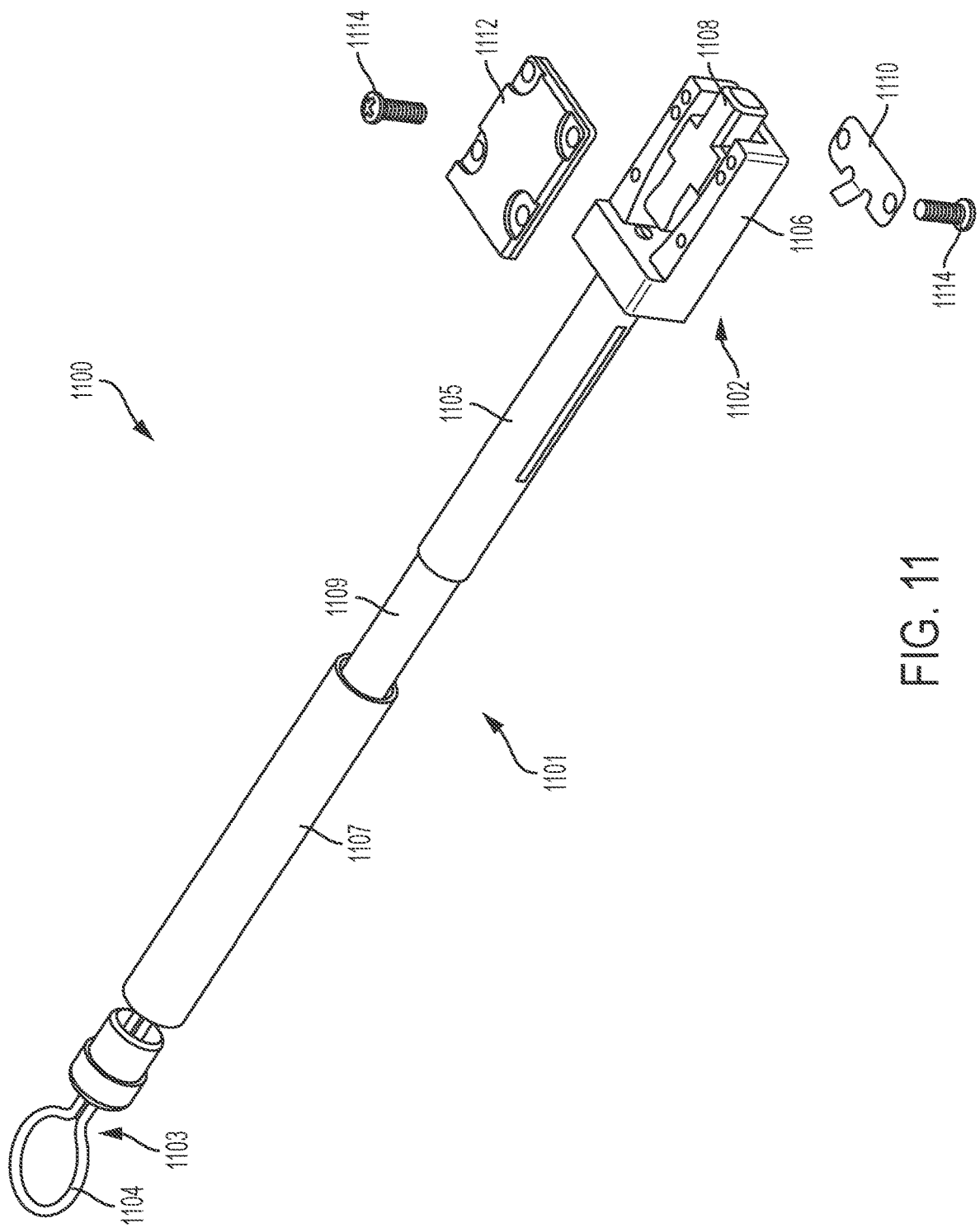
FIG. 11 is an exploded perspective view of a variation of a tightening element and suture loop arrangement comprising a one-way lock.

FIG. 11 depicts a variation of a tightening element and suture loop arrangement (1100) with a tightening element (1101) comprising an inner tube (1105) and an outer tube (1107) at least partially housing a force generator (1109), and a one-way lock (1102). The inner tube, outer tube, and force generator (1105, 1107, 1009) in this embodiment may be similar to the inner tube, outer tube, and force generator (408, 410, 406), respectively, described above with respect to FIG. 4. The tightening element and suture loop arrangement (1100) may not have a suture knot. The one-way lock (1102) may be configured such that suture (1103) may move through it when the one-way lock (1102) is in a first position, but suture (1103) may be prevented from moving through it when the one-way lock (1102) is in a second position (the suture is not shown extending through the one-way lock in FIG. 11). This may allow a user to decrease the size of the suture loop (1104) by pulling suture (1103) proximally through the one-way lock (1102) when it is in the first position. The user may then then move the one-way lock (1102) to the second position to prevent suture (1103) from moving through the one-way lock (1102) to change the size of the suture loop (1104). In addition, when the one-way lock (1102) is in the second position, it may block the proximal end of the tightening element (1101) from moving proximally over the suture (1103). This may direct expansion of the tightening element (1101) distally, which may decrease the size of the suture loop (1104).

Figure 12A:
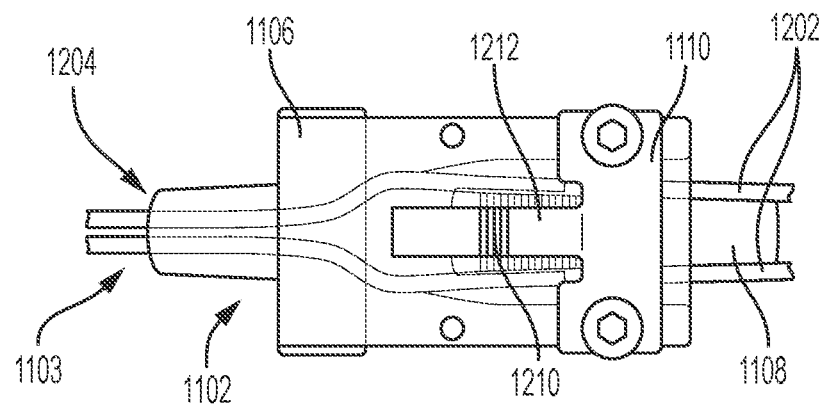
FIGS. 12A and 12B are bottom views of a variation of a one-way lock.
Figure 12B:
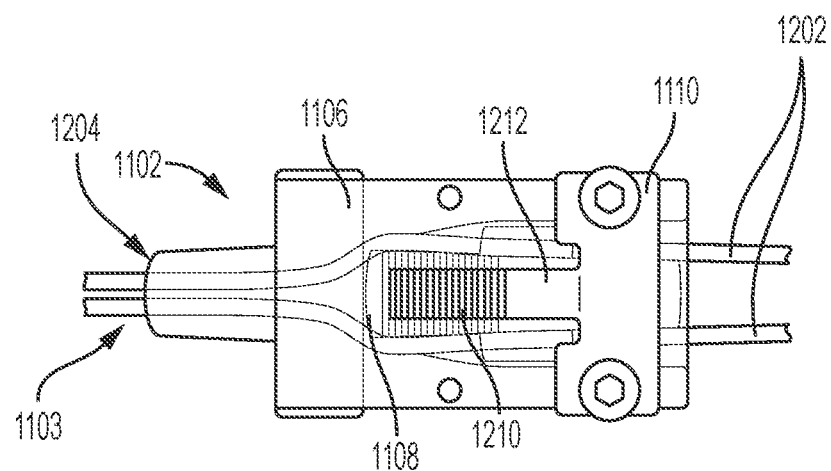
Figure 12C:
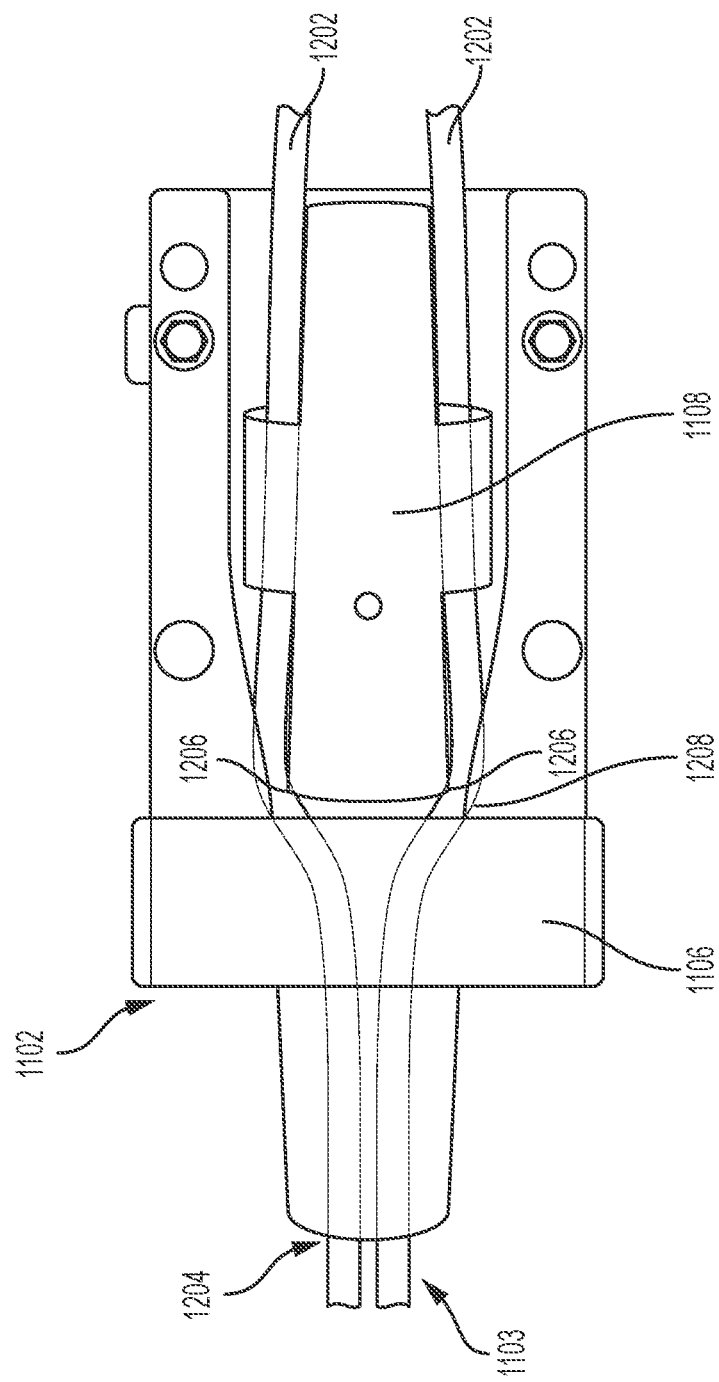
FIG. 12C is a top view of a variation of a one-way lock with a lid removed.

The one-way lock (1102) shown in FIG. 11 comprises a case (1106), a wedge (1108), a leaf spring (1110), and a lid (1112). During assembly, the lid (1112) and the leaf spring (1110) may be attached to opposite surfaces of the case (1106) with screws (1114). FIGS. 12A-12C are magnified views of the one-way lock (1102) shown in FIG. 11, and they illustrate how the one-way lock may interact with strands or ends (1202) of the suture (1103). As shown in the top view in FIG. 12C (the lid has been removed for clarity), the ends (1202) of the suture (1103) may enter a distal opening (1204) in the case (1106), extend around opposite sides of the wedge (1108), and exit through the proximal end of the case (1106). The wedge (1108) may be moveable relative to the case (1106), and the relative positions of the wedge (1108) and the case (1106) may determine the allowable movement of the suture ends (1202) through the one-way lock (1102). When the wedge (1108) is in a first, proximal position relative to the case (1106), as shown in the bottom view in FIG. 12A, there may be sufficient space between the wedge (1108) and the case (1106) for the suture ends (1202) to slide through the one-way lock (1102).

The wedge (1108) may be advanced distally relative to the case (1106) in order to lock the suture ends (1202) between the corners (1206) of the wedge (1108) and the interior walls (1208) of the case (1106). The wedge (1108) is seen in this second, distal position in the bottom and top views of the one-way lock (1102) shown in FIGS. 12B and 12C, respectively. In FIG. 12C, the suture ends (1202) are seen pinched, held, or compressed between the corners (1206) of the wedge (1108) and the interior walls (1208) of the case (1106). When the wedge (1108) is in the distal position, the ends (1202) of the suture (1103) may be locked in place, and the suture (1103) may be prevented from moving through the one-way lock (1102).

The one-way lock (1102) may comprise a mechanism that may allow the wedge (1108) to be pushed into a distal position to lock or hold the suture ends (1202), but may prevent the wedge (1108) from moving proximally to unlock or release the suture ends (1202). For example, as shown in the bottom views of the one-way lock (1102) in FIGS. 12A and 12B, the wedge (1108) may comprise grooves (1210) that may catch (e.g., retain, hold, engage) a tab (1212) of the leaf spring (1110). The tab (1212) may be angled such that it may easily move from one groove (1210) to another as the wedge (1108) is moved distally, but may resist movement out of a groove (1210) if the wedge (1108) tries to move proximally. In use, the suture loop size may be decreased by pulling on the suture ends (1202) while the wedge (1108) is in a proximal position. Once the suture loop is tightly around a tissue and the tightening element is in a compressed configuration, the wedge (1108) may be pushed distally to lock the suture ends (1202) and hold the suture loop tightly around the tissue. The interaction between the grooves (1210) and the tab (1212) may prevent the suture ends (1202) from becoming unlocked.

The one-way lock (1102) depicted in FIG. 11 may comprise any element or combination of elements that may permit the suture (1103) to move through the one-way lock (1102) when the one-way lock (1102) is in the first position and prevent the suture (1103) from moving through the one-way lock (1102) when it is in the second position, and need not comprise the wedge (1108) and leaf spring (1110) depicted in FIG. 11. For example, in some embodiments, the one-way lock (1102) may comprise a compression or torsion spring that may directly or indirectly exert a force against the suture (1103) to lock or otherwise hold it in place. In some variations, the compression or torsion spring may directly replace the wedge (1108) and the leaf spring (1110) (i.e., the compression or torsion spring may be positioned in a similar location as the wedge (1108) and leaf spring (1110)), while in other variations, the one-way lock (1102) may not comprise a wedge and a leaf spring, but the compression or torsion spring may be positioned and/or coupled to the case (1106) differently.

For example, FIG. 24A depicts a cross-sectional side view of a portion of a one-way lock (2400) comprising a case (2402), and a torsion spring (2404) instead of a wedge (1108) and leaf spring (1110). FIG. 24B depicts the torsion spring (2404) removed from the one-way lock (2400). The other elements of the tightening element and suture loop arrangement (1100) are not depicted in FIG. 24A. The torsion spring (2404) may comprise a first leg (2406) and a second leg (2408) and may be positioned on or within the case (2402) such that the first leg (2406) may be fixed relative to the case (2402) and the second leg (2408) may move relative to the case (2402). The case (2402) may comprise a notch or indentation (2410) that may be used to compress, hold, or pinch the suture (2412) between the second leg (2408) and the case (2402). In some variations, the notch or indentation (2410) may be configured such that there is a tight fit between the second leg (2408) of the torsion spring (2404) and the notch or indentation (2410) (e.g., it may have a corresponding shape and/or be sized similarly to the second leg (2408)).

As described above, the one-way lock (2400) may comprise a first position in which the suture (2412) may slide or move through it, and a second position in which the suture may not. In order to transition the one-way lock (2400) from the first position to the second position (shown in FIG. 24A), the one-way lock (2400) may comprise a trigger, for example, a pull wire, rotary element, actuator arm, or the like. More specifically, when the one-way lock (2400) is in the first position, both legs (2406, 2408) may be fixed to or relative to the case (2402) and the torsion spring (2404) may be compressed or otherwise storing energy. Actuating the trigger may release the second leg (2408) of the torsion spring (2404) allowing the torsion spring to expand or otherwise release energy. Once the second leg (2408) is released, it may travel in the direction indicated by the arrow toward and into the notch (2410) in the case (2402) taking the suture (2412) with it. Thus, the suture ends may be compressed, held, or pinched between the second leg (2408) of the torsion spring (2404) and the notch (2410). In some variations, the one-way lock (2400) may comprise two torsion springs, and each torsion spring may compress or hold one suture end.

Figure 25B:
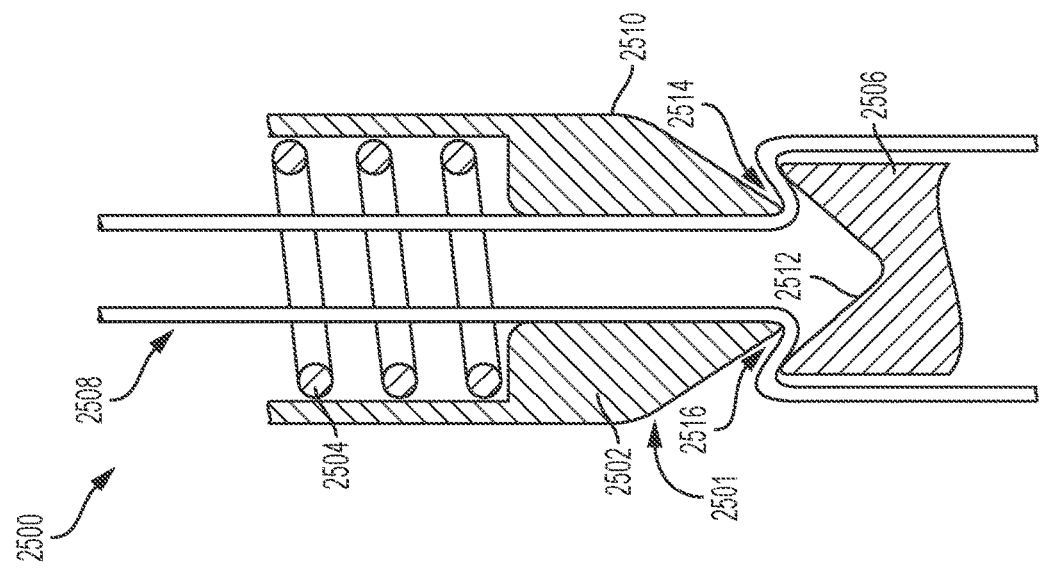
FIGS. 25A and 25B show an embodiment of a tightening element having a one-way suture lock in a first position and a second position, respectively.
Figure 25A:
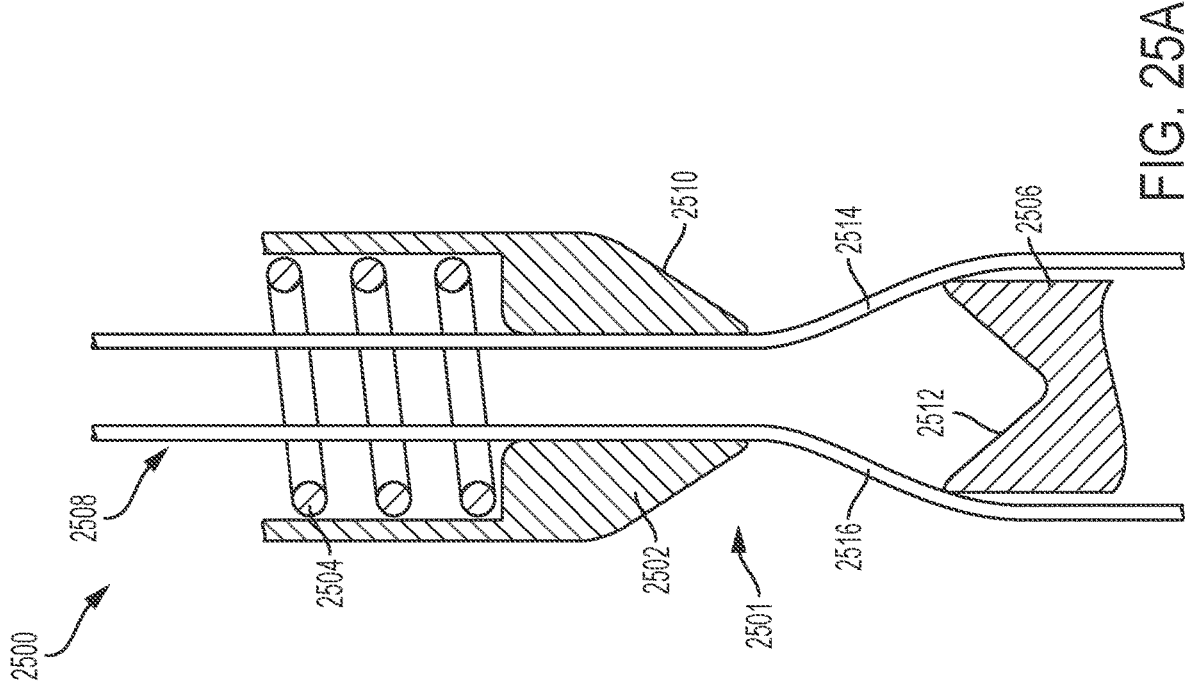

In another variation of the tightening element and suture loop arrangement (1100) depicted in FIG. 11, a single element (e.g., a spring) may be used as both the force generator and in a portion of the one-way suture lock. Put another way, the force generator may be used to both exert a continuous closure force on the tissue via the suture and hold or lock the suture ends. FIGS. 25A and 25B depict a portion of an illustrative variation of a tightening element (2500) with a one-way suture lock (2501) that may form part of the tightening element (1101) depicted in FIG. 11. Shown in FIGS. 25A-25B is a proximal portion of an inner tube (2502), a proximal portion of a force generator (2504) (depicted as a compression spring), a distal portion of a case (2506), and a suture (2508). In this variation, the proximal end of the inner tube (2502) and the distal end of the case (2506) may be configured to mate with one another to compress, hold, or pinch the suture when the one-way suture lock is in the second position. For example, the proximal end of the inner tube (2502) may be configured to fit within an opening in the distal end of the case (2506). In the variation shown in FIGS. 25A-25B, the proximal end of the inner tube (2502) and the distal end of the case (2506) comprise tapers (2510, 2512) or conical sections, however, the proximal end of the inner tube (2502) and the distal end of the case (2506) may have complementary ends that are domed, square, rectangular, or the like.

Similarly to the one-way suture locks previously described, the one-way suture lock (2501) may comprise a first position in which the suture (2508) may move through (e.g., through a lumen) and/or around it (shown in FIG. 25A), and a second position in which the suture (2508) may be locked or held in place (shown in FIG. 25B). Additionally, the tightening element (2500) may also comprise a trigger that may allow the one-way suture lock (2501) to move from the first position to the second position. For example, when the one-way suture lock (2501) is in the first position, the force generator (2504) may be compressed or otherwise storing energy. Actuating the trigger may release the force generator (2504) and allow it to expand longitudinally or otherwise release energy. Once the force generator (2504) is released, it may push the proximal portion of the inner tube (2502) toward the distal portion of the case (2506) thereby compressing, holding, or pinching the suture strands (2514, 2516) between the tapers (2510, 2512) of the inner tube (2502) and the case (2506). Additionally, when the force generator (2504) is released, it may also push the outer tube (not depicted) distally toward the suture loop such that a closure force is applied to the tissue. Thus, in the second position, the force exerted by the force generator (2504) may be used for two purposes: 1) to lock one or both suture strands (2514, 2516) and 2) to apply a continuous closure force to the tissue.

Figure 13:
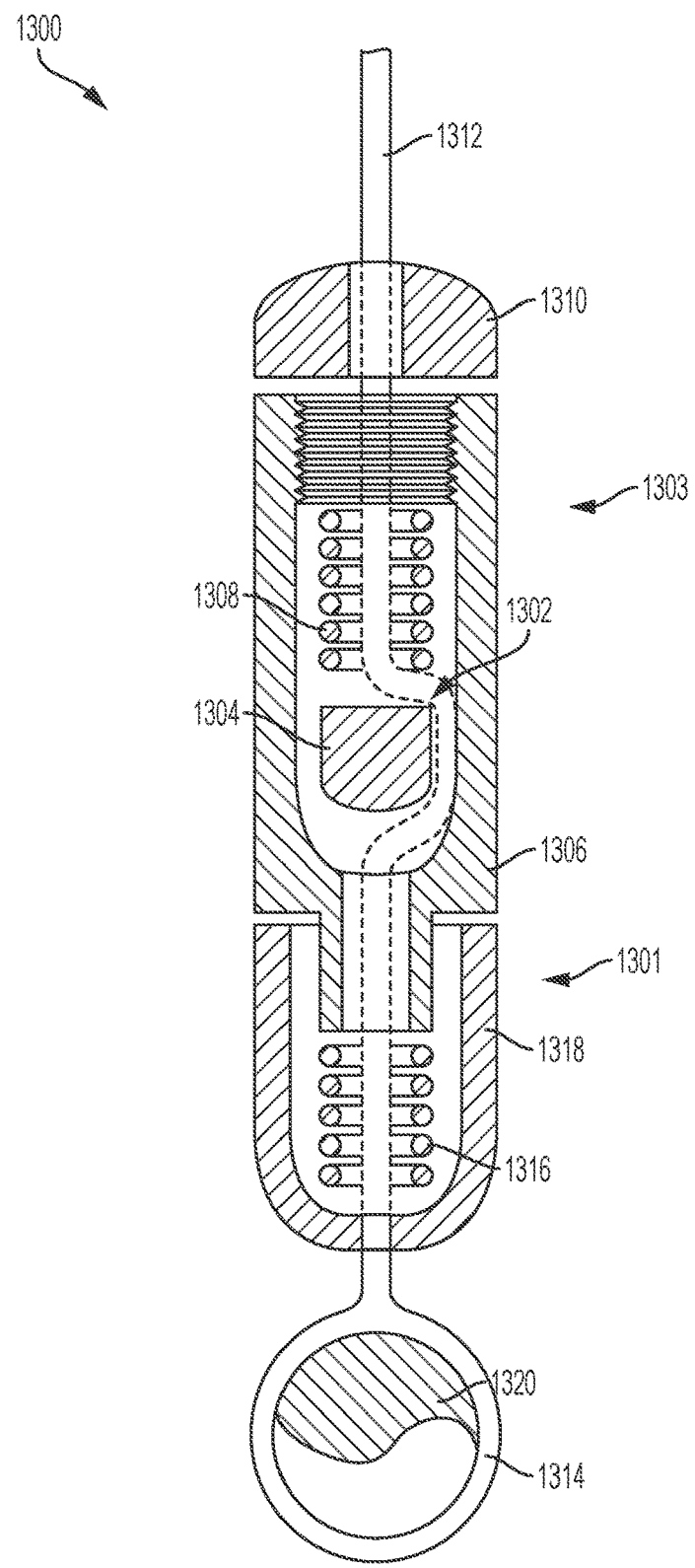
FIG. 13 depicts a variation of a tightening element and suture loop arrangement described here having a one-way lock comprising a brake pad.

The tightening element and suture loop arrangement (1300) shown in FIG. 13 is another variation of a tightening element (1301) comprising a one-way lock (1303). In this variation, the one-way lock (1303) may comprise an inner tube (1306), a first force generator (1308) (shown as a compression spring), a brake pad (1304), and a preload mechanism (1310), and the tightening element (1301) may comprise an outer tube (1318) housing a second force generator (1316) (also depicted as a compression spring). The first force generator (1308) may be positioned within the inner tube (1306) between the brake pad (1304) and the preload mechanism (1310) (e.g., a preload screw or the like) and the second force generator (1316) may be positioned within the outer tube (1318) between a distal portion of the inner tube (1306) and the distal portion of the outer tube (1318).

When the lock (1303) is engaged (i.e., in the second position), the suture (1302) may be pressed between the brake pad (1304) and an inner wall of the inner tube (1306) to prevent movement of the suture (1302) through the one-way lock (1303). The first force generator (1308) may exert a force on the brake pad (1304), which may push against the suture (1302). Adjusting the preload mechanism (1310) (e.g., screwing the preload screw into or out of the inner tube (1306)) may adjust the length of the first force generator (1308) and therefore, change the amount of force that it produces. In this way, the force the brake pad (1304) applies to the suture (1302) can be adjusted.

For example, referring to the variation shown in FIG. 13 with a preload mechanism comprising a preload screw, the preload screw may be advanced farther into the inner tube (1306) to decrease the length of the first force generator (1308). This may increase the force that is produced by the first force generator (1308), and thereby increase the force that the brake pad (1304) applies to the suture (1302). This increased force may be large enough to prevent the suture (1302) from moving through the suture lock (1303) between the brake pad (1304) and the inner tube (1306), and may therefore prevent the size of the suture loop (1314) from changing. In other words, the suture (1302) may move through the suture lock (1303) when the one-way lock is in the first position (when the preload mechanism (1310) is in a proximal position relative to the inner tube (1306)), and the suture (1302) may be prevented from moving through the suture lock (1303) when the one-way lock is in the second position (when the preload mechanism (1310) is in a distal position relative to the inner tube (1306)). In other variations, the preload mechanism (1310) may be at a desired position before the suture ends (1312) are pulled to tighten the suture loop (1314). In these variations, pulling the suture ends (1312) proximally may compress the first force generator (1308), allowing the suture (1302) to be pulled past the brake pad (1304). When the suture ends (1312) are released, the first force generator (1308) may expand, locking the suture (1302) between the brake pad (1304) and the inner tube (1306) and preventing the suture (1302) from moving relative to the inner tube (1306).

In use, the suture ends (1312) may be pulled proximally through the tightening element (1301) and the one-way lock (1303) to tighten the suture loop (1314) around a tissue (1320), and the tightening element and suture loop arrangement (1300) may be advanced distally toward the tissue (1320). The outer surface of the outer tube (1318) may contact the tissue (1320), which may prevent the outer tube (1318) from advancing further. The inner tube (1306) may continue to be advanced, which may compress or load the second force generator (1316). Once the suture loop (1314) has been tightened around the tissue and the second force generator (1316) has been compressed or loaded a desired amount (e.g., an amount sufficient to exert a continuous closure force on the tissue (1320)), the one-way lock (1303) may be moved from the first position to the second position to hold the tightening element and suture loop arrangement (1300) in place and to prevent the suture loop (1314) from enlarging. Because the tightening element (1301) is sandwiched between the tissue (1320) and the now fixed inner tube (1306), it may exert a continuous closure force on the tissue (1320) via the suture loop (1314), as described in more detail with respect to FIGS. 5A-5C.

Figure 14:
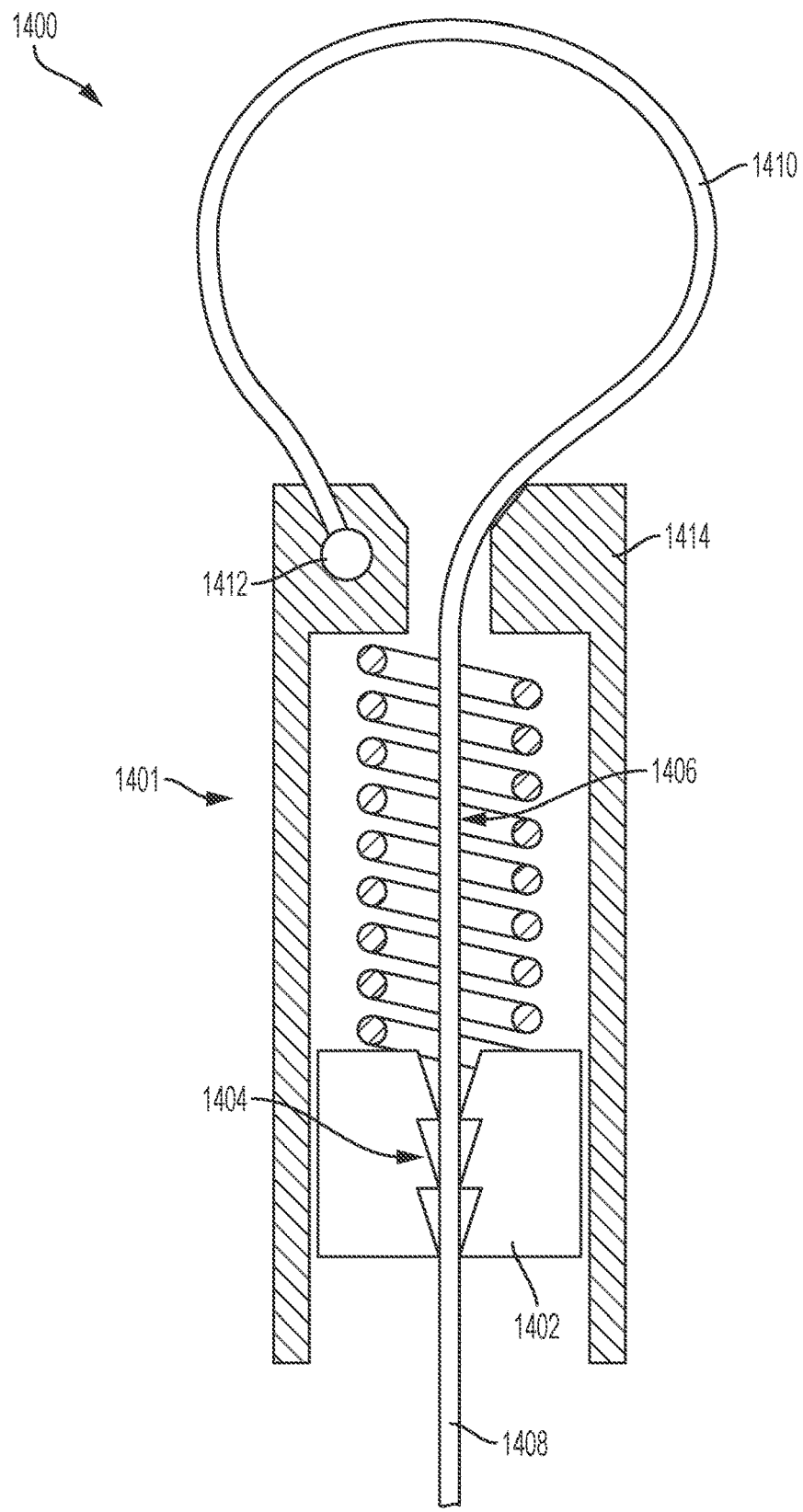
FIG. 14 shows a variation of a tightening element and suture loop arrangement described here having a one-way lock comprising teeth.

FIG. 14 depicts a tightening element and suture loop arrangement (1400) comprising a tightening element (1401) with another variation of a one-way lock (1402). In this variation, the one-way lock (1402) may comprise teeth (1404), which may engage the suture (1406) as it extends through the one-way lock (1402). The angle of the teeth (1404) relative to the suture (1406) may allow the suture (1406) to be pulled proximally through the one-way lock (1402), but the teeth (1404) may catch or otherwise stop the suture (1406) from moving distally through the one-way lock (1402). Thus, the suture (1406) may be pulled proximally to tighten the suture loop (1410), but the one-way lock (1402) may prevent the suture loop (1410) from increasing in size or loosening. The teeth (1404) may also prevent the one-way lock (1402) from moving proximally over the suture (1406). Thus, during expansion of the tightening element (1401), the one-way lock (1402) may remain stationary while the distal end of the tightening element (1401) may move distally to decrease the size of the suture loop (1410).

While two ends of the suture may extend through the one-way lock (as seen in FIGS. 12A-12C), this need not be the case. FIG. 14 illustrates a variation of tightening element and suture loop arrangement (1400) where only a portion of a suture (1406) (e.g., one strand, end) travels through the one-way lock (1402). In this embodiment, the suture (1406) may comprise a fixed end (1412) and a free end (1408). The fixed end (1412) may be attached to a portion of the tightening element (1401) (e.g., a portion of the housing (1414)), and the free end (1408) may be adjusted (e.g., moved proximally or distally relative to the one-way lock (1402)) to control the size of the suture loop (1410). Additionally, while FIG. 14 illustrates the tightening element (1401) in use with a suture (1406), the tightening element (1401) may be used with a snare instead of the suture (1406).

Figure 26A:
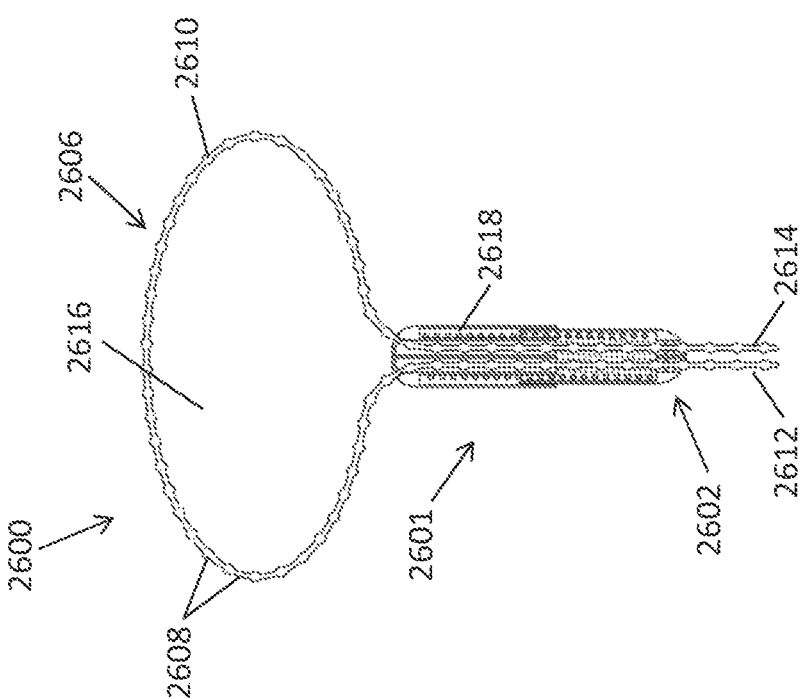
FIGS. 26A-26C illustrate cross-sectional side views of a variation of a tightening element and snare loop arrangement in expanded, fully compressed, and partially compressed configurations, respectively.
Figure 26B:
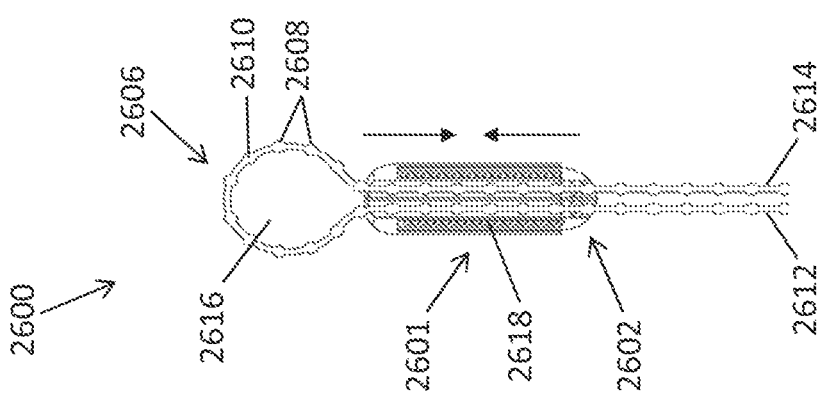
Figure 26C:
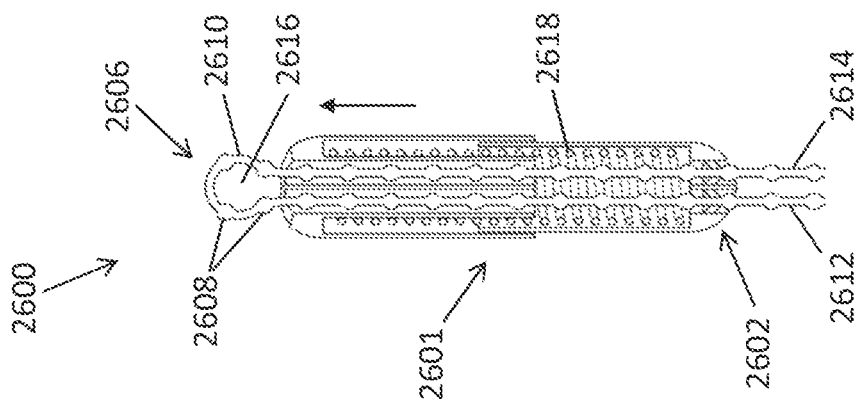

As mentioned above, some of the closure devices described here may comprise a tightening element and snare loop arrangement instead of a tightening element and suture loop arrangement. FIGS. 26A-26C depict a variation of a tightening element and snare loop arrangement (2600) comprising a tightening element (2601) with a one-way lock (2602) that may be used in the closure devices described here. In this variation, the snare (2606), including the snare loop (2610) with aperture (2616) and the snare ends (2612, 2614), may comprise protrusions (2608) along its length that may interact with the one-way lock (2602) to tighten the snare loop (2610) around tissue and hold the tightening element and snare loop arrangement (2600) in place. The one-way lock (2602) may allow the protrusions (2608) (and thus the snare (2606)) to move proximally through it, but not distally. For example, the one-way lock (2602) may comprise internal surfaces or structures that allow the protrusions to pass proximally through the one-way lock (2602), but block or otherwise stop the protrusions from moving distally. Thus, the snare (2606) may be pulled proximally to tighten the snare loop (2610), but the one-way lock (2602) may prevent the snare loop (2610) from increasing in size or loosening. The one-way lock (2602) may also prevent the tightening element and snare loop arrangement (2600) from moving proximally over the snare (2606). While depicted as spherical, the protrusions (2608) may have any suitable shape. Additionally, the protrusions (2608) may be formed integrally with the snare (2606), or they may be formed separately and coupled to the snare (2606). In some variations, the protrusions (2608) may not be disposed along the entire length of the snare (2606), and instead, they may be strategically placed along the snare (2606) only at locations expected to pass through the one-way lock (2602) or at locations corresponding to a particular snare loop (2610) size or closure force.

FIGS. 26A, 26B, and 26C show the tightening element (2601) in an expanded configuration (before deployment), a fully compressed configuration (during and/or after snare loop tightening), and a partially compressed configuration (after tissue remodel), respectively. In use, the snare loop (2610) may be advanced to and around a target tissue (tissue not depicted). The snare ends (2612, 2614) may then be held stationary while the tightening element (2601) is advanced distally toward the target tissue, thereby decreasing the size (e.g., diameter, circumference, area) of the aperture (2616) and tightening the snare loop (2610) around the tissue. Advancing the tightening element (2601) may also compress the force generator (2618), as indicated by the arrows in FIG. 26B, which may be held in a compressed and/or partially compressed position by the interaction between the one-way lock (2602) and the protrusions (2608) on the snare (2606). Put another way, after the force generator (2618) is compressed, the one-way lock (2602) may prevent one or more protrusions (2608) from moving distally of the one-way lock (2602), which may prevent the proximal end of the tightening element (2601) and the force generator (2618) from moving in a proximal direction. Thus, the force generator (2618) may exert a continuous closure force on the target tissue via the snare loop (2610) and the distal end of the tightening element (2601). The snare (2606) may then be severed or otherwise released from the closure device, leaving the snare loop (2610) and the tightening element (2601) at the tissue. If the size of the tissue within the aperture (2616) of the snare (2610) decreases (e.g., the tissue thins, remodels, or otherwise decreases), the force generator (2616) may expand (as depicted in FIG. 26C), moving the distal end of the tightening element (2601) distally toward the remaining tissue (as indicated by the arrow in FIG. 26C). This may result in a decrease in the size of the aperture (2616) and maintenance of the closure force on the tissue. In some variations, to tighten the snare loop (2610) and/or compress the force generator (2618), one or both of the snare ends (2612, 2614) may be pulled proximally while the tightening element (2601) is held stationary.

FIGS. 27A and 27B illustrate another variation of a tightening element and snare loop arrangement (2700) comprising a tightening element (2701) with a snare lock (2702), and a snare (2706) comprising a snare loop (2710) and snare ends (2724). In some variations, the tightening element (2701) may be similar to the tightening element (2601) described with respect to FIG. 26, but it may comprise a different snare lock (2702). In this variation, the tightening element (2701) may comprise an outer tube (2708), an inner tube (2710) configured to at least partially fit inside the outer tube (2708), a force generator (2712), and a snare lock (2702). The force generator (2712) may be positioned within and between the inner tube (2710) and outer tube (2708) and may be configured to apply a continuous closure force to tissue via the snare (2706).

In this variation, the snare lock (2702) may be similar to a vise or collet. As shown in the exploded view in FIG. 27B, the snare lock (2702) may comprise a body (2714) coupled to or formed integrally with the inner tube (2710) of the force generator (2712), a collar (2716), and a cap (2718). The collar (2716) may be at least partially disposed within a lumen of the body (2714) and may be coupled to the cap (2718). The collar (2716) may be configured to hold one or both of the snare ends (2724). In use, the cap (2718) may be used to move the snare lock (2702) between a first, disengaged position and a second, engaged position.

As mentioned above, the collar (2716) may be configured to hold one or both of the snare ends (2724), which may prevent the snare ends (2724) from advancing or retracting when the lock (2702) is engaged. The collar (2716) may have a proximal portion (2720) comprising a lumen with a fixed size (e.g., diameter) and a distal portion (2722) comprising a lumen with an adjustable size (e.g., diameter). Moving the snare lock (2702) from the first position to the second position may change the size of the lumen in the distal portion (2722) of the collar (2716).

For example, in the embodiment depicted in FIGS. 27A-27B, when the snare lock (2702) is in the first position, the diameter of the lumen in the distal portion (2722) of the collar (2716) may be greater than the combined diameters of the snare ends (2724). Accordingly, in the first position, the snare (2706) may move freely through the collar (2716) and thus the snare lock (2702). When the snare lock (2702) is in the second position, the diameter of the lumen in the distal portion (2722) of the collar (2716) may be less than or equal to the combined diameters of the snare ends (2724). Thus, in the second position, the snare (2706) may be pinched or held by the distal portion (2722) of the collar (2716) such that it may no longer advance or retract freely. In variations in which the snare lock (2702) only holds one snare end (for example, because the other snare end is fixed), the diameter of the lumen of the distal portion (2722) of the collar (2716) may be less than or equal to the diameter of one snare end when the snare lock (2702) is in the second position. In some instances, the diameter of the lumen in the distal portion (2722) of the collar (2716) may not be uniform along the length of the lumen. In these variations, the diameter of the distal end of the distal portion (2722) may be less than or equal to the diameter of the snare end(s) such that the snare (2706) may be pinched or held at the distal end of the distal portion (2722). In some variations, the collar (2716) may comprise a contact surface on an internal surface (i.e., inside the lumen) of the distal portion (2722) that may be configured to assist with holding the snare (2706). For example, in some instances, the contact surface may be textured and/or carry an adhesive.

In some variations, the distal portion (2722) of the collar (2716) may comprise or be formed from a plurality of arms or jaws, as depicted in FIG. 27B. Although the collar (2716) is depicted comprising arms that circumferentially surround the snare ends (2724), this need not be the case. For example, in some variations, the collar (2716) may comprise arms that only partially circumferentially surround the snare ends (2724). The collar (2716) may comprise any suitable number of arms, for example, two, three, four, or more. In some variations, all of the plurality of arms may be moveable between the first position, in which the snare (2706) may advance distally and proximally through the arms, and the second position, in which the arms contact (e.g., grasp, grip, hold) the snare (2706) and prevent it from advancing or retracting. In other variations, one or more of the plurality of arms may be fixed, while one or more of the remaining arms may be moved into and out of contact with the snare (2706).

In use, the cap (2718) may be moved proximally or distally with respect to the body (2714) of the snare lock (2702) to engage and disengage the snare lock (2702). In some variations, the cap (2718) may be rotatably coupled to the body (2714) such that when the cap (2718) is rotated in a first direction, the diameter of the lumen in the distal portion (2722) of the collar (2716) may decrease, and when the cap (2718) is rotated in a second, opposite direction, the diameter of the lumen in the distal portion (2722) of the collar (2716) may increase. In other variations, the cap (2718) may be slideably coupled to the body (2714), such that when the cap (2718) is pressed or otherwise moved toward the body (2714), the diameter of the lumen in the distal portion (2722) of the collar (2716) may decrease, and when the cap (2718) is pulled or otherwise released proximally, the diameter of the lumen in the distal portion (2722) of the collar (2716) may increase. In this way, rotating, pressing or otherwise actuating the cap (2718) may move the distal portion (2722) of the collar (2716) into and out of contact with the snare (2706), which may move the suture lock (2702) between the first, disengaged position and the second, engaged position.

Figure 15:
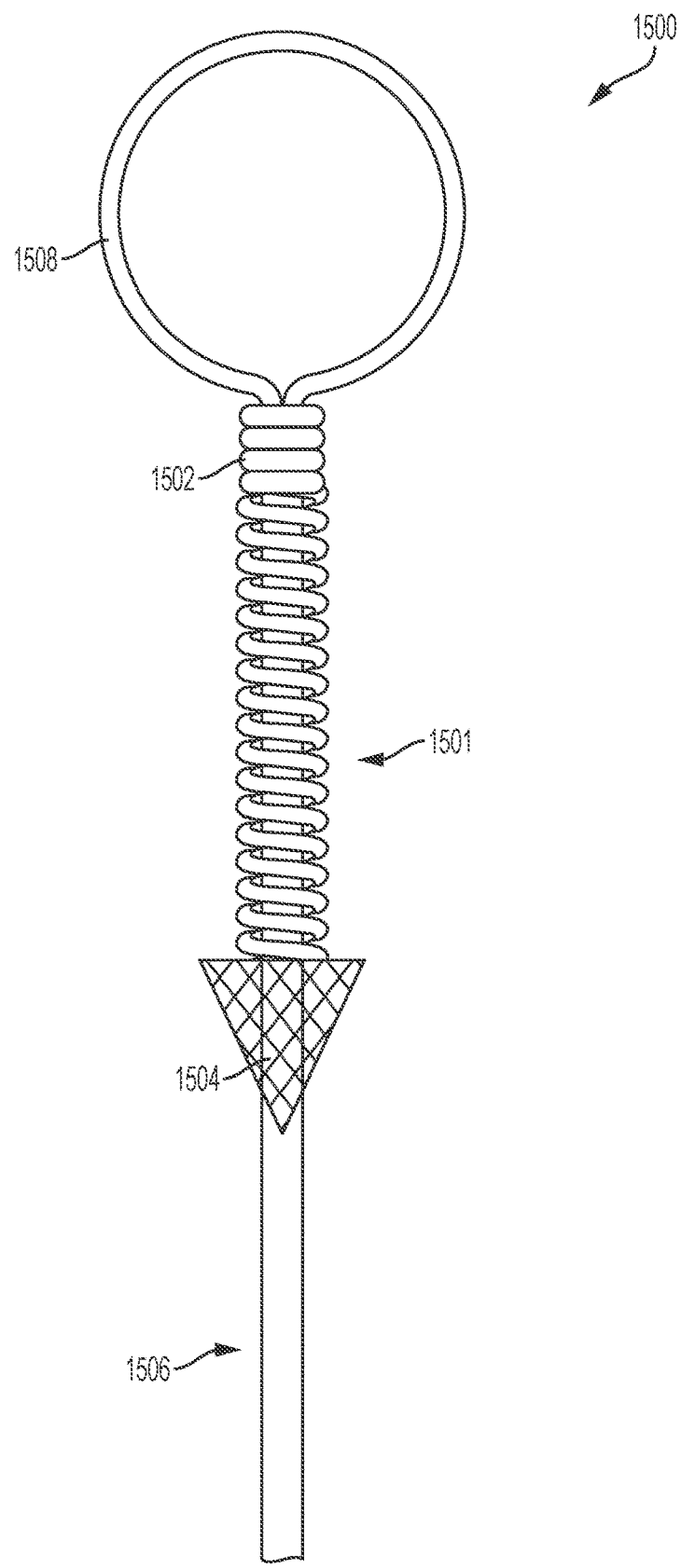
FIG. 15 illustrates a variation of a one-way mechanism described here comprising a one-way lock and a suture knot.

In some embodiments, a one-way mechanism may comprise both a one-way lock and a suture knot. In these embodiments, the suture knot may allow suture to move through it in one direction (i.e., a one-way suture knot) or in two directions (i.e., a two-way suture knot). FIG. 15 depicts a variation of a tightening element and suture loop arrangement (1500) comprising both a one-way lock (1504) and a suture knot (1502). In this embodiment, the tightening element (1501) may be positioned proximal to the suture knot (1502). The tightening element (1501) may comprise the one-way lock (1504), which may be configured such that the suture (1506) may be pulled proximally through the one-way lock (1504), but it may be prevented from moving distally through the one-way lock (1504) (e.g., the one-way lock may comprise teeth, as discussed with regards to FIG. 14). Alternatively, the one-way lock (1504) may be moveable between a first position that allows suture (1506) to move through the one-way lock (1504) and a second position that prevents suture (1506) from moving through the one-way lock (1504). The one-way lock (1504) may also be configured such that it may not slide proximally over the suture (1506), which may prevent the tightening element (1501) from expanding in a proximal direction. Thus, during expansion, the tightening element (1501) may expand distally and push against the suture knot (1502).

The suture knot (1502) may be configured to allow suture (1506) to be pulled proximally through it. Therefore, during expansion, the tightening element (1501) may cause suture (1506) to be pulled proximally through the suture knot (1502), effectively pushing the one-way suture knot (1502) distally to decrease the size of the suture loop (1508). In some variations, the suture knot (1502) may be a one-way suture knot, such that suture (1506) may move proximally through it, but suture (1506) may be prevented from moving distally through it. A one-way suture knot may allow the suture loop (1508) to be tightened, but may prevent the suture loop (1508) from being loosened. In other variations, the suture knot (1502) may be a two-way suture knot, which may allow suture (1506) to move both proximally and distally through it. In these variations, the size of the suture loop (1508) may also be prevented from increasing. For example, the force of the tightening element (1501) pushing distally on the suture knot (1502) may prevent the suture knot (1502) from moving proximally over the suture (1506) to increase the size of the suture loop (1508). It should be appreciated that any of the tightening elements described herein may be positioned proximal to a suture knot to effectively function as a knot pusher.

If two strands or free ends of a suture or snare travel through a one-way mechanism (for example, the one-way lock (1201) seen in FIGS. 12A-12C), then one free end or both free ends may be adjusted to change the size of the suture loop or snare loop. For example, if both free ends of the suture or snare are pulled proximally through the one way-mechanism together, then both legs, or sides, of the suture loop or snare loop may be pulled into the tightening element the same amount. In this way, the suture loop or snare loop may decrease in size symmetrically. However, if only one free end is pulled through a one-way mechanism, then only one leg, or side, of the suture loop or snare loop may be drawn into the tightening element, and the suture loop or snare loop may decrease in size asymmetrically. This may occur in variations of tightening element and suture or snare loop arrangements that only have one free suture or snare end, like the arrangements (400, 1400) seen in FIGS. 4 and 14, or in variations of tightening element and suture or snare loop arrangements that have two free suture or snare ends, but where only one of the free ends is pulled.

The tightening elements, suture, and/or snare described herein may be at least partially housed in any suitable portion or portions of the closure device prior to the release of the tightening element and the suture or snare at a target tissue. For example, the tightening element may be at least partially housed in a lumen, recess, or compartment of the elongate body, as will be described in more detail herein. In some variations, the tightening element may be held in a compressed configuration while at least partially housed within the closure device. For example, the tightening element may be housed in a compartment that may have a length less than the length of the tightening element when it is in an expanded configuration. The tightening element may therefore be restricted from expanding while housed in the compartment. In some variations, the tightening element may be moved from an expanded configuration to a compressed configuration while it is at least partially housed in the closure device. In other variations, the tightening element may be moved into a compressed configuration after it is released from the closure device.

Similarly, a suture or snare may be at least partially housed in a lumen, recess, or compartment of the elongate body. In some variations, one portion of the suture, such as the suture knot, or portion of the snare may be positioned in a lumen, recess, or compartment of the elongate body, and another portion of the suture or snare may be housed in a different lumen, recess, or compartment. In variations comprising a suture, as may be the case with the tightening element, it may be advantageous for the suture knot to be held stationary relative to the elongate body while the size of the suture loop is changed. A portion of the elongate body may provide a counterforce on the tightening element, and in variations comprising a suture, the suture knot, while an end of the suture/snare is pulled proximally to tighten the suture or snare loop.

One or more strands or ends of the suture or snare may extend from the suture or snare loop into the elongate body, and the one or more strands or ends may be at least temporarily secured to a portion of the elongate body or a portion of the handle. In some variations, as was discussed with respect to FIG. 2B, the suture loop and/or the tightening element may be at least temporarily coupled to the snare. In some of these variations, changing the size of the snare loop may change the size of the suture loop. For example, a suture loop may be temporarily coupled to a snare by an element comprising two lumens, one for the snare and one for the suture loop. Examples of such elements, or retention members, are described in detail in U.S. Pat. No. 8,771,297, entitled "Devices, Systems, and Methods for Closing the Left Atrial Appendage" and filed on Mar. 25, 2008, and U.S. Pat. No. 9,198,664, entitled "Tissue Ligation Devices and Controls Therefor" and filed on Apr. 1, 2010, which were previously incorporated by reference in their entirety. The documents incorporated by reference above also describe suitable materials for the suture that may be used in some embodiments of the closure devices described herein.

Tightening Element Comprising an Aperture

The previously described variations of tightening elements may be coupled to a suture comprising a suture loop or a snare comprising a snare loop, and these elements may be configured such that the suture loop or snare loop encircles and applies the majority of the closure force to the target tissue. In contrast, in other variations, the tightening element itself may encircle and directly apply the majority of the closure force to the target tissue. In these variations, the tightening element may comprise an aperture, through which the target tissue may be at least partially positioned. The tightening element may be configured such that a change in its shape and/or size (e.g., volume, surface area) may change the aperture size (e.g., area within the aperture, volume within the aperture, diameter of the aperture). If a tissue within the aperture shrinks (e.g., there's a decrease in the area of tissue within the aperture, a decrease in the volume of tissue within the aperture), the size and/or shape of the tightening element may change, which may decrease the size of the aperture and maintain a continuous closure force on the tissue.

FIGS. 16A and 16B provide an illustrative example of a tightening element (1600) comprising an aperture (1602). In this embodiment, the tightening element (1600) may form a loop that may at least partially define an aperture (1602). The tightening element (1600) may comprise a force generator (1604), which may expand radially to decrease the size of the aperture (1602). FIG. 16A shows the force generator (1604) in a compressed configuration, and FIG. 16B shows the force generator (1604) in an expanded configuration. It should be appreciated that when the force generator (1604) is in a compressed or an expanded configuration, the tightening element (1600) is also in a compressed or an expanded configuration, respectively. The arrows in FIG. 16A indicate the radial direction of expansion of the force generator (1604), and may indicate the direction of the force produced by the force generator (1604). As the force generator (1604)

expands, the size (e.g., area, circumference, diameter, etc.) of the aperture (1602) may decrease. When the tightening element (1600) is released from the closure device, the aperture (1602) may be positioned tightly around a tissue, and the force generator (1604) may be in a compressed configuration. In the compressed configuration, the force generator (1604) may apply a continuous closure force to the tissue. If the tissue within the aperture (1602) shrinks or thins (e.g., there is a decrease in the area, volume, amount) over time, the force generator (1604) may radially expand to decrease the size of the aperture (1602) and keep the tissue closed.

A tightening element (1600) configured as shown in FIGS. 16A and 16B may comprise any force generator (1604) that, when radially compressed, tends or is biased to expand back to its original size and/or shape. The force generator (1604) may store mechanical energy when radially compressed, and this may allow it to radially expand and exert a closure force on a tissue at least partially within the aperture (1602) of the tightening element (1600) (e.g., in the plane of the aperture and inside of the boundaries of the aperture (1602)). In some variations, the force generator (1604) may comprise an expandable polymer (e.g., ePTFE, rubbers, silicone, urethanes, hydrogels, biogels, bio based elastomers, polylactic acid, and the like). In these variations, the expandable polymer may have any suitable shape or configuration, such that it may radially expand to decrease the size of the aperture (1602).

As shown in FIGS. 16A and 16B, the force generator (1604) may be coupled to a suture (1606) comprising a suture knot (1608). The suture knot (1608) may be formed by tying together two suture ends. In some variations, these ends may be the ends of one suture that may extend through a lumen or channel of the force generator (1604). In other variations, the ends may be from two separate sutures that may be attached to opposite sides of the force generator (1604). In either variation, the suture knot (1608) may be a one-way suture knot (e.g., a Meltzer knot), as described above, and may allow the size of the aperture (1602) to be adjusted independently of changes in the size of the force generator (1604).

Figure 17C:
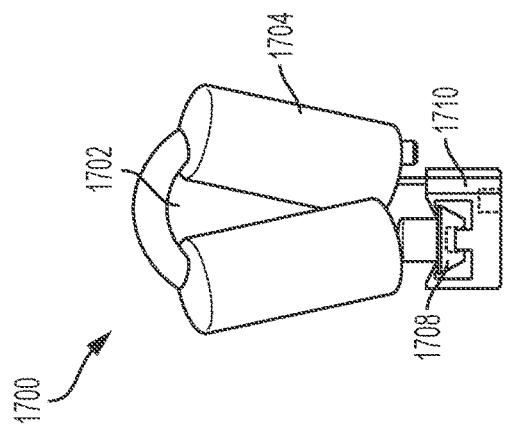
FIG. 17C depicts a variation of a tightening element separated from the elongate body.
Figure 17B:
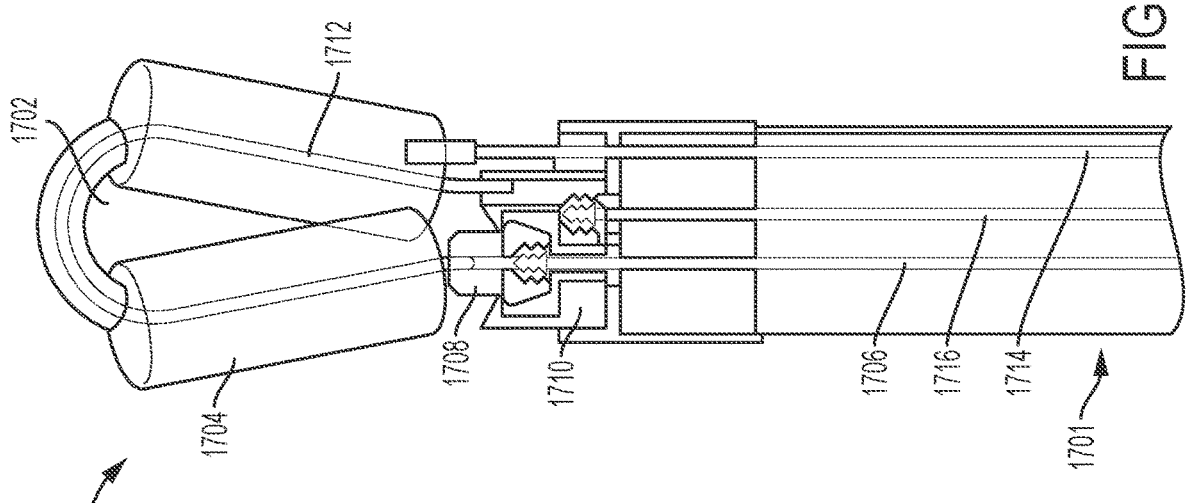
FIGS. 17A and 17B show a variation of a tightening element described here having an aperture and comprising a balloon in a deflated configuration and an inflated configuration, respectively.
Figure 17A:
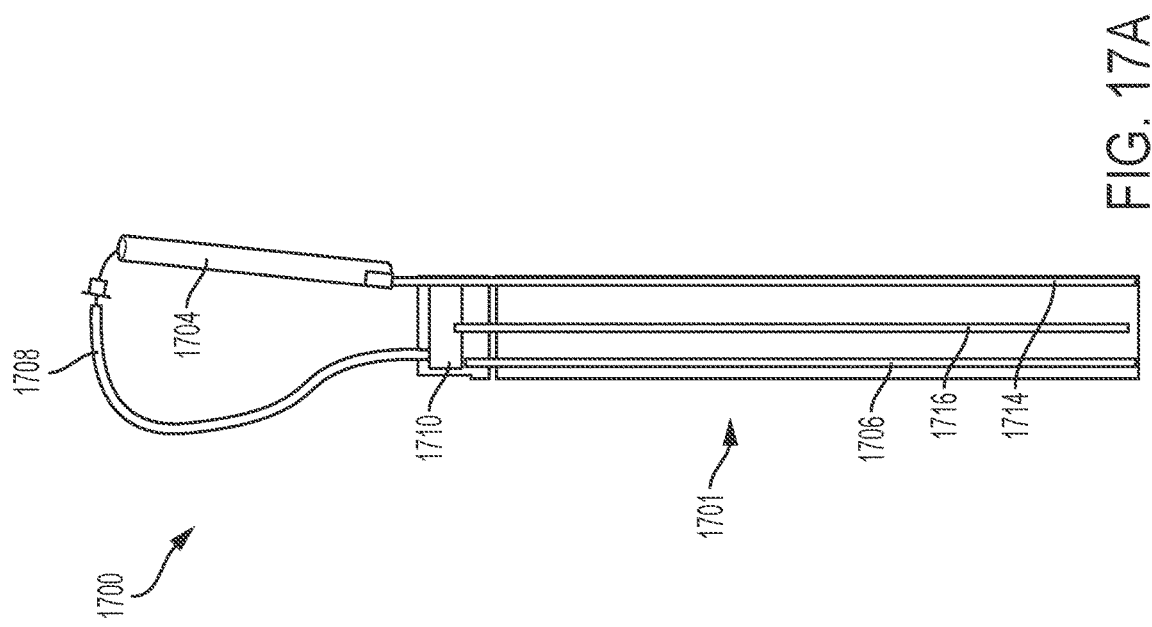

FIGS. 17A-17C illustrate another example of a tightening element (1700) comprising an aperture (1702) and configured to radially compress and expand. In this embodiment, the force generator may comprise a balloon (1704) that may be at least partially filled with a compressible material. In some variations, the balloon (1704) may be filled with one or more solids (e.g., a foam), liquids (e.g., saline), and/or gases (e.g., ambient air). It may be advantageous for the balloon (1704) to be at least partially filled with a gas or a liquid, as this may facilitate inflation, or filling, of the balloon (1704). The balloon (1704) may be made from any suitable biocompatible material, such as polyvinyl chloride, polyethylene terephthalate, or nylon.

FIG. 17A shows the balloon (1704) in a deflated configuration, and FIGS. 17B and 17C show the balloon (1704) in an inflated configuration. When the balloon (1704) is in the deflated configuration, it may be easier for the balloon (1704) to be at least partially housed in the elongate body (1701) and be delivered to a target tissue. Thus, it may be desirable to keep the balloon (1704) in a deflated configuration during advancement to the target tissue. When the balloon (1704) is inflated, it may form an aperture (1702) and may apply a closing force to a tissue at least partially within the aperture (1702). A tissue within the aperture (1702) may cause the balloon (1704) to deform and/or the material within the balloon (1704) to compress. The material within the balloon (1704) may be biased towards its original size and/or the balloon (1704) may be biased towards its original shape. Therefore, as the material within the balloon (1704) tries to expand and/or the balloon (1704) tries to return to its original shape, a closure force may be applied to the tissue within the aperture (1702) to keep the tissue closed. If the tissue within the balloon aperture (1702) shrinks (e.g., the area or volume of tissue within the aperture (1702) decreases), then the material within the balloon (1704) may expand and/or the balloon (1704) may move towards its original shape, which may decrease the size of the aperture (1702) until the tightening element (1700) is tightly around the tissue and a closure force is applied.

One or more wires and/or catheters may be used for positioning, inflation, and/or release of the balloon (1704). For example, as shown in FIGS. 17A and 17B, the closure device may comprise a first wire (1706), a catheter (1714) and a third wire (1716). These wires and/or catheters may be configured to serve different functions throughout the closure procedure. Specifically, the first wire (1706) may be configured to assist in positioning and/or shaping the balloon for closure, as will be explained in more detail below. The catheter (1714) may be coupled to the balloon (1704) and may serve as an inflation conduit to inflate the balloon during a closure procedure. The third wire (1716) may be releasably coupled to the balloon (1704) via a base (1710), and may be used to release the base, and the balloon (1704) coupled thereto, after the balloon (1704) is appropriately positioned and inflated to apply a continuous closure force to tissue. One or more of the wires and/or catheters may be at least partially housed in the elongate body (1710), and may be actuated with a control or controls in the handle. In some variations, catheters may be used in place of the first and second wires.

As shown in FIG. 17A, one end of the balloon (1704) may be connected to a first wire (1706) via a clip (1708), and the other end of the balloon (1704) may be connected to a base (1710). The first wire (1706) may be retracted proximally to stretch the balloon (1704) until the clip (1708) attaches to the base (1710), as shown in FIG. 17B. When both ends of the balloon (1704) are connected to the base (1710), the balloon (1704) may form an aperture (1702). The balloon (1704) may be stretched over or comprise a frame (1712) that may define a shape, such as a loop. In this way, the inflated balloon (1704) may form an aperture (1702) with a suitable shape to be positioned around a tissue.

In use, a closure device comprising the balloon (1704) may be advanced to a target tissue and the aperture (1702) of the balloon (1704) may be positioned around the tissue. In some variations, the balloon (1704) may first be stretched to form the aperture (1702), and then the target tissue may be positioned through the aperture (1702). In other variations, the balloon (1704) may be stretched around the target tissue, forming the aperture (1702) at the same time. The balloon (1704) may then be inflated with the catheter (1714). The balloon (1704) may be inflated until a specified volume of material (e.g., fluid, gas) is within the balloon (1704), or until the balloon (1704) reaches a desired pressure. After the balloon (1704) has been inflated around the tissue, the balloon (1704) and the base (1710) may be released from the closure device. Specifically, the first wire (1706) may be removed from the clip (1708), the catheter (1714) may be removed from a port, one-way valve, or the like in or coupled to the balloon (1704), and the third wire (1716) may be removed from the base (1710). Detachment of the catheter (1714), the first wire (1706), and a second wire (1716)

may release the balloon (1704) and the base (1710) such that only the elements shown in FIG. 17C are implanted and remain within the body.

FIGS. 18A-18C depict another variation of a tightening element (1800) comprising an aperture (1802). This tightening element (1800) comprises a force generator (1801) that may be moveable between a closed configuration, shown in FIG. 18A, and an open configuration, shown in FIGS. 18B and 18C. The change in the shape of the force generator (1801) between these two configurations may result in a change in the diameter (of major and/or minor axes) and the area of the aperture (1802), while the perimeter or circumference of the aperture (1802) may or may not change. While the aperture (1802) is depicted as circular or ellipsoidal, it should be appreciated that the aperture (1802) may comprise any shape suitable to close a target tissue (1804).

The force generator (1801) may comprise one or more elastic materials, such that the force generator (1801) may be biased towards the closed configuration. In the closed configuration, the area of the aperture (1802) may be minimized. Thus, moving the force generator (1801) from a closed to an open configuration may increase the size of the aperture (1802), which may allow a tissue (1804) to be at least partially positioned through the aperture (1802). As the force generator (1801) tries to return to its original shape, the size of the aperture (1802) may decrease until the force generator (1801) is tightly around the tissue (1804). At that point, the size of the aperture (1802) may be prevented from decreasing further, and a continuous closure force may be applied to the tissue (1804). If the area of the tissue (1804) within the aperture (1802) shrinks over time, the force generator (1801) may move toward its closed configuration, and the aperture (1802) size may decrease until the force generator (1801) is once again tightly around the tissue (1804).

In order to move the force generator (1801) from a closed configuration to an open configuration, the tightening element (1800) may comprise an actuating mechanism. The variation of actuating mechanism shown in FIGS. 18A-18C may comprise a cord (1806) (e.g., suture, wire, thread) that may be attached to a distal portion of the force generator (1801). Proximally retracting the cord (1806) may move the force generator (1801) from the closed configuration to the open configuration. Releasing the cord (1806) may allow the force generator (1801) to move towards its original shape. The tightening element (1800) may be released from a closure device in any suitable manner, and in variations comprising a cord (1806), the cord (1806) may be severed to facilitate the release of the tightening element (1800). FIG. 18C shows the tightening element (1800) as it may appear after release from the closure device.

FIGS. 28A-28F provide another example of a tightening element (2801) comprising an aperture (2824). FIGS. 28A-28D depict a distal portion of a closure device (2800) comprising a tightening element (2801), an elongate body (2804) comprising a lumen (2806) therethrough, and a pusher (2809) slideably disposed within the lumen (2806). The tightening element (2801), which may comprise a force generator (2802) and a lock (2810), may be at least partially disposed within the lumen (2806) and may extend from a distal end thereof. The force generator (2802) may comprise a loop (2812) and ends (2814), and the loop (2812) may at least partially define an aperture (2824). When a tensile force is applied to the force generator (2802), the force generator (2802) may stretch and its cross-sectional diameter may decrease. For example, in some variations, the force generating (2802) may comprise a vessel loop or other elastic band. The force generator (2802) may have any suitable cross-sectional shape, for example, elliptical, circular, square, rectangular, or the like. In some embodiments, the force generator (2802) may be radiopaque.

The lock (2810) may comprise a lumen (2816) therethrough, through which a portion of the force generator (2802) may be disposed. Generally, the lock may be configured to prevent the size of the loop (2812) from changing when the tightening element (2801) is in the open configuration (as described in more detail below). For example, the lumen (2816) of the lock (2810) may comprise a narrow region that prevents the force generator (2802) from moving through the lumen (2816) when the tightening element (2801) is in the open configuration. In the embodiment depicted in FIGS. 28A-28F, the lumen (2816) of the lock (2810) may comprise a proximal cylindrical portion (2818) and a distal conical portion (2820), which may form a narrow region with a ledge (2822) (See FIG. 28F). When the tightening element (2801) is in the open configuration, the cross-sectional diameter of the ends (2814) of the force generator (2802) may cause the ends (2814) to abut against the ledge (2822). This may prevent the lock (2810) from moving proximally along the force generator (2802) and may prevent the loop (2812) from increasing in size. Additionally, the narrow portion of the lumen (2816) may also prevent the lock (2810) from moving distally along the force generator (2802) when the tightening element (2801) is in the open configuration.

While depicted in FIGS. 28A-28F as comprising cylindrical and conical portions (2818, 2820), the lumen (2816) of the lock (2810) may comprise any configuration that results in a narrowed portion of the lumen (2816). For example, in other variations, for example those depicted in FIGS. 29A-29C, the lock (2910A, 2910B, 2910C) may comprise a cylinder that is crimped (FIG. 29A), flattened (FIG. 29B), or comprises depressible tabs (FIG. 29C) to create a narrow portion of the lumen. In some instances, it may be desirable to utilize the locks depicted in FIGS. 29A-29C because they may be easier to load onto or otherwise couple to the force generator. For example, the locks depicted in FIGS. 29A-29C may be coupled to the force generator before forming the narrow portion of the lumen, which may allow the locks (2910A, 2910B, 2910C) to be coupled to the force generator when it is not under tension.

Figure 28C:
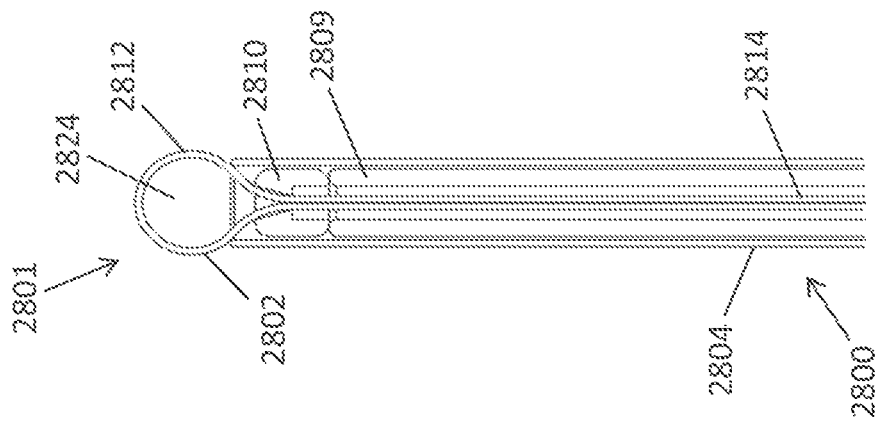
Figure 28B:
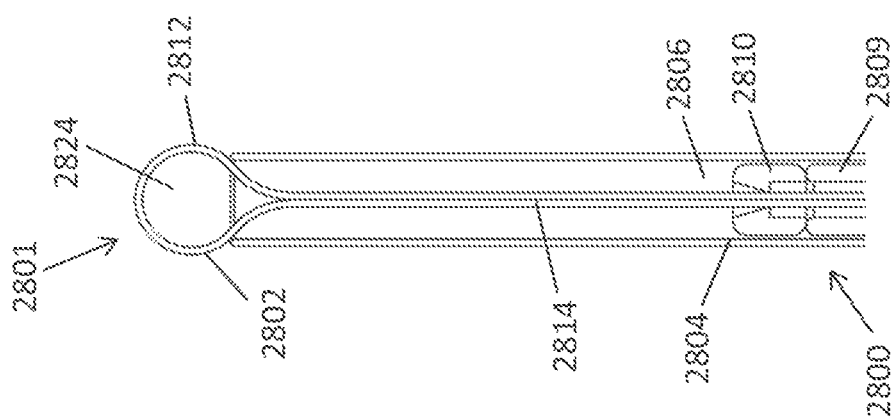
Figure 28A:
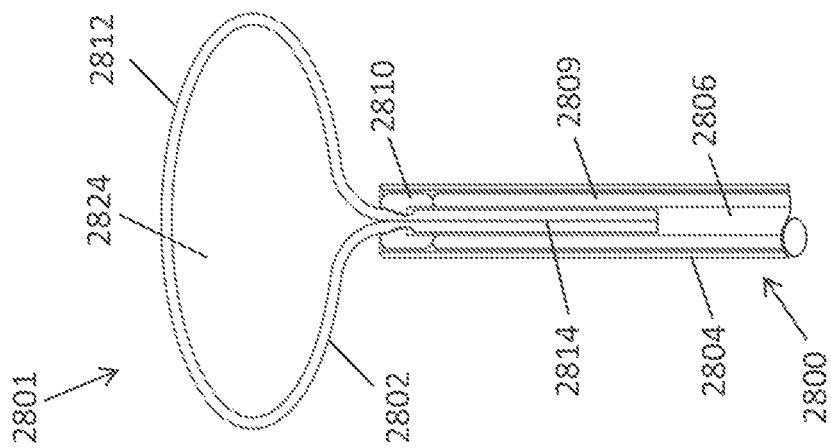
Figure 29B:
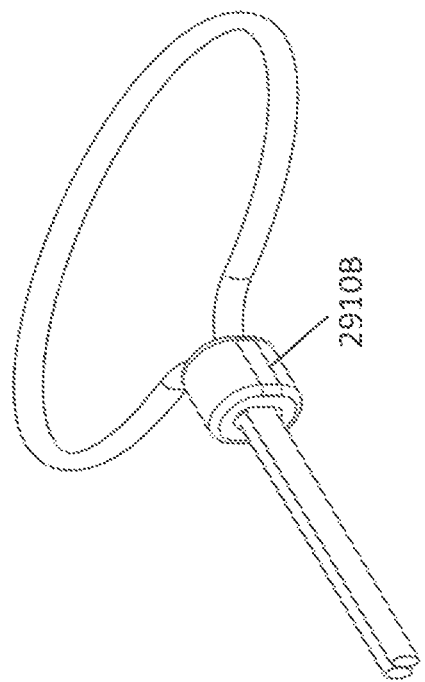
FIGS. 29A-29C illustrate variations of a lock that may be used with the tightening element described with respect to FIGS. 28A-28F.
Figure 29A:
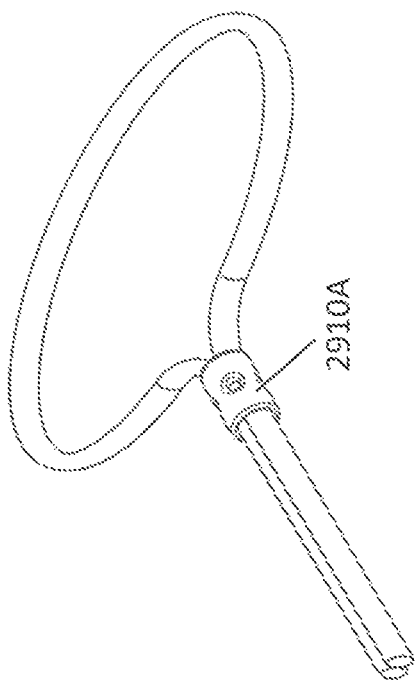
Figure 29C:
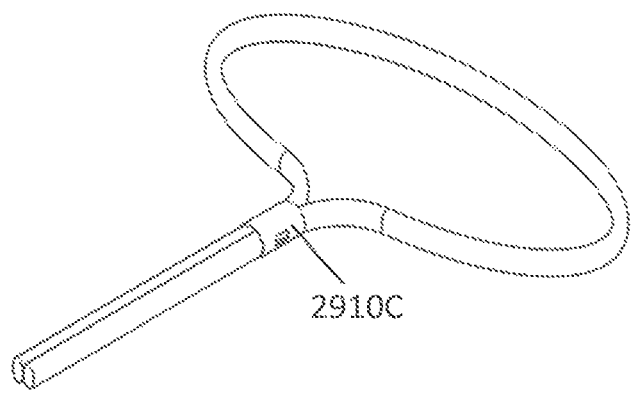

The tightening element (2801) may be moveable between an open configuration, shown in FIG. 28A, and two closed configurations, a tensioned-closed configuration, shown in FIGS. 28B-28C, and a relaxed-closed configuration, shown in FIGS. 28D-28F. Moving the tightening element (2801) from the open configuration to the closed configurations may decrease the size of the aperture (2824) (e.g., diameter, area, circumference), and apply a force radially inward to close the tissue. The tightening element (2801) may be in the open configuration when the loop (2812) is configured to encircle a target tissue and both the loop (2812) and the ends (2814) of the force generator (2802) are relaxed (i.e., not tensioned). The tightening element (2801) may be in the tensioned-closed configuration when the loop (2812) is closed around the tissue (e.g., exerting a closure force) and both the loop (2812) and the ends (2814) of the force generator (2802) are under tension. The tightening element (2801) may be in the relaxed-closed configuration when the loop (2812) is closed around the tissue and remains tensioned, while the ends (2814) are relaxed. The tightening element (2801) may be moved from the tensioned-closed configuration to the relaxed-closed configuration by moving the lock (2810) distally to a desired closure location and releasing or otherwise removing the force applied to the force generator (2802). Locking the loop (2812) of the force generator (2802) while it is under tension may result in the force generator (2802) applying a closure force to the tissue, regardless of whether the amount of tissue within the loop (2812) decreases.

As mentioned above, FIGS. 28A-28F show the tightening element (2801) as it is transitioned from the open configuration, through the tensioned-closed configuration, to the relaxed-closed configuration. FIG. 28A depicts the distal end of the closure device (2800) once the force generator (2802) has been advanced to and encircles a target tissue (tissue not shown). The loop (2812) of the force generator (2802) may extend from the distal end of the elongate body (2804), while the ends (2814) of the force generator (2802) may remain in the lumen (2806) of the elongate body (2804). The lock (2810) may be positioned at the distal end of the lumen (2806) of the elongate body (2804) and the pusher (2809) may be positioned adjacent to and proximal of the lock (2810). The pusher (2809) may comprise a lumen through which the ends (2814) of the force generator (2802) may be disposed. The loop (2812) may be positioned and configured to be advanced around the target tissue (e.g., the diameter of the loop may be large enough to encircle the target tissue).

After the loop (2812) is placed around the target tissue, a tensile force may be applied to the force generator (2802) (e.g., by pulling the ends (2814) of the force generator (2802)), moving the force generator (2802) into the tensioned-closed configuration depicted in FIGS. 28B and 28C. Applying a tensile force to the force generator (2802) while holding the elongate body (2804) stationary may serve two purposes. First, applying a tensile force to the force generator (2802) may decrease the size (e.g., diameter, area, circumference) of the loop (2812) and aperture (2824) and tighten the loop (2812) around the target tissue. Second, applying a tensile force to the force generator (2802) may reduce its cross-sectional diameter, which may allow the lock (2810) to be moved along the force generator (2802) within the elongate body (2804). More specifically, the decrease in cross-sectional diameter of the force generator (2802) may allow the force generator (2802) to fit through both the conical and cylindrical portions (2820, 2818) of the lumen (2816) in the lock (2010) without catching on the ledge (2822) or otherwise becoming pinched. Thus, the decrease in cross-sectional diameter of the force generator (2802) may allow the lock (2810) to advance and/or retract (e.g., slide) along the force generator (2802). In some variations, the lock (2810) and the pusher (2809) may be retracted by a user (e.g., through a slider or other actuator, for example, on the handle) simultaneously with the application of the tensile force to the force generator (2802) (e.g., at the ends (2814)). In other variations, the lock (2810) and the pusher (2809) may move proximally due to the thinning or reduction in cross-sectional diameter of the force generator (2802) (e.g., the lock (2810) and pusher (2809) may slide proximally along the force generator (2802) on their own). In still other variations, the lock (2810) and pusher (2809) may remain at the distal end of the elongate body (2804) while the tensile force is applied to the ends (2814) of the force generator (2802).

After the loop (2812) is closed around the target tissue and the loop (2812) and at least a portion of the ends (2814) of the force generator (2802) are stretched, the pusher (2809) may be moved distally relative to the elongate body (2804) to move the lock (2810) toward the loop (2812), as can be seen in FIG. 28C. The elongate body (2804) may remain stationary while the lock (2810) is advanced, which may hold the force generator (2802) in the proper location.

After the lock has been positioned, the force applied to the force generator (2802) may be released. Releasing the applied force may transition the tightening element (2801) into the relaxed-closed configuration, as depicted in FIG. 28D. In this configuration, the loop (2812) of the force generator (2802) may remain under tension, while the ends (2814) may be relaxed. This may result in the cross-sectional diameter of the loop (2812) of the force generator (2802) remaining reduced, while the cross-sectional diameter of the ends (2814) returns (expands) to its pre-tensioned value. Thus, in the relaxed-closed configuration, the cross-sectional diameter of the loop (2812) of the force generator (2802) may be less than the cross-sectional diameter of the ends (2814). The loop (2812) may remain locked in tension because the relaxed ends (2814) of the force generator (2802) may again catch on the ledge (2822) inside of the lock (2810). This may prevent the lock (2810) from sliding or otherwise moving proximally, which may allow the loop (2812) to enlarge. The elongate body (2804) with the pusher (2809) disposed therein may be removed and the force generator (2802) may be severed or released from the closure device (2800), leaving only the force generator (2802) and the lock (2810) at the target tissue (FIG. 28E).

As mentioned above, the loop (2812) may apply a continuous closure force to the tissue. If the target tissue within the loop (2812) thins, remodels, or otherwise decreases, the tension in the loop (2812) may cause the loop (2812) to contract and decrease in size (e.g., diameter, area) such that a continuous closure force is maintained on the tissue. Additionally, as depicted in FIG. 28F, if the amount or size of tissue within the loop (2812) decreases, the cross-sectional diameter of the loop (2812) of the force generator (2802) may expand toward its relaxed value, which may supplement the closure force provided by the tension.

The closure device (2800) depicted in FIGS. 28A-28D may be a variation of the closure device (200) described with respect to FIGS. 2A-2B in which the tightening element (2801) comprising an aperture (2824) described with respect to FIGS. 28A-28F may be used instead of the tightening element (208) and suture (210) described with respect to FIGS. 2A-2B. For example, the closure device (2800) may comprise a retention member (220) that may releasably couple the force generator (2802) to the snare (206) prior to deploying the tightening element (2801). In other variations, the force generator (2802) may additionally comprise shape-memory properties such that it may be utilized without a snare.

Tightening elements that comprise an aperture may be at least partially housed in the elongate body prior to release. For example, these tightening elements may be at least partially housed in a lumen, recess, or compartment of the elongate body. In some variations, the tightening element may be in a closed or expanded configuration while it is at least partially housed in the elongate body. In these variations, the size or shape of the tightening element may be changed prior to its positioning around a tissue. In other variations, the tightening element may be held in the compressed or open configuration while it is at least partially housed in the elongate body, and the tightening element may move towards its original size and/or shape after release from the elongate body. In some variations, one or more portions of the tightening element may be coupled to the snare loop, such that changes in the size of the snare loop may change the size, shape, and/or orientation of the tightening element. The tightening element may be released from the closure device in any suitable manner. For example, the tightening element may be tethered to the closure device and the tether may be severed in order to release the tightening element. In other variations, the tightening element may be pushed, dislodged, or otherwise detached to release it from the closure device. It should be appreciated that in some variations, the tightening element may be delivered to a target tissue by a device other than the closure device, such as a catheter.

Figure 23A:
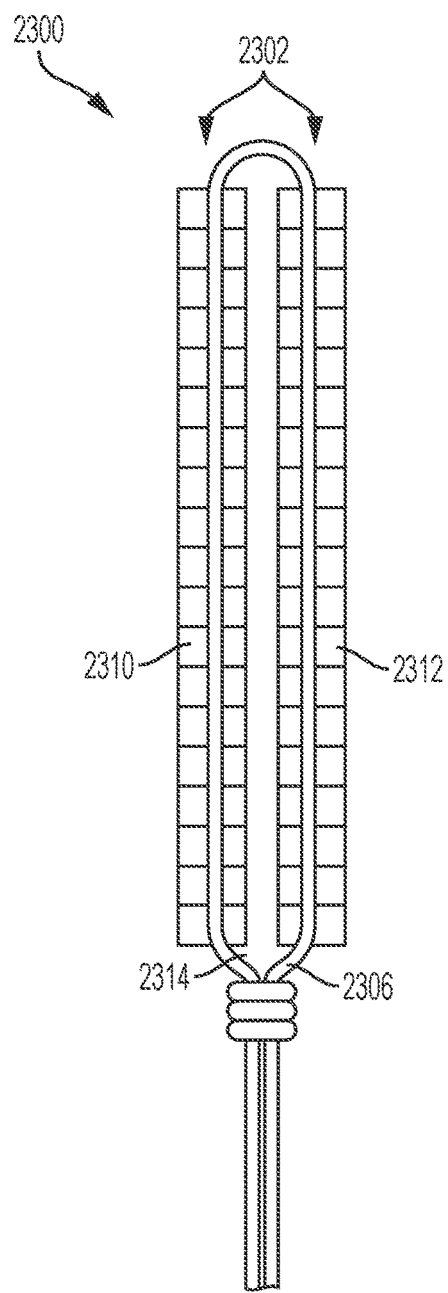
FIGS. 23A and 23B show a variation of a tightening element and suture loop arrangement described here comprising an aperture in a first configuration and a second configuration, respectively.
Figure 23B:
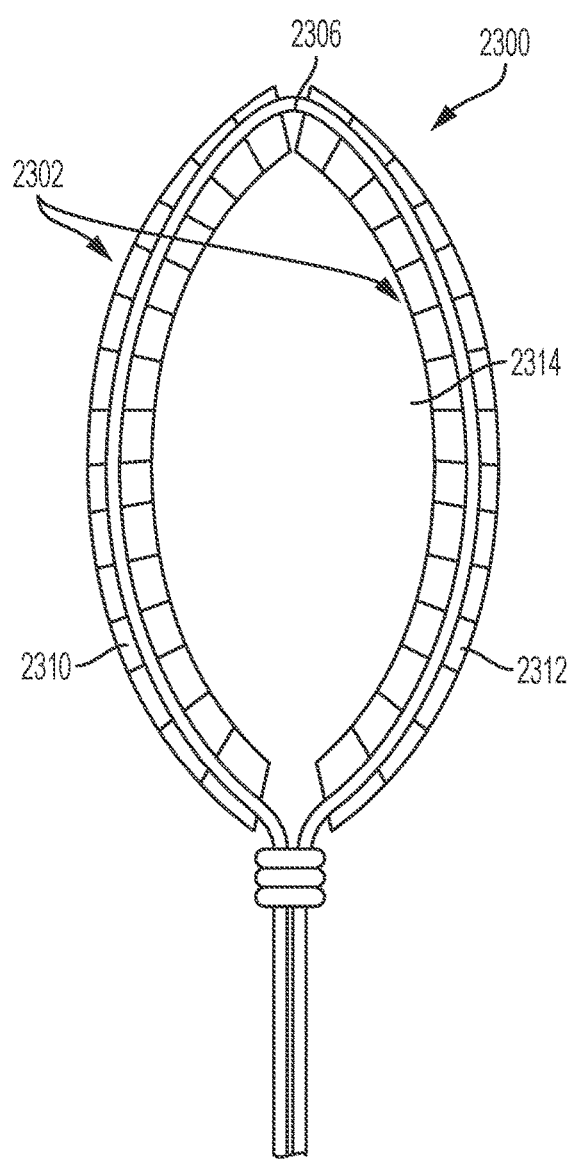

While two types of tightening elements have been described, those that couple to a suture or snare to form a tightening element and suture loop or snare loop arrangement and those that comprise an aperture, some variations of tightening elements may comprise features of both types. For example, FIGS. 23A and 23B show a tightening element and suture loop arrangement (2300) comprising an aperture (2314). The aperture (2314) may be partially formed by a tightening element (2302) and partially formed by a suture loop (2306). The tightening element (2302) may comprise two force generators (2310, 2312), which may each be coils (e.g., spring coils) or flexible tubes, a combination thereof, or the like. FIG. 23A shows the tightening element (2302) in a first configuration with the force generators (2310, 2312) straight, and FIG. 23B shows the tightening element (2302) in a second configuration with the force generators (2310, 2312) curved. The tightening element (2302) may exhibit elasticity such that it is biased towards the first configuration.

The suture loop (2306) may extend through one or more lumens of the tightening element (2302) such that a change in the shape of the tightening element (2302) may result in a change in the shape of the suture loop (2306). As the tightening element (2302) and the suture loop (2306) change shape, the area within the aperture (2314) may change. For example, the area within the aperture (2314) may be less when the tightening element (2302) is in the first configuration than when the tightening element (2302) is in the second configuration. In use, a tissue may be positioned within the aperture (2314) of the tightening element and suture loop arrangement (2300), and a closure force may be exerted on the tissue while the tightening element (2302) is in the second configuration. If the tissue within the aperture (2314) shrinks over time, the tightening element (2302) may move towards the first configuration, decreasing the size of the aperture (2314) until the suture loop (2306) and the tightening element (2302) are tightly around the tissue.

Additionally, while the tightening element (2801) described above with respect to FIGS. 28A-28F has been characterized as a tightening element with an aperture, it should be appreciated that it, or the force generator (2802) alone, may also be used as part of any of the tightening element and suture loop arrangements described herein. For example, the tightening element (2801) may be used in any of the embodiments described with respect to FIGS. 4, 5A-5C, 6, 7, 8A-8B, 9A-9B, 11, 12A-12C, 13, 14, 15, 16A-16B. Additionally, for example, the force generator (2802) alone may be used instead of the suture described with respect to FIGS. 4, 5A-5C, 6, 7, 8A-8B, 9A-9B, 11, 12A-12C, 13, 14, 15, 16A-16B.

Elongate Body

The elongate body of the closure devices described herein may connect the snare loop, the tightening element, and/or the suture loop at the distal end of the elongate body with the handle and/or one or more actuating mechanisms at the proximal end of the elongate body. In some variations the elongate body may be straight, and in other variations the elongate body may comprise one or more curves. In some variations, at least a portion of the elongate body may be flexible. In these variations, the closure device may comprise one or more mechanisms that may act to change the shape of the elongate body. In instances where the elongate body comprises one or more curves, a tube, mandrel, or other straightening mechanism may be used to temporarily straighten the elongate body. For example, a rigid tube or mandrel may be placed in one or more lumens of the elongate body, which may temporarily straighten any curved sections. In other variations, one or more pre-curved tubes or mandrels may be inserted into elongate body to create one or more curved sections. In still other variations, one or more pull wires may be disposed in, on, or around the elongate body and may cause the elongate body to flex or bend when one or more of the pull wires is pulled, pushed or otherwise manipulated.

The elongate body may comprise a tip portion at the distal end thereof. For example, FIG. 2B illustrates a distal portion of an elongate body (202) that comprises a tip (218). In some variations, the tip of the elongate body may be formed separately from the elongate body, and may be attached to the body during assembly of the device. In other variations the tip portion may be integrally formed with the elongate body. The tip portion may serve a number of useful functions. In some instances, the tip may be configured to be atraumatic, which may act to reduce the risk of damaging tissue as the distal end of the elongate body is moved within the body. In other instances, the tip may allow certain portions of the snare, tightening element, and/or suture to move through the elongate body while holding other portions in place.

The various components of the snare, tightening element, and/or suture may be at least partially housed within any lumen, sub-lumen, recess, or other compartment of the elongate body. The elongate bodies described herein may have any suitable number of lumens. It should be appreciated that when the term "lumen" is used herein, it may be used to describe any bore or passageway extending through a length of the elongate body or other portion of the closure device. It should be appreciated that a lumen need not be entirely enclosed (i.e., the lumen may comprise one or more slots, slits, gaps or other openings along some or all of the length of the lumen). The elongate body may comprise one, two, three, four, or five or more lumens. Some or all of the lumens may extend entirely through the elongate body (i.e., from the proximal end of the elongate body to the distal end of the elongate body). Other lumens may pass through only a portion of the elongate body (e.g., from one end to an intermediate point along the elongate body, between two intermediate points along the elongate body). In variations of elongate bodies comprising a tip, the elongate body and the tip may have the same number or a different number of lumens.

Figure 19A:
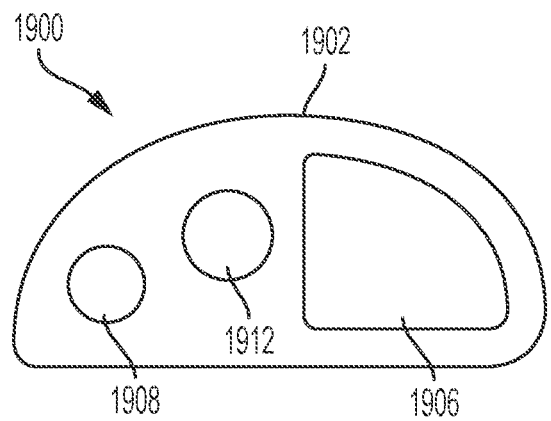
FIGS. 19A and 19B are front and cross-sectional views, respectively, of a distal portion of a variation of an elongate body described here.
Figure 19B:
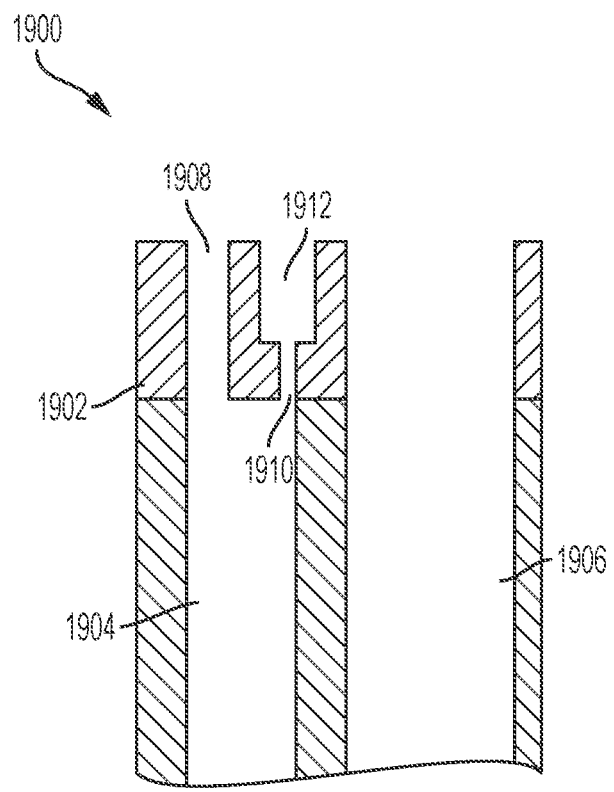

In some instances, one or more of the lumens of the elongate body may be at least partially divided into one or more sub-lumens. Specifically, a lumen may be split into two or more sub-lumens along a portion of the length of the lumen. The distal portion of an elongate body may also comprise one or more recesses. For example, FIGS. 19A and 19B show a front view and a cross-sectional view, respectively, of a distal portion of an elongate body (1900) comprising a tip (1902). In this variation, the elongate body (1900) may comprise a first lumen (1904) and a second lumen (1906). The first lumen (1904) may be divided into first and second sub-lumens (1908, 1910) at the tip (1902).

The second sub-lumen (1910) may connect the first lumen (1904) to a distal recess (1912).

Various components of the snare, tightening element, and/or suture may be at least partially housed in these compartments. For example, a fixed end of the snare may extend through the first sub-lumen (1908) and the first lumen (1904), while a free end of the suture may pass to the handle through the second sub-lumen (1910) and the first lumen (1904). At least a portion of the tightening element and/or the suture knot may be housed in the recess (1912). This may allow a free end of the suture to be pulled through the second sub-lumen (1910) while the suture knot and/or the tightening element are held stationary in the recess.

The various structures of the elongate body and the configurations of elements at least partially housed in the elongate body are described in more detail in U.S. Pat. No. 9,198,664, entitled "Tissue Ligation Devices and Controls Therefor" and filed on Apr. 1, 2010, which was previously incorporated by reference in its entirety.

Handle

The closure devices described herein may comprise a handle coupled to the proximal end of the elongate body. The handle may be configured to be held by a user in order to maneuver the closure device. The handle may also comprise one or more mechanisms for controlling elements at the distal end of the elongate body. For example, the handle may comprise a mechanism or mechanisms for opening and/or closing the snare loop, actuating the tightening element, locking the suture loop and in some variations, the snare loop, releasing the tightening element, and/or tightening the suture loop. FIG. 2A depicts an exemplary handle (204). In this variation, the handle (204) may comprise a linear actuation slide (212) for controlling the snare and a fob (214) for actuating the tightening element and/or the suture. The slide (212) may be pushed and pulled to advance and retract a free end of the snare within the elongate body (202), thus changing the size of the snare loop. The fob (214) may be pulled away from the handle (204) to tighten the suture loop and/or change the size and/or shape of the tightening element. In some variations, the fob (214) may be detached from the suture, such as by severing the suture, which may allow the suture to be pulled through and/or released from the closure device (200). Also seen is a port (216), through which one or more instruments (e.g., a guidewire, a catheter) may be advanced. It should be appreciated that the handle may comprise any suitable number of slides, levers, buttons, knobs, slots, or the like to control one or more elements of the closure device.

Figure 20B:
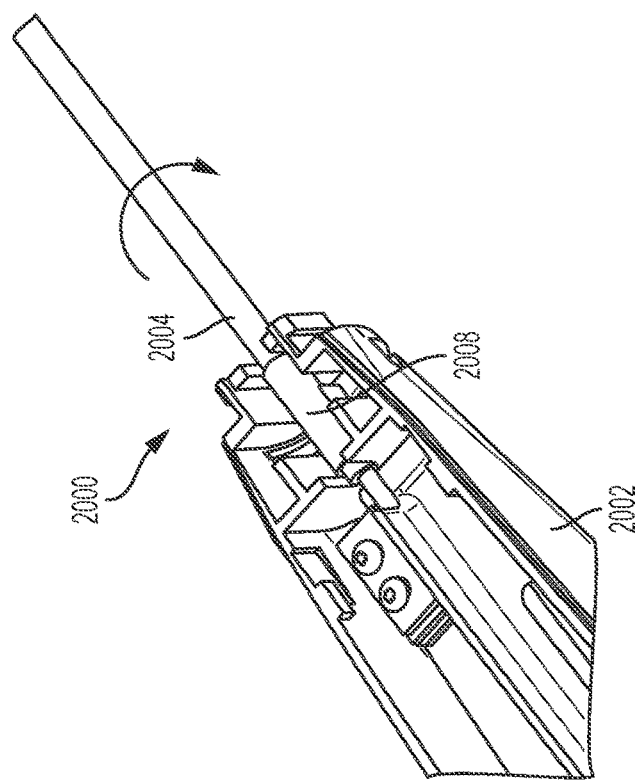
FIGS. 20A-20D show a proximal portion of a variation of a closure device described here comprising an actuating mechanism configured to rotate the snare loop.
Figure 20A:
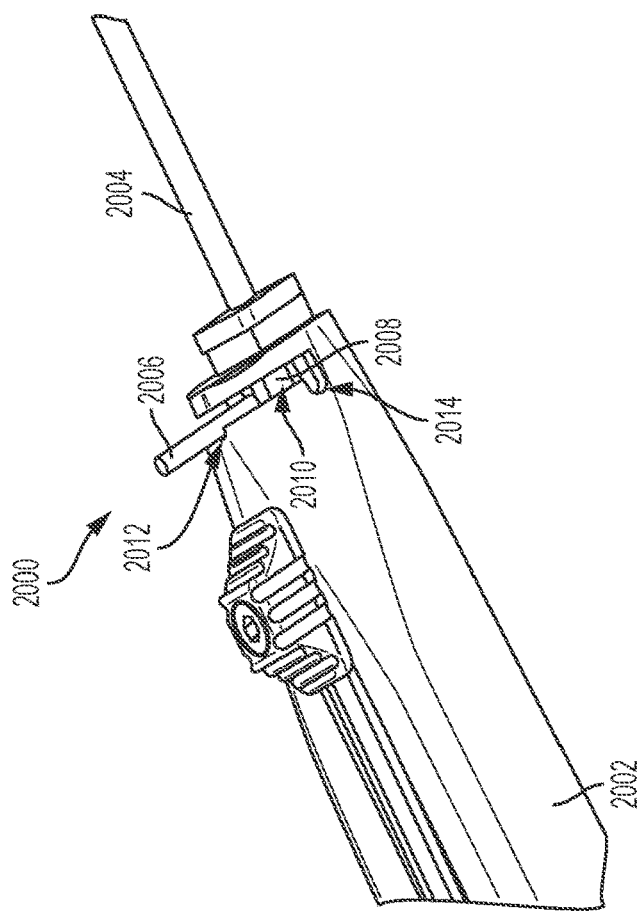

In some embodiments, the snare loop may be rotated relative to a longitudinal axis of the elongate body. This may facilitate proper positioning of the snare loop around a target tissue. FIGS. 20A-20D show a proximal portion of a closure device (2000) comprising an actuating mechanism (2006) configured to rotate the snare loop (not shown) positioned at the distal end of the elongate body (2004). The actuating mechanism (2006) may comprise a lever, and it may be rotated to rotate the snare loop. In the bottom view shown in FIG. 20B, a portion of the handle (2002) has been removed to illustrate how this mechanism may be configured. As shown there, the actuating mechanism (2006) may be coupled to a collar (2008), which may in turn be coupled to the elongate body (2004). Thus, in this embodiment, rotation of the collar (2008) may rotate the elongate body (2004), which may rotate the snare loop coupled thereto. As seen in FIG. 20A, the actuating mechanism (2006) may extend from the collar (2008) through a slot (2010) in the handle (2002) so that a user may manipulate the actuating mechanism (2006).

Figure 20C:
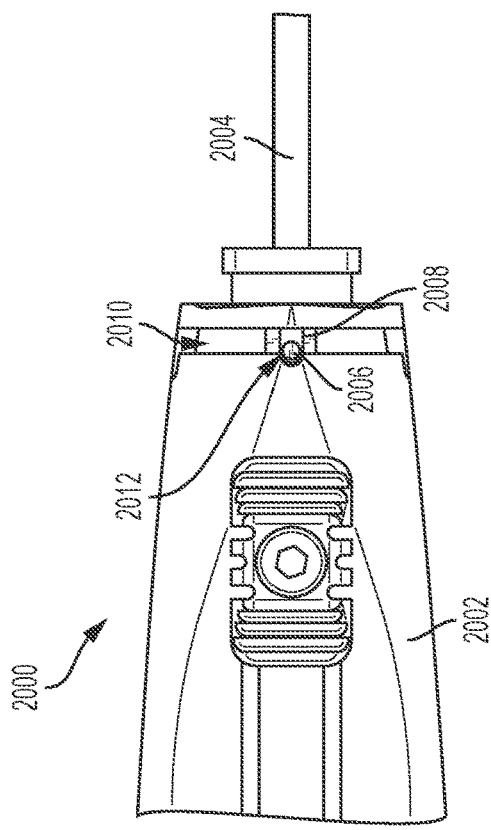
Figure 20D:
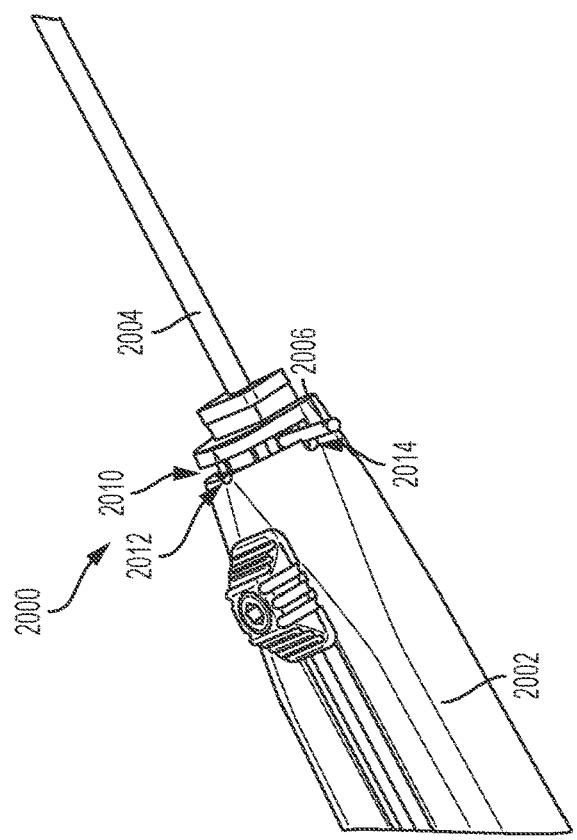

The slot (2010) may comprise one or more detents (e.g., catches, locks, indentations) (2012, 2014) that may temporarily restrain or retain the actuating mechanism (2006). When the actuating mechanism (2006) is at a detent (2012, 2014), the actuating mechanism (2006) and the snare loop may be retained in specific rotational positions. In this way, a user may know the position of the snare loop by observing the position of the actuating mechanism (2006) relative to the detent (2012, 2014). For example, when the actuating mechanism (2006) is at the first detent (2012), as seen in FIGS. 20A and 20C, the plane of the snare loop opening may be parallel to the top of the handle (2002). When the actuating mechanism (2006) is at the second detent (2014), as seen in FIG. 20D, the plane of the snare loop opening may be perpendicular to the top of the handle (2002). The detents (2012, 2014) may also help hold the snare loop in a desired rotational configuration. For example, a greater force may be required to move the actuating mechanism (2006) when it is at a detent (2012, 2014) than when it is between detents, and therefore, the detents (2012, 2014) may help to hold the snare loop in a specified position.

The slot (2010) may traverse any suitable amount of the handle (2002) and may be placed in any suitable location on the handle (2002). For example, the slot (2002) may traverse a portion of the circumference of the handle (2002) such that the slot (2010) may enable the actuating mechanism (2006), and therefore the snare loop, to rotate a desired amount (e.g., any amount between 0 and 360 degrees). In some embodiments, the slot (2010) may enable the actuating mechanism (2006), and thus the snare loop, to rotate at least about 15 degrees, 30 degrees, 50 degrees, 80 degrees, 90 degrees, 120 degrees, 140 degrees, 160 degrees, or 180 degrees. In some embodiments, as depicted in FIGS. 20A-20D, the perimeter of the slot (2010) may prevent the actuating mechanism (2006) from rotating more than 180 degrees, which may in turn limit the rotation of the elongate body (2004) and snare loop to 180 degrees. While the perimeter of the slot (2010) may limit the rotation of the actuating mechanism (2006) and the snare loop, rotation may be restricted in any suitable manner. For example, there may be stops or protrusions on the collar (2008), elongate body (2004), or snare loop that may contact another portion of the closure device (2000) to limit rotation of the snare loop.

In variations of closure devices where the snare loop is temporarily coupled to a suture loop, the snare loop and the suture loop may be configured to rotate together. In other variations comprising a suture loop, the snare loop may rotate independently of the suture loop. In some variations of closure devices, the elongate body and the snare loop may be configured to rotate together, and in other variations, the snare loop may be configured to rotate independently of the elongate body. In some of these variations, both the snare loop and the elongate body may rotate independently. In variations in which the snare loop may be rotated independently of the elongate body, the snare loop may be rotated in any suitable manner. For example, a portion of the snare (e.g., one or more ends of the snare housed in the elongate body or handle, the snare loop) may be coupled to an actuating mechanism. In some of these embodiments, an actuating mechanism may extend through slots in both the handle and in the elongate body to connect to a collar or other rotatable structure at least partially housed in the elongate body. The collar within the elongate body may in turn be attached to a portion of the snare. In other variations, an actuating mechanism may rotate the distal tip of the elongate body, which may also rotate the snare loop. For example, a rigid structure may extend from the distal tip and/or the snare loop, through a lumen of the elongate body, and to the handle, where it may be attached to a rotating actuating mechanism (e.g., lever, knob).

Figure 21:
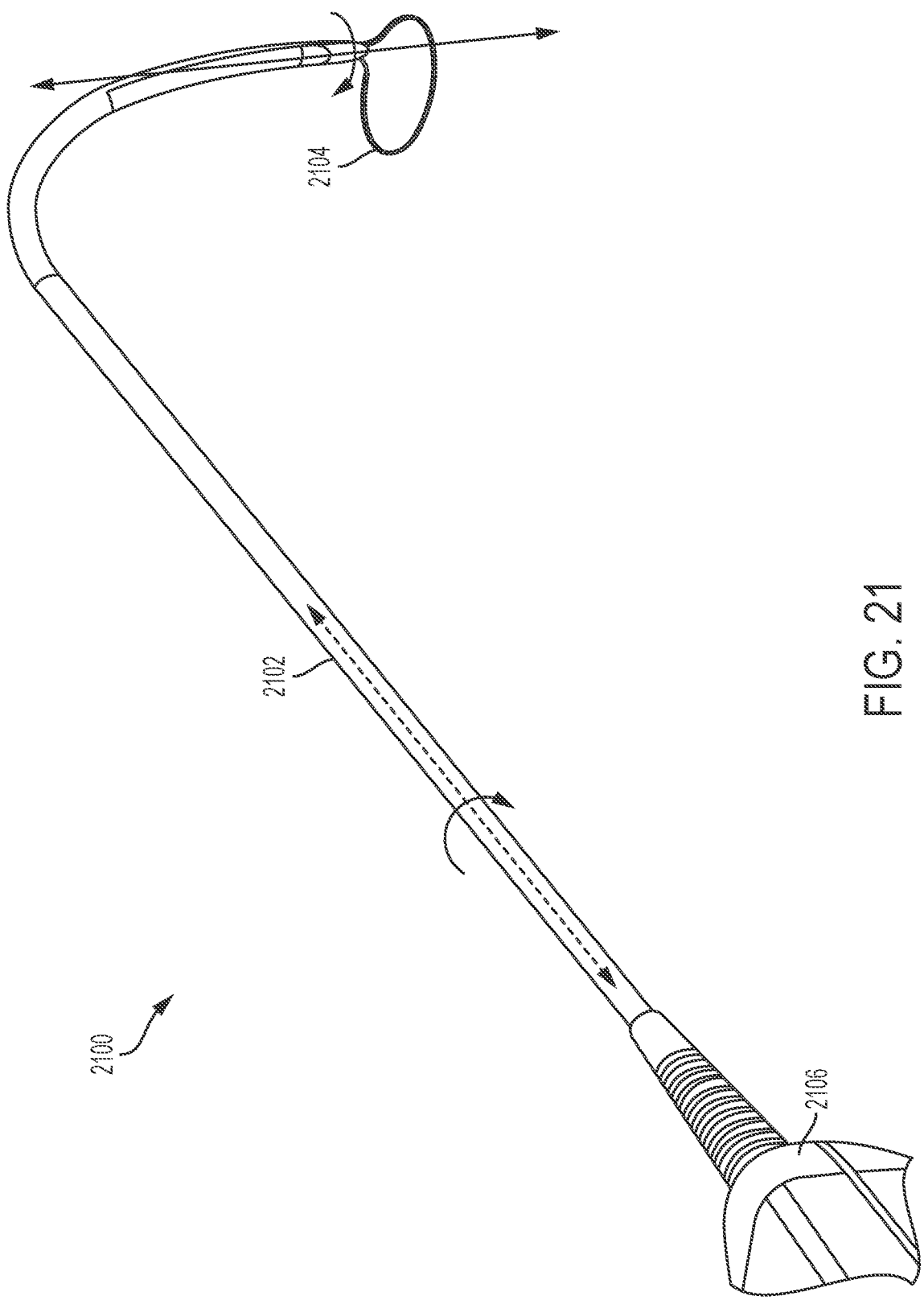
FIG. 21 shows a distal portion of a variation a closure device described here illustrating rotation of the snare loop.

The closure devices may be configured such that the snare loop rotates relative to a longitudinal axis of the elongate body. This longitudinal axis may be defined differently in variations in which the suture loop and the elongate body rotate together, as opposed to variations in which the suture loop rotates independently of the elongate body. The closure device (2100) shown in FIG. 21 illustrates this concept. When the elongate body (2102) and the snare loop (2104) rotate together, they may rotate relative to the longitudinal axis of the elongate body (2102) portion that is closest to the handle (2106). More specifically, if the actuating mechanism is configured as shown in FIGS. 20A-20D, rotation may be relative to the longitudinal axis of the collar (2008), and therefore the longitudinal axis of the elongate body (2004) portion directly attached to the collar (2008). This first longitudinal axis is illustrated by the dashed double arrow in FIG. 21. In contrast, when the snare loop (2104) is configured to rotate without rotation of the elongate body (2102), it may rotate relative to the longitudinal axis of the elongate body (2102) portion that is closest to the snare loop (2104) (e.g., the distal end or tip of the elongate body). This second longitudinal axis is illustrated by the solid double arrow. If the elongate body (2102) is straight, these longitudinal axes may be the same. However, if the elongate body (2102) comprises one or more curves, these longitudinal axes may be different, as shown in FIG. 21.

Methods

Methods for closing the left atrial appendage are described here. However, it should be appreciated that the devices described herein may be used to close or ligate any suitable tissue. For example, a tissue closure device may be used to ligate a blood vessel (e.g., to provide hemostasis, to treat hemorrhoids), a portion of the gastrointestinal tract (e.g., the appendix), a portion of the hepatobiliary system (e.g., the cystic duct), or a portion of the reproductive system (e.g., a fallopian tube). It should be appreciated that any of the devices described herein may be used in conjunction with one or more of the methods described here or the methods and/or devices described in U.S. Pat. No. 8,771,297, entitled "Devices, Systems, and Methods for Closing the Left Atrial Appendage" and filed on Mar. 25, 2008, and U.S. Pat. No. 9,198,664, entitled "Tissue Ligation Devices and Controls Therefor" and filed on Apr. 1, 2010, which were previously incorporated by reference in their entirety.

The methods described here comprise accessing the left atrial appendage. Once access has been achieved, a closure device, such as those described herein, may be advanced to the left atrial appendage. In some variations, the closure devices may be advanced and positioned with the help of one or more guide devices and/or one or more stabilizing/positioning devices (e.g., an expandable member or the like). The closure device may be used to ensnare and close the left atrial appendage. A tightening element, with or without an attached suture loop or snare loop, may be released from the closure device to hold the left atrial appendage closed by producing a continuous closure force. The closure device may then be withdrawn from the body, and the tightening element may remain at the left atrial appendage. These steps will be described in more detail herein.

As mentioned, the methods described herein may comprise gaining access to the left atrial appendage. In some variations, the left atrial appendage may be accessed from both inside of the heart and outside of the heart. To access the inside of the heart, the vasculature is typically used. In some variations, the heart is accessed on the inside via the common femoral vein (e.g., the right common femoral vein) using a standard Seldinger technique with a needle. Access to the left atrium may be then be obtained using standard transseptal access techniques. For access to the heart from the outside, a subthoracic access point may be used. The access point may be any suitable location (e.g., intercostal via a sternotomy, thoracostomy, or thoracotomy; right of the xiphoid process and pointed towards the patient's left shoulder via a minimally invasive or percutaneous approach; or in the costal cartilage or xiphoid process itself).

In some variations, the left atrial appendage may be closed using the devices described here without performing both access procedures as described above. For example, in some variations, the methods may comprise advancing a first guide having a proximal end and a distal end into the left atrial appendage, through the left atrial appendage, and out of the left atrial appendage, such that one of the proximal or distal ends is within the vasculature, and one of the proximal or distal ends is within the subthoracic space.

By virtue of gaining access to the left atrial appendage, one or more guides having alignment members may be advanced to the left atrial appendage. These guides may be any suitable guide, such as those described in U.S. Pat. No. 8,771,297, entitled "Devices, Systems, and Methods for Closing the Left Atrial Appendage" and filed on Mar. 25, 2008, which was previously incorporated by reference in its entirety. For example, first and second guides having alignment members may be used to guide the procedure. The alignment members may be any suitable alignment members (e.g., interconnecting elements, one or more vacuum members, radiopaque or echogenic markers, members that are configured to produce an audible response, magnets, and the like). In some variations, the alignment members may be magnets located at the distal ends of the guides. These guides may be used for guiding additional tools and/or devices (e.g., the closure device) to the left atrial appendage.

For example, in some variations, a first guide may be advanced into the left atrial appendage, while the second guide may be advanced into the pericardial space adjacent to the left atrial appendage. Either of these guides may be advanced under any of a variety of visualization techniques, such as fluoroscopic visualization, ultrasound visualization, or some combination thereof. Once the first and second guide members have been advanced to the left atrial appendage, one or more positioning and/or stabilizing elements (e.g., balloons or other expandable structures) may be advanced over or in conjunction with the first guide (e.g., it may be coupled to or be part of the first guide) and into the left atrial appendage. Similarly, a closure device may be advanced over the second guide to the exterior of the left atrial appendage. It should be appreciated that the closure device may be any of the closure devices described above.

When placed in the left atrial appendage, the positioning element may be used to help position the snare loop of the closure device. In some variations, an expandable structure may be inflated or otherwise expanded in or near the opening of the left atrial appendage and the snare loop may be closed around the left atrial appendage distal to the expandable structure. In other variations, the expandable member may be expanded inside of the left atrial appendage. In these variations, the expandable member may help position the closure device near the base of the left atrial appendage.

While the expandable member is in an expanded state, the snare loop may be opened and may be placed around a portion of the left atrial appendage. In some variations, placement of the snare loop around the left atrial appendage may be facilitated by rotating the snare loop with an actuating mechanism of the closure device. Once placed around the left atrial appendage, the snare loop may be closed around the left atrial appendage. For example, a control on the handle of the closure device may be used to actuate one or more free ends of the snare to close the snare loop. In some variations, the snare loop may be placed around the left atrial appendage while the expandable member is in its deflated or unexpanded state, and then the expandable member may be expanded after the snare loop is closed. In some instances, it may be desirable to confirm proper closure of the appendage prior to release of the tightening element from the closure device. If closure is not adequate or otherwise not desirable, the snare loop may be opened, repositioned, closed, and then confirmed once again.

In variations of closure devices comprising a tightening element coupled to a suture loop, once proper closure by the snare loop has been determined, the suture loop may be tightened around the left atrial appendage. In variations where the snare loop is coupled to the suture loop, tightening the suture loop may detach the suture loop from the snare loop (e.g., release the suture loop from a retention member, as described in U.S. Pat. No. 8,771,297, entitled "Devices, Systems, and Methods for Closing the Left Atrial Appendage" and filed on Mar. 25, 2008, and U.S. Pat. No. 9,198,664, entitled "Tissue Ligation Devices and Controls Therefor" and filed on Apr. 1, 2010, which were previously incorporated by reference in their entirety). In some variations, a control on the handle may be used to retract a free end of the suture to tighten the suture loop. The snare loop may then be opened and the suture loop may be tightened again. This may help ensure that the suture loop is sufficiently tightened around the left atrial appendage. In some variations, a user may re-tighten the suture loop after waiting for a period of time. This waiting period may allow tissue to readjust and settle within the suture loop, which may allow for better closure. This period of time may be any suitable period of time, such as, for example, greater than about 30 seconds, greater than about a minute, or greater than about 2 minutes.

Prior to the release of the suture loop and the tightening element or the snare loop and the tightening element from the closure device, the tightening element may be in the compressed configuration. In some variations, the act of tightening the suture loop or snare loop around a tissue may compress the tightening element. In other variations, the tightening element may be compressed using a different mechanism than is used to tighten the suture loop or snare loop. In still other variations, the tightening element may be held in the compressed configuration while housed in the closure device, and it may be released in this configuration without further compression. When the tightening element is released in the compressed configuration, it may be configured to decrease the size of the suture loop or snare loop if the size, amount, and/or area of the tissue within the suture loop decreases. The tightening element and the suture loop or snare loop may be released from the closure device in any suitable manner, and in some instances, releasing the tightening element and/or the suture loop or snare loop may comprise severing an end of the suture or snare.

In variations of closure devices comprising a tightening element with an aperture, the tightening element itself may be tightened around the left atrial appendage after the snare loop has closed the tissue. The method of tightening the tightening element may be different for different variations of tightening elements described herein. For example, tightening a tightening element comprising a fluid or gas filled balloon, as shown in FIGS. 17A-17C, may comprise pulling a wire to stretch the balloon around the left atrial appendage and then inflating the balloon with a fluid or a gas. In variations of the methods where a tightening element comprising an aperture is used, the tightening element may be released from the closure device in a configuration such that the aperture size may decrease if the area of the tissue within the aperture decreases.

After releasing the tightening element, the tightening element and the suture loop arrangement, or the tightening element and snare loop arrangement, the closure device may be withdrawn from the body. It should be appreciated that some or all of the guide members or positioning elements may be removed from the left atrial appendage at any suitable point or points during the methods. For example, in some variations, some or all of these structures may be removed from the left atrial appendage after closing the snare loop or suture loop but prior to releasing the tightening element. In other variations, some or all of these structures may be removed after releasing the tightening element. The suture loop, snare loop, and/or the tightening element may be further tightened after some or all of these elements are removed.

It should be appreciated that the tightening element, the tightening element and suture loop arrangement, or the tightening element and snare loop arrangement may be delivered to the target tissue by a different device than the closure devices described herein. For example, a closure device may temporarily close the target tissue with the snare loop, and another device (e.g., a catheter) may deploy the tightening element, tightening element and suture loop arrangement, or tightening element and snare loop arrangement.

Although the foregoing invention has, for the purposes of clarity and understanding, been described in some detail by way of illustration and example, it will be apparent that certain changes and modifications may be practiced, and are intended to fall within the scope of the appended claims. Additionally, it should be understood that the components and characteristics of the devices described herein may be used in any combination and the description of the certain elements or characteristics with respect to a specific figure are not intended to be limiting or suggest that the element cannot be used in combination with any of the other described elements.

We claim:

1. A tissue closure device comprising:
an elongate body;
a snare loop at least partially housed within the elongate body;
a tightening element releasably coupled to the snare loop, wherein the tightening element comprises a loop formed between first and second ends;
a lock comprising a lumen, wherein the first and second ends of the tightening element are disposed within the lumen; and
a pusher slideably disposed within the elongate body proximal of the lock, wherein the pusher is configured to advance the lock distally along the first and second ends of the tightening element.

2. The tissue closure device of claim 1, wherein the snare loop and the tightening element extend from a distal end of the elongate body.

3. The tissue closure device of claim 1 further comprising a retention member, wherein the retention member releasably couples the tightening element and the snare loop.

4. The tissue closure device of claim 1, wherein the tightening element and the lock are releasable from the closure device.

5. The tissue closure device of claim 1, wherein the lock prevents the loop from enlarging when the lock is engaged.

6. The tissue closure device of claim 1, wherein the lock comprises a crimped cylinder, a flattened cylinder, or depressible tabs.

7. The tissue closure device of claim 1, wherein the pusher comprises a lumen therethrough, and wherein the first and second ends of the tightening element are positioned within the lumen of the pusher.

8. The tissue closure device of claim 1, wherein the tightening element is a vessel loop or an elastic band.

9. The tissue closure device of claim 1, wherein the tightening element is radiopaque.

10. The tissue closure device of claim 1, wherein the lumen of the lock comprises a narrow region that prevents the lock from moving relative to the tightening element.

11. The tissue closure device of claim 1, wherein the tightening element comprises an open configuration and a closed configuration, and wherein the tightening element is configured to encircle a left atrial appendage in the open configuration and is configured to close the left atrial appendage in the closed configuration.

12. A tissue closure device comprising:
an elongate body;
a snare loop at least partially housed within the elongate body;
a closure loop defining an aperture;
a retention member releasably coupling the closure loop and the snare loop;
a lock coupled to the closure loop; and
a pusher configured to move the lock,
wherein the device comprises a first configuration in which the lock is moveable relative to the closure loop and a second configuration in which the lock is fixed relative to the closure loop, and wherein in the second configuration, the lock prevents the aperture of the closure loop from enlarging.

13. The tissue closure device of claim 12, wherein the snare loop and the closure loop extend from a distal end of the elongate body.

14. The tissue closure device of claim 12, wherein the closure loop and the lock are releasable from the closure device.

15. The tissue closure device of claim 12, wherein the lock comprises a crimped cylinder, a flattened cylinder, or depressible tabs.

16. The tissue closure device of claim 12, wherein the pusher comprises a lumen therethrough, and wherein a portion of the closure loop is positioned within the lumen of the pusher.

17. The tissue closure device of claim 12, wherein the closure loop is a vessel loop or is formed from an elastic band.

18. The tissue closure device of claim 12, wherein the closure loop is radiopaque.

19. The tissue closure device of claim 12, wherein the lock comprises a lumen, and the lumen of the lock comprises a narrow region that prevents the lock from moving relative to the closure loop.

20. The tissue closure device of claim 12, wherein the closure loop comprises an open configuration and a closed configuration, and wherein the closure loop is configured to encircle a left atrial appendage in the open configuration and is configured to close the left atrial appendage in the closed configuration.

* * * * *